(12) United States Patent
Taylor et al.

(10) Patent No.: US 12,297,231 B2
(45) Date of Patent: May 13, 2025

(54) SHAPE-RESPONSIVE NANOSTRUCTURES

(71) Applicant: Carnegie Mellon University, Pittsburgh, PA (US)

(72) Inventors: Rebecca Taylor, Pittsburgh, PA (US); Sriram Kumar, Pittsburgh, PA (US); Dilhara R. Jayarathna, Cincinnati, OH (US)

(73) Assignee: Carnegie Mellon University, Pittsburgh, PA (US)

( * ) Notice: Subject to any disclaimer, the term of this patent is extended or adjusted under 35 U.S.C. 154(b) by 898 days.

(21) Appl. No.: 17/599,423

(22) PCT Filed: Mar. 27, 2020

(86) PCT No.: PCT/US2020/025392
§ 371 (c)(1),
(2) Date: Sep. 28, 2021

(87) PCT Pub. No.: WO2020/205588
PCT Pub. Date: Oct. 8, 2020

(65) Prior Publication Data
US 2022/0220156 A1     Jul. 14, 2022

Related U.S. Application Data

(60) Provisional application No. 62/919,781, filed on Mar. 29, 2019.

(51) Int. Cl.
*C07K 14/00*     (2006.01)
*C12Q 1/6813*    (2018.01)
*G01N 33/533*    (2006.01)

(52) U.S. Cl.
CPC .......... *C07K 14/003* (2013.01); *C12Q 1/6813* (2013.01); *G01N 33/533* (2013.01)

(58) Field of Classification Search
None
See application file for complete search history.

(56) References Cited

U.S. PATENT DOCUMENTS

| | | |
|---|---|---|
| 8,053,212 B1 | 11/2011 | Benner |
| 8,389,703 B1 | 3/2013 | Benner et al. |
| 8,653,254 B2 | 2/2014 | Umemoto et al. |
| 9,741,948 B2 | 8/2017 | Berger et al. |
| 10,150,665 B2 | 12/2018 | Taylor et al. |
| 2003/0215903 A1 | 11/2003 | Hyman et al. |
| 2016/0083434 A1 | 3/2016 | Ly et al. |
| 2017/0058325 A1 | 3/2017 | Ly et al. |

FOREIGN PATENT DOCUMENTS

| | | |
|---|---|---|
| WO | 2012138955 A2 | 10/2012 |
| WO | 2018058091 A1 | 3/2018 |

OTHER PUBLICATIONS

Pedersen et al. Comparative incorporation of PNA into DNA nanostructures. Molecules 20:17645-17658. (Year: 2015).*

Kim et al., "A Series of Nonpolar Thymidine Analogues of Increasing Size: DNA Base Pairing and Stacking Properties", 2005, pp. 2048-2053, vol. 70, J. Org. Chem., American Chemical Society.

Kim et al., "Quantitative prediction of 3D solution shape and flexibility of nucleic acid nanostructures", 2012, pp. 2862-2868, vol. 40, No. 7, Nucleic Acids Research, Oxford University Press.

Klein et al., "Multiscaffold DNA Origami Nanoparticle Waveguides", 2013, pp. 3850-3856, vol. 13, Nano Lett., American Chemical Society.

Koppelhus et al., "Cellular delivery of peptide nucleic acid (PNA)", 2003, pp. 267-280, vol. 55, Advanced Drug Delivery Reviews, Elsevier.

Kuwahara et al., "Novel Peptide Nucleic Acid That Shows High Sequence Specificity and All-or-None-Type Hybridization with the Complementary DNA", 1999, pp. 256-257, vol. 121, j. Am. Chem. Soc., American Chemical Society.

Kuzuya et al., "Nanomechanical DNA Origami pH Sensors", 2014, pp. 19329-19335, vol. 14, Sensors.

Kuzyk et al., "DNA-based self-assembly of chiral plasmonic nanostructures with tailored optical response", Mar. 15, 2012, pp. 311-314, vol. 483, Nature.

Larsen et al., "Antisense properties of peptide nucleic acid", 1999, pp. 159-166, vol. 1489, Biochimica et Biophysica Acta, Elsevier.

Le et al., "Probing Nucleosome Stability with a DNA Origami Nanocaliper", 2016, pp. 7073-7084, vol. 10, ACS Nano, American Chemical Society.

Levitt, "How many base-pairs per turn does DNA have in solution and in chromatin? Some theoretical calculations", 1978, pp. 640-644, vol. 75, No. 2, Proc. Natl. Acad. Sci. USA.

Liu et al., "Mix and Match Nanobiosensor Design: Logical and Spatial Programming of Biosensors using Self-assembled DNA Nanostructures", pp. 1-43.

Liu et al., "Electrochemical detection of lung cancer specific microRNAs using 3D Dna origami nanostructures", 2015, pp. 57-61, vol. 71, Biosensors and Bioelectronics, Elsevier.

Liu et al., "A DNA Nanostructure Platform for Directed Assembly of Synthetic Vaccines", 2012, pp. 4254-4259, vol. 12, Nano Lett., American Chemical Society.

Lukeman et al., "Two dimensional PNA/DNA arrays: estimating the helicity of unusual nucleic acid polymers", 2004, pp. 1694-1695, Chem. Commun., The Royal Society of Chemistry.

Maier et al., "Self-Assembled DNA Tubes Forming Helices of Controlled Diameter and Chirality", 2017, pp. 1301-1306, vol. 11, ACS Nano, American Chemical Society.

Maier et al., "Magnetic Propulsion of Microswimmers with DNA-Based Flagellar Bundles", 2016, pp. 906-910, vol. 16, Nano Lett., American Chemical Society.

Maune et al., "Self-assembly of carbon nanotubes into two-dimensional geometries using DNA origami templates", Jan. 2010, pp. 61-66, vol. 5, Nature Nanotechnology.

(Continued)

*Primary Examiner* — Samuel C Woolwine
(74) *Attorney, Agent, or Firm* — The Webb Law Firm

(57) ABSTRACT

Provided herein are single-stranded tile (SST) structures prepared from and comprising single-stranded γPNA (ss-γPNA) strands, along with methods of making an SST structure from single-stranded γPNA (ss-γPNA) strands.

23 Claims, 24 Drawing Sheets

Specification includes a Sequence Listing.

(56) References Cited

OTHER PUBLICATIONS

Meijering et al., "Design and Validation of a Tool for Neurite Tracing and Analysis in Fluorescence Microscopy Images", 2004, pp. 167-176, vol. 58A, Cytometry Part A, Wiley-Liss, Inc.
Mirkin, "DNA Topology: Fundamentals", 2002, pp. 1-11, Encyclopedia of Life Sciences, John Wiley & Sons, Ltd.
Morris et al., "Chemically programmed self-sorting of gelator networks", 2013, pp. 1-6, Nature Communications, Macmillan Publishers Limited.
Nakano et al., "The structural stability and catalytic activity of DNA and RNA oligonucleotides in the presence of organic solvents", 2016, pp. 11-23, vol. 8, Biophys Rev.
Nielsen et al., "Sequence-Selective Recognition of DNA by Strand Displacement with a Thymine-Substituted Polyamide", Dec. 6, 1991, pp. 1497-1500, vol. 254, Science.
Nielsen, "Peptide nucleic acid: a versatile tool in genetic diagnostics and molecular biology", 2001, pp. 1-5, Elsevier Science Limited.
Nielsen et al., "An Introduction to Peptide Nucleic Acid", 1999, pp. 89-104, vol. 1(2), Current Issues Molec. Biol., Caister Academic Press.
Ong et al., "Programmable self-assembly of three-dimensional nanostructures from 10,000 unique components", Dec. 7, 2017, pp. 72-80, vol. 552, Nature, Macmillan Publishers Limited.
Pang et al., "Computational modeling of bone density profiles in response to gait: a subject-specific approach", 2012, pp. 379-390, vol. 11, Biomech Model Mechanobiol, Springer-Verlag.
Park et al., "Effect of ionic strength on PNA-DNA hybridization on surfaces and in solution", Jun. 2007, pp. 80-88, vol. 2(2), Biointerphases, American Vacuum Society.
Pedersen et al., "Comparative Incorporation of PNA into DNA Nanostructures", 2015, pp. 17645-17658, vol. 20, Molecules.
Qian et al., "Scaling Up Digital Circuit Computation with DNA Strand Displacement Cascades", Jun. 3, 2011, pp. 1196-1201, vol. 332, Science, www.sciencemag.org.
Rapireddy et al., "Strand Invasion of Mixed-Sequence B-DNA by Acridine-Linked, $\gamma$-Peptide Nucleic Acid ($\gamma$-PNA)", 2007, pp. 15596-15600, vol. 129, J. Am. Chem. Soc., American Chemical Society.
Ray et al., "Peptide nucleic acid (PNA): its medical and biotechnical applications and promise for the future", Jun. 2000, pp. 1041-1060, vol. 14, The FASEB Journal.
Rothemund, "Folding DNA to create nanoscale shapes and patterns", 2006, pp. 297-302, vol. 440, Nature, Nature Publishing Group.
Rothemund et al., "Design and Characterization of Programmable DNA Nanotubes", 2004, pp. 16344-16352, vol. 126, J. Am. Chem. Soc., American Chemical Society.
Roylance, "Shear and Torsion", Jun. 23, 2000, pp. 1-15, Department of Materials Science and Engineering, Massachusetts Institute of Technology, Cambridge, MA.
Sacui et al., "Gamma Peptide Nucleic Acids: As Orthogonal Nucleic Acid Recognition Codes for Organizing Molecular Self-Assembly", 2015, pp. 8603-8610, vol. 137, J. Am. Chem. Soc., American Chemical Society.
Sahu et al., "Synthesis and Characterization of Conformationally Preorganized, (R)-Diethylene Glycol-Containing $\gamma$-Peptide Nucleic Acids with Superior Hybridization Properties and Water Solubility", 2011, pp. 5614-5627, vol. 76, J. Org. Chem., American Chemical Society.
Schmied et al., "DNA Origami Nanopillars as Standards for Three-Dimensional Superresolution Microscopy", 2013, pp. 781-785, vol. 13, Nano Lett., American Chemical Society.
Schnitzbauer et al., "Super-resolution microscopy with DNA-PAINT", 2017, pp. 1198-1228, vol. 12 No. 6, Nature Protocols, Macmillan Publishers Limited.
Seeman, "Nucleic Acid Junctions and Lattices", 1982, pp. 237-247, vol. 99, J. theor. Biol., Academic Press Inc. (London) Ltd.
Seeman, "An Overview of Structural DNA Nanotechnology", 2007, pp. 246-257, vol. 37, Mol Biotechnol, Humana Press Inc.
Sen et al., "On the stability of peptide nucleic acid duplexes in the presence of organic solvents", 2007, pp. 3367-3374, vol. 35, No. 10, Nucleic Acids Research.
Sforza et al., "Induction of Helical Handedness and DNA Binding Properties of Peptide Nucleic Acids (PNAs) with Two Stereogenic Centres", 2007, pp. 5879-5885, Eur. J. Org. Chem., Wiley-VCH Verlag Gmbh & Co. KGaA, Weinheim.
Sim et al., "Oxidation stiffening of PDMS microposts", 2015, pp. 17-23, vol. 3, Extreme Mechanics Letters, Elsevier.
Song et al., "Reconfiguration of DNA molecular arrays driven by information relay", Jul. 28, 2017, pp. 1-8, vol. 357, 371, Science.
Spudich et al., "Effects of hypertrophic and dilated cardiomyopathy mutations on power output by human $\beta$-cardiac myosin", 2016, pp. 161-167, vol. 219, Journal of Experimental Biology, The Company of Biologists Ltd.
Stein et al., "Single-Molecule FRET Ruler Based on Rigid DNA Origami Blocks", 2011, pp. 689-695, vol. 12, ChemPhysChem, Wiley-VCH Verlag Gmbh & Co. KGaA, Weinheim.
Surana et al., "Designing DNA nanodevices for compatibility with the immune system of higher organisms", Sep. 2015, pp. 742-747, vol. 10, Nature Nanotechnology, Macmillan Publishers Limited.
Swenson et al., "Bilingual Peptide Nucleic Acids: Encoding the Languages of Nucleic Acids and Proteins in a Single Self-Assembling Biopolymer", 2019, p. 19038-19047, vol. 141, J. Am. Chem. Soc., American Chemical Society.
Tallihades et al., "Solid-Phase Synthesis of Difficult Purine-Rich PNAs through Selective Hmb Incorporation: Application to the Total Synthesis of Cell Penetrating Peptide-PNAs", Oct. 2017, pp. 1-7, vol. 5, Article 81, Frontiers in Chemistry.
Tackett et al., "Solid-Phase Synthesis of Difficult Purine-Rich PNAs through Selective Hmb Incorporation: Application to the Total Synthesis of Cell Penetrating Peptide-PNAs", 2002, pp. 250-257, vol. 30, No. 4, Nucleic Acids Research, Oxford University.
Ackermann et al., "Pseudo complementary PNA actuators as reversible switches in dynamic DNA nanotechnology", Nucleic Acids Research, Feb. 2013, pp. 4729-4739, vol. 41, No. 8, Oxford University Press.
Acuna et al., "Fluorescence Enhancement at Docking Sites of DNA-Directed Self-Assembled Nanoantennas", www.sciencemag.org, Oct. 26, 2012, pp. 506-511, vol. 338, Science.
Adler-Abramovich et al., "Self-assembled arrays of peptide nanotubes by vapour deposition", nature nanotechnology, Oct. 18, 2009, pp. 849-854, vol. 4, www.nature.com/naturenanotechnology.
Adler-Abramovich et al., "The physical properties of supramolecular peptide assemblies: from building block association to technological applications", Chem Soc Rev, 2014, pp. 6881-6893, vol. 43, The Royal Society of Chemistry.
Amdursky et al., "Blue Luminescence Based on Quantum Confinement at Peptide Nanotubes", Nano Letters, 2009, pp. 3111-3115, vol. 9. No. 9, American Chemical Society.
Amir et al., "Universal computing by DNA origami robots in a living animal", nature nanotechnology, May 2014, pp. 353-357, vol. 9, www.nature.com/naturenanotechnology.
Anderson et al., "Self-assembly of a nanoscale DNA box with a controllable lid", May 2009, pp. 73-77, vol. 459, Nature, Macmillan Publishers Limited.
Avakyan et al., "Reprogramming the assembly of unmodified DNA with a small molecule", Apr. 2016, pp. 368-376, vol. 8, Nature Chemistry, Macmillan Publishers Limited.
Bai et al., "Cryo-EM structure of a 3D DNA origami project", Dec. 4, 2012, pp. 20012-20017, vol. 109, No. 49, PNAS.
Banwell et al., "Rational design and application of responsive a-helical peptide hydrogels", Jul. 2009, pp. 596-600, vol. 8, Nature Materials, Macmillan Publishers Limited.
Berger et al., "Light-emitting self-assembled peptide nucleic acids exhibit both stacking interactions and Watson-Crick base pairing", Apr. 2015, pp. 353-360, vol. 10, Nature Nanotechnology, Macmillan Publishers Limited.
Berger et al., "Molecular self-assembly using peptide nucleic acids", 2017, pp. 1-6, vol. 108:e22930, Peptide Science, Wiley Periodicals, Inc.

(56) References Cited

OTHER PUBLICATIONS

Berger et al., "Spectral Transition in Bio-Inspired Self-Assembled Peptide Nucleic Acid Photonic Crystals", 2016, pp. 2195-2000, vol. 28, Advanced Materials, Wiley-Vch Verlag Gmbh & Co. KGaA, Weinheim.
Bezen et al., "Chiral Molecule-Enhanced Extinction Ratios of Quantum Dots Coupled to Random Plasmonic Structures, " 2018, pp. 3076-3081, vol. 34, Langmuir, ACS Publications.
Bezer et al., "Coordination—Driven Inversion of Handedness in Ligand-Modified PNA", 2011, pp. 11929-11937, vol. 50, Inorganic Chemistry, ACS Publications.
Boyarskaya, et al., "Synthesis of Two New Thymine-Containing Negatively Charged PNA Monomers", 2006, pp. 57-60, vol. 408, Part 1, Doklady Chemistry, Pleiades Publishing, Inc., Russia.
Braasch et al., "Novel Antisense and Peptide Nucleic Acid Strategies for Controlling Gene Expression", Apr. 9, 2002, pp. 4503-4510, vol. 41, No. 14, Biochemistry, American Chemical Society.
Braasch et al., "Synthesis, Analysis, Purification, and Intracellular Delivery of Peptide Nucleic Acids", 2001, pp. 97-107, vol. 23, Methods, Academic Press.
Castro et al., "A primer to scaffolded DNA origami", Mar. 2011, pp. 221-229, vol. 8, No. 3, Nature Methods, Nature America, Inc.
Castro et al., "Mechanical design of DNA nanostructures", 2015, pp. 5913-5921, vol. 7, Nanoscale, The Royal Society of Chemistry.
Christensen et al., "Solid-phase Synthesis of Peptide Nucleic Acids", 1995, pp. 175-183, vol. 3, Journal of Peptide Science, European Peptide Society and John Wiley & Sons, Ltd.
Coin et al., "Solid-phase Peptide Synthesis: from standard procedures to the synthesis of difficult synthesis", 2007, pp. 3247-3256, vol. 2, No. 12, Nature Protocols, Nature Publishing Group.
De La Rica, et al., "Applications of peptide and protein-based materials in bionanotechnology", 2010, pp. 3499-3509, vol. 39, Chem. Soc. Rev., The Royal Society of Chemistry.
Derr et al., "Tug-of-war in Motor Protein Ensembles Revealed with a Programmable DNA Origami Scaffold", Nov. 2, 2012, pp. 662-665, vol. 338, Science.
Dietz et al., "Folding DNA into Twisted and Curved Nanoscale Shapes", Aug. 7, 2009, pp. 725-729, vol. 325, www.sciencemag.org.
Dirks et al., "Paradigms for computational nucleic acid design", 2004, pp. 1392-1403, vol. 32, No. 4, Nucleic Acids Research, Oxford University Press.
Douglas et al., "A Logic-Gated Nanorobot for Targeted Transport of Molecular Payloads", Feb. 17, 2012, pp. 831-834, vol. 335, Science, www.sciencemag.org.
Douglas et al., "Self-assembly of DNA into nanoscale three-dimensional shapes", May 2009, pp. 414-418, vol. 459, nature, Macmillan Publishers Limited.
Dragulescu-Andrasi et al., "A Simple y-Backbone Modification Preorganizes Peptide Nucleic Acid into a Helical Structure", 2006, pp. 10258-10267, vol. 128, J. Am. Chem. Soc., American Chemical Society.
Egholm et al., "Peptide Nucleic Acids (PNA) Oligonucleotide Analogues with an Achiral Peptide Backbone", 1992, pp. 1895-1897, vol. 114, J. Am. Chem. Soc., American Chemical Society.
Egholm et al., "PNA Hybridizes to complementary oligonucleotides obeying the Watson-Crick hydrogen-bonding rules", Oct. 7, 1993, pp. 566-568, vol. 365, Nature, Nature Publishing Company.
Egholm et al., "Recognition of Guanine and Adenine in DNA by Cytosine and Thymine Containing Peptide Nucleic Acids (PNA)", 1992, pp. 9677-9678, vol. 114, J. Am. Chem. Soc., American Chemical Society.
"Solution Structure of a peptide nucleic acid-DNA duplex", May 1996, pp. 410-413, vol. 3, No. 5, nature structural biology.
Feng et al., "A Two-State DNA Lattice Switched by DNA Nanoactuator", 2003, pp. 4342-4346, vol. 42, Angew. Chem. Int. Ed., Wiley-VCH Verlag Gmbh & Co. KGaA, Weinheim.
Fischer et al., "Investigating the aggregation behaviour of DNA origami frames", 2015, pp. 1375-1381, vol. 212, No. 6, Phys. Status Solidi, Wiley-VCH Verlag Gmbh & Co. KGaA, Weinheim.

Flory et al., Purification and assembly of thermostable Cy5 labeled $\gamma$-PNAs into a 3D DNA nanocage, 2014, pp. e992181-1 through e992181-8, vol. 5, Issue 3, Research Paper, Taylor & Francis Group, LLC.
Giesen et al., "A formula for thermal stability (Tm) prediction of PNA/DNA duplexes", 1998, pp. 5004-5006, vol. 26, No. 21, Nucleic Acids Research, Oxford University Press.
Gnapareddy et al., "Fabrication and characterization of PNA-DNA hybrid nanostructures", 2014, pp. 35554-35558, vol. 4, RSC Adv., The Royal Society of Chemistry.
Gu et al., "A proximity-based programmable DNA nanoscale assembly line", May 2010, pp. 202-206, vol. 465, Nature, Macmillan Publishers Limited.
Han et al., "DNA Origami with Complex Curvatures in Three-Dimensional Space", Apr. 15, 2011, pp. 342-346, vol. 332, Science, www.sciencemag.org.
Hariadi et al., "Mechanical coordination in motor ensembles revealed using engineered artificial myosin filaments," Aug. 2015, pp. 696-701, vol. 10, Nature Nanotechnology, Macmillan Publishers Limited.
Hartgerink et al., "Self-Assembly and Mineralization of Peptide-Amphiphile Nanofibers", Nov. 23, 2001, pp. 1684-1688, vol. 294, Science, www.sciencemag.org.
Hirst et al., "Biocatalytic induction of supramolecular order", Dec. 2010, pp. 1089-1095, vol. 2, Nature Chemistry, Macmillan Publishers Limited.
Homburger et al., "Multidimensional structure-function relationships in human $\beta$-cardiac myosin from population-scale genetic variation", Jun. 14, 2016, pp. 6701-6706, vol. 113, No., 24, PNAS.
Hyde et al., "Internal Aggregation during Solid Phase Peptide Synthesis. Dimethyl Sulfoxide as a Powerful Dissociating Solvent", 1992, pp. 1573-1575, J. Chem. Soc. Commun.
Waki et al., "A programmable DNA origami nanospring that reveals force-induced adjacent binding of myosin VI heads", 2016, pp. 1-10, vol. 7:13715, Nature Communications.
Jayarathna et al., "Metal Coordination to Ligand-Modified Peptide Nucleic Acid Triplexes", 2018, pp. 6865-6872, vol. 57, Inorg. Chem., American Chemical Society.
Jungmann et al., "Multiplexed 3D cellular super-resolution imaging with DNA-PAINT and Exchange-PAINT", Mar. 2014, pp. 313-321, vol. 11, No. 3, Nature Methods.
Ke et al., "Three-Dimensional Structures Self-Assembled from DNA Bricks", Nov. 30, 2012, pp. 1177-1183, vol. 338, Science, www.sciencemag.org.
Kearney et al., "DNA Origami: Folded DNA-Nanodevices That Can Direct and Interpret Cell Behavior", pp. 1-49, Wiley-VCH.
Tassinari et al., "Chirality Dependent Charge Transfer Rate in Oligopeptides", 2018, pp. 1-6, vol. 30, Adv. Mater., Wiley-Vch Verlag Gmbh & Co. KGaA, Weinheim.
Taylor, "Microfabricated Tools for Functional Assessment of Developing Cardiomyocytes a Dissertation", Mar. 2013, Stanford University.
Taylor et al., "Planar patterned stretchable electrode arrays based on flexible printed circuits", 2013, pp. 1-7, vol. 23, J. Micromech. Microeng., IOP Publishing.
Taylor et al., "Sacrificial layer technique for axial force post assay of immature cardiomyocytes", 2013, pp. 171-181, vol. 15, Biomed Microdevices, Springer Science Business Media LLC.
Rape et al., "Mechanobiology of Cell-Cell and Cell-Matrix Interactions", 2011, 1-329, e-ISBN 978-1-4419-8083-0, Springer, New York.
Tikhomirov et al., "DNA-based programming of quantum dot valency, self-assembly and luminescence", Aug. 2011, pp. 485-190, vol. 6, Nature Nanotechnology, Macmillan Publishers Limited.
Vernille et al., "Peptide Nucleic Acid (PNA) Amphiphiles: Synthesis, Self-Assembly, and Duplex Stability", 2004, pp. 1314-1321, vol. 15, Bioconjugate Chem., American Chemical Society.
Wagenbauer et al., "How We Make DNA Origami", 2017, pp. 1873-1885, vol. 18, ChemBioChem, Wiley-VCH Verlag Gmbh & Co. KGaA, Weinheim.
Wang, "DNA biosensors based on Peptide Nucleic Acid (PNA) recognition layers. A review", 1998, pp. 757-762, vol. 13, Biosensors & Bioelectronics, Elsevier.

(56) References Cited

OTHER PUBLICATIONS

Wittung et al., "DNA-like double helix formed by peptide nucleic acid", Apr. 7, 1994, pp. 561-563, vol. 368, Nature, Nature Publishing Group.

Wittung et al., "Induced Chirality in PNA-PNA Duplexes", Oct. 18, 1995, pp. 1-7, vol. 117 No. 41, Journal of the American Chemical Society.

Yamazaki et al., "Clear-cut observation of PNA invasion using nanomechanical DNA origami devices", 2012, pp. 11361-11363, vol. 48, Chem. Commun., The Royal Society of Chemistry.

Yang et al., "Dielectric Properties of Binary Solvent Mixtures of Dimethyl Sulfoxide with Water", 2009, pp. 1261-1270, vol. 10, Int. J. Mol. Sci.

Yang et al., "Self-Assembly of DNA Rings from Scaffold-Free DNA Tiles", 2013, pp. 1862-1866, vol. 13, Nano Lett., American Chemical Society.

Yeh et al., "Crystal Structure of Chiral γPNA with Complementary DNA Strand: Insights into the Stability and Specificity of Recognition and Conformational Preorganization", 2010, pp. 10717-10727, vol. 132, J. Am. Chem. Soc., American Chemical Society.

Yin et al., "Programming DNA Tube Circumferences", Aug. 8, 2008, pp. 824-826, vol. 321, Science, www.sciencemag.org.

Zhang, "Fabrication of novel biomaterials through molecular self-assembly", Oct. 2003, pp. 1171-1178, vol. 21, No. 10, Nature Bioltechnology.

Zhang et al., "Dynamic DNA nanotechnology using strand-displacement reactions", Feb. 2011, pp. 103-113, vol. 3, Nature Chemistry, Macmillan Publishers Limited.

Zhang et al., "Control of DNA Strand Displacement Kinetics Using Toehold Exchange", 2009, pp. 17303-17314, vol. 131, J. Am. Chem. Soc., American Chemical Society.

Zhang et al., "Integrating DNA strand-displacement circuitry with DNA tile self-assembly", 2013, pp. 1-10, Nature Communications, Macmillan Publishers Limited.

Zhang et al., "DNA Origami as an In Vivo Drug Delivery Vehicle for Cancer Therapy", 2014, pp. 6633-6643, vol. 8, No. 7, ACS Nano, American Chemical Society.

Zhang et al., "DNA Electronic Logic Gates Based on Metal-Ion-Dependent Induction of Oligonucleotide Structural Motifs", 2013, pp. 6961-6965, vol. 19, Chem. Eur. J., Wiley-VCH Verlag Gmbh &Co. KGaA, Weinheim.

Bahal et al., "Single-Stranded γPNAs for In Vivo Site-Specific Genome Editing via Watson-Crick Recognition", 2014, pp. 331-342, vol. 14(5), Curr. Gene Ther., Bentham Science Publishers.

Janssen et al., "ssPNA templated assembly of oligo(p-phenylenevinylene)s", 2010, pp. 109-111, Chem. Commun., The Royal Society of Chemistry.

Wang et al., "Self-assembly of fully addressable DNA nanostructures from double crossover tiles", 2016, pp. 7989-7996, vol. 44, No. 16, Nucleic Acids Research, Oxford University Press.

Cattani-Scholz et al., "PNA-PEG Modified Silicon Platforms as Functional Bio-Interfaces for Applications in DNA Microarrays and Biosensors", 2009, pp. A-H, Bio Macromolecules, American Chemical Society.

Schneider et al., "NIH Image to ImageJ: 25 years of Image Analysis", Jul. 2012, pp. 671-675, vol. 9(7), Nat. Methods.

Woods et al., "Diverse and robust molecular algorithms using reprogrammable DNA self-assembly", Mar. 2019, pp. 366-372, Nature.

Wei et al., "Stretchable microelectrode array using room-temperature liquid alloy interconnects", 2011, pp. 1-8, vol. 21. J. Micromech. Microeng., IOP Publishing Ltd.

Hudoba et al., "Dynamic DNA Origami Device for Measuring Compressive Depletion Forces", 2017, pp. 6566-6573, vol. 11, ACS Nano, ACS Publications.

Ghadiri et al., "Self-assembling organic nanotubes based on a cyclic peptide architecture", Nov. 25, 1993, pp. 324-327, vol. 366, Nature, Nature Publishing Group.

\* cited by examiner

Naturally compatible nucleobases

Orthogonal nucleobases

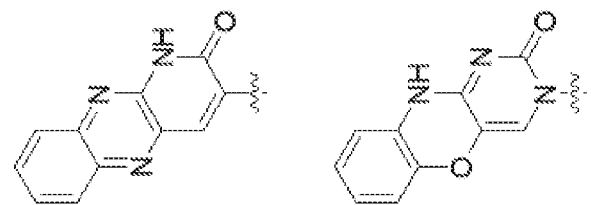
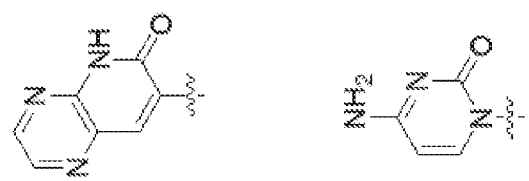
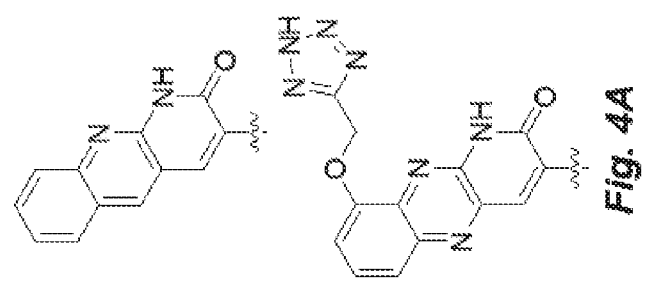
Fig. 4A
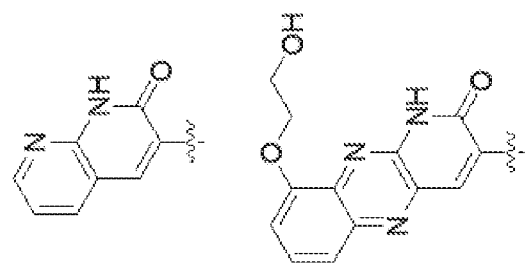
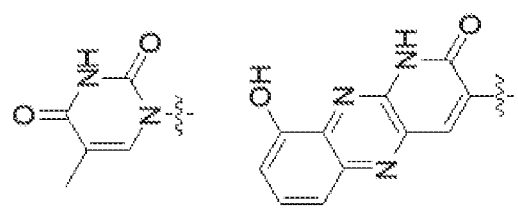

5 base offsets per helix

100° per 5 bases of PNA, approximately 90° right angle turn

SHAPE-RESPONSIVE NANOSTRUCTURES

CROSS REFERENCE TO RELATED APPLICATIONS

This application is the United States national phase of International Application No. PCT/US2020/025392 filed Mar. 27, 2020, and claims the benefit of U.S. Provisional Application No. 62/919,781, filed Mar. 29, 2019, the disclosures of which are hereby incorporated herein by reference in their entirety.

STATEMENT REGARDING FEDERAL FUNDING

This invention was made with government support under Grant No. FA9550-18-1-0199 awarded by the Air Force Office of Scientific Research. The government has certain rights in the invention.

REFERENCE TO A SEQUENCE LISTING SUBMITTED VIA EFS-WEB

The content of the ASCII text file of the sequence listing named "6526_2001071_ST25.txt" which is 2,102 bytes in size was created on Mar. 27, 2020, and electronically submitted via EFS-Web herewith the application is incorporated herein by reference in its entirety.

Structural DNA nanotechnology has been an active field since 1982 when Nadrian Seeman published on the formation of nucleic acid lattices using the rules of Watson-Crick base pairing and engineered crossover junctions (Seeman, Nadrian C. Nucleic Acid Junctions and Lattices. *Journal of Theoretical Biology* 99, 2 (1982), 237-247). In 2006 Rothemund et al. discovered the scaffolded DNA nanotechnology and ignited DNA-based nanostructures nanotechnology (Rothemund, P. W. K. Folding DNA to create nanoscale shapes and patterns. *Nature* 440, 7082 (2006), 297-302.). Scaffolded DNA technology enables the creation of arbitrary nanometer-scale self-assembled structures with a simple anneal process and high formation yields. With the advent of easy to design DNA nanostructures, the scaffolded approach quickly become the dominant approach. In 2004, Rothemund explored the crossover tile approach for making long nanotubes (Rothemund, P. W. K., Ekani-Nkodo, A., Papadakis, N., Kumar, A., Fygenson, D. K., and Winfree, E. Design and characterization of programmable DNA nanotubes. *Journal of the American Chemical Society* 126, 50 (2004), 16344-16352.). This approach utilized DNA strands (or oligos) 42 bases in length to create periodic structures like ribbons and nanotubes that polymerized to form filaments up to 50 µm. This approach requires small numbers of distinct oligonucleotides and, importantly, does not require the use of kilobase-scale scaffold strands. In 2008 Yin et al. improved upon the design on the fundamental strand element, which he named a single stranded tile (SST) (Yin, P., Hariadi, R. F., Sahu, S., Choi, H. M. T., Park, S. H., Labean, T. H., And Reif, J. H. Programming DNA tube circumferences. Science 321, 5890 (2008), 824-826.) Yang et al. built on this approach to create SST systems using 21 base strands and demonstrated that these nanotubes could be bent to form nanorings when balanced insertions and deletions were introduced into the structure (Yang, Y., Zhao, Z., Zhang, F., Nangreave, J., Liu, Y., And Yan, H. Self-assembly of DNA rings from scaffold-free DNA tiles. Nano Letters 13, 4 (2013), 1862-1866).

From an engineering perspective, the small number of strands in each SST system allows for rapid prototyping of designs. Further, the periodic nature of these constructs allows for easy, high-density decoration as well as high internal stress generation due to programmed pre-stress and strand invasion. Dynamic conformation change of DNA nanostructures in response to analyte-binding and ion concentration change has recently been shown for applications including force spectroscopy, responsive accordion-like structures and drug delivery. Strand-displacement and kinetically tuned toehold-mediated strand displacement have also been shown to be powerful approaches for dynamically controlling formation and actuation of structural DNA nanotechnology.

Bottom-up manufacturing with DNA has emerged as a game-changing approach for creating the following structural paradigms: (1) DNA-based nanostructures like DNA origami, (2) programmable materials whose multi-scale assembly is directed by DNA binding, and (3) hybrid top-down/bottom-up systems that leverage traditional lithographic microfabrication alongside self-assembly processes. These systems benefit from the robust sequence complementarity and specificity of DNA. Despite its potential to transform diagnostics, therapeutics, nanomachines, nano-sensing, and molecular computation, there are, as yet, no consumer-directed or medical products on the market made from structural DNA nanotechnology. The broader impact of structural DNA nanotechnology has, in part, been limited due to restrictions imposed by the scope of DNA as a nanomaterial; it is dependent on high salt concentrations for structural stabilization, susceptible to enzymatic degradation and undergoes denaturation in organic solvents. This limits the capability of unprotected DNA nanostructures for realizing many applications that require robust structural stability and transferability to other systems. For example, processes used in polymer synthesis and peptide synthesis often utilize polar aprotic solvents like dimethyl formamide (DMF) and dimethyl sulfoxide (DMSO) that can cause denaturation, reduced thermal stability and conformational changes in DNA duplexes. To create protected DNA origami that can operate in such solutions, nanostructures are first annealed in aqueous buffers and then stabilized using protection processes including base-specific cross-linking, coating with protective molecules, or encapsulation within protective structures. Only then can these structures be transferred to harsh environments.

Solution-compatible nanostructures could introduce the reliable sub-nanometer structural control of DNA nanotechnology into broad fields like polymer synthesis, in which sequence-dependent structural control remains a challenge. Previous studies aiming to mimic the self-assembling properties of DNA have investigated nucleobase-containing polymers, DNA-synthetic polymer conjugates and synthetic DNA-mimics with altered backbones called xeno nucleic acids. Conjugation of DNA to synthetic polymers through a wide range of chemistries often results in less than desirable yield of conjugate products in organic solvents, with decreasing yield upon introducing more hydrophobic polymers. Strategies to synthesize nucleobase-containing polymers are currently limited by the lack of specific sequence control and the need for novel nucleobase-containing molecular structures including monomers, oligomers, or polymers. Synthetic nucleic acid mimics, or xeno nucleic acid strategies, currently hold the most promise for translating nucleic acid nanotechnology into organic solvents, with peptide nucleic acid (PNA) as a popular candidate among them.

Peptide nucleic acid was first presented in the early 1990's as a novel strategy to generate artificially synthesized biopolymers. Their backbones consist of uncharged repeats of N-(2-aminoethyl) glycine units (AEG) linked by peptide bonds. PNAs exhibit many interesting properties, including high binding affinity to DNA and RNA, a low dependency on ionic strength, high chemical stability, high sequence specificity and resistance to both nucleases and proteases. However, a modular approach to self-assemble multiple PNA oligomers via programmed complementarity remains largely unanswered.

SUMMARY

A single-stranded tile (SST) structure is provided. The structure comprises a complex of one or more single-stranded gamma peptide-nucleic acid (ss-γPNA) species, the ss-γPNAs of the SST structure comprising one or more pairs of complementary binding domains arranged on the one or more ss-γPNA species to produce a periodic arrangement of at least 3 molecules of the one or more ss-γPNA species by hybridization of the complementary nucleobase sequences of the one or more pairs of complementary binding domains.

A method of making a single-stranded tile (SST) structure is provided. The method comprises mixing one or more single-stranded gamma peptide-nucleic acid (ss-γPNA) species in a solvent for the ss-γPNA; and complexing the one or more ss-γPNA species in the solvent to form an ordered complex of the one or more single-stranded gamma peptide-nucleic acids (ss-γPNAs). The ss-γPNA species comprise one or more pairs of complementary binding domains comprising complementary nucleobase sequences arranged on the one or more ss-γPNA species to produce a periodic arrangement of at least 3 molecules of the one or more ss-γPNA species by hybridization of the complementary nucleobase sequences to produce the SST structure.

A nanoscale actuator comprising an SST structure is provided. The actuator comprises a single-stranded tile (SST) structure is provided. The SST structure comprises a complex of one or more single-stranded gamma peptide-nucleic acid (ss-γPNA) species, the ss-γPNAs of the SST structure comprising one or more pairs of complementary binding domains arranged on the one or more ss-γPNA species to produce a periodic arrangement of at least 3 molecules of the one or more ss-γPNA species by hybridization of the complementary nucleobase sequences of the one or more pairs of complementary binding domains, and a nucleic acid or nucleic acid analog able to hybridize with a binding domain of a strand of the SST structure and altering the structure of the SST structure. A kit comprising the actuator and the nucleic acid or nucleic acid analog able to hybridize with a binding domain of a strand of the SST structure and altering the structure of the SST structure also is provided.

A method of modifying an SST structure is provided. The method comprises contacting an SST structure comprising a PNA strand or a complex of one or more single-stranded gamma peptide-nucleic acid (ss-γPNA) species, the ss-γPNAs of the SST structure comprising one or more pairs of complementary binding domains arranged on the one or more ss-γPNA species to produce a periodic arrangement of at least 3 molecules of the one or more ss-γPNA species by hybridization of the complementary nucleobase sequences of the one or more pairs of complementary binding domains with a nucleic acid or nucleic acid analog able to hybridize with a binding domain of a strand of the SST structure and altering the structure of the SST structure, and thereby changing the physical structure of the SST structure.

A sensor is provided comprising an SST structure. The SST structure comprises a complex of one or more single-stranded gamma peptide-nucleic acid (ss-γPNA) species, the ss-γPNAs of the SST structure comprising one or more pairs of complementary binding domains arranged on the one or more ss-γPNA species to produce a periodic arrangement of at least 3 molecules of the one or more ss-γPNA species by hybridization of the complementary nucleobase sequences of the one or more pairs of complementary binding domains. The method comprises contacting the SST structure with an analyte that alters the structure of the SST structure, and detecting the alteration of the structure of the SST structure.

BRIEF DESCRIPTION OF THE DRAWINGS

FIGS. 3, 4A, 4B, and 5A-5C provide structures of exemplary nucleobases.

FIG. 19A: TIRF panels (5 μm scale bar) of the self-assemblies formed by PNA in 75% DMSO:H$_2$O (v/v) with different concentration of SDS ranging from 0 to 17.5 mM. With increasing concentrations of SDS [0-5.25 mM], thinner morphologies of the nanotubes become more dominant. When concentrations of SDS neared or exceeded the CMC concentration (8.2 mM), networked morphologies of PNA with increasing propensity was observed. FIG. 19B: TEM panels (100 nm scale bar) of PNA nanostructures annealed in 75% DMSO:H$_2$O (v/v) with 5.25 mM SDS shows nanotubes with diameters 8-12 nm range. FIG. 19C: Overlay of width distribution of PNA nanostructures with 5.25 mM SDS (sample size, N=185) and without SDS (sample size, N=171) using TEM studies. Nanotubes in the presence of 5.25 mM SDS show a tight distribution with a median width of 11.3 nm.

DETAILED DESCRIPTION

Figure 1:
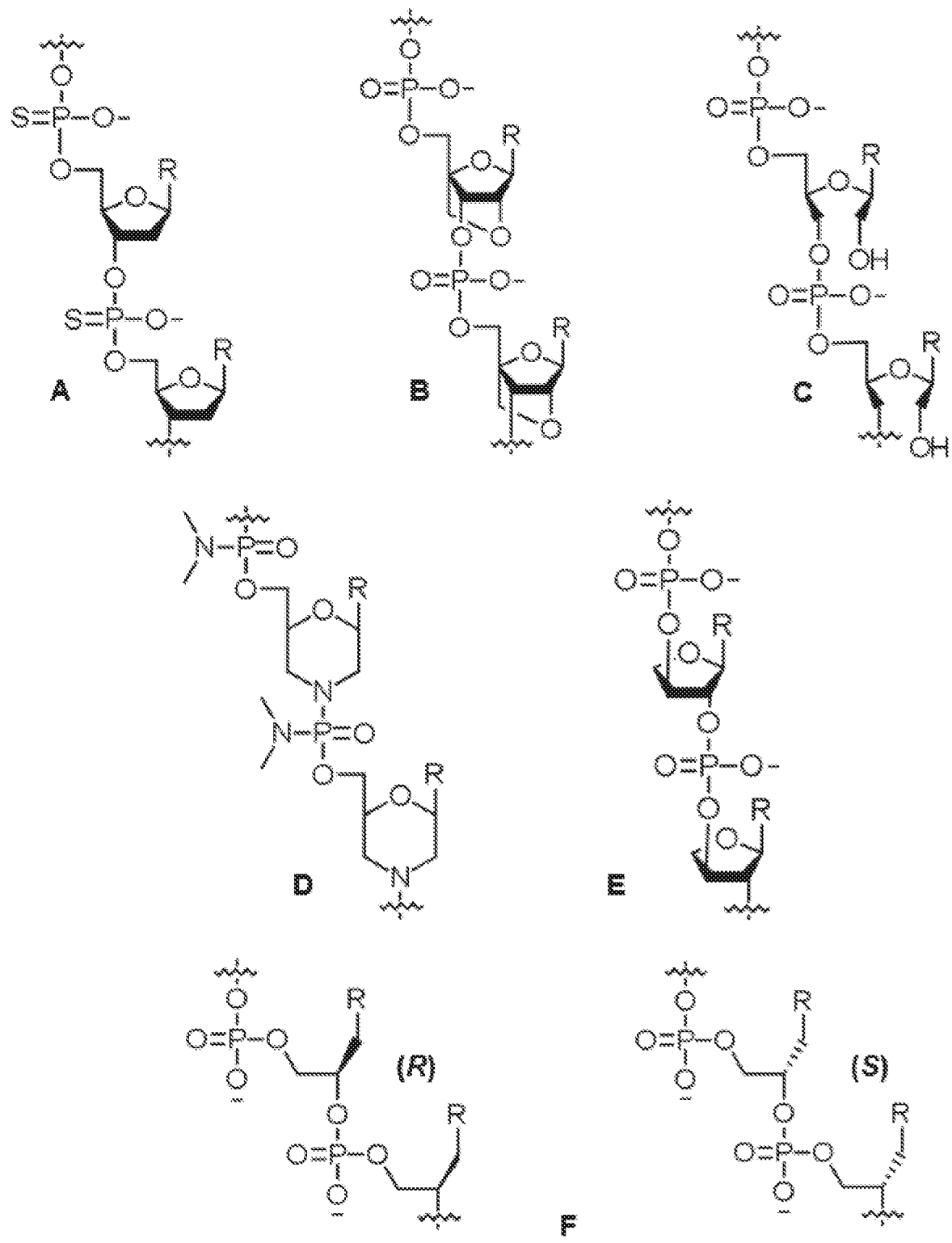
FIG. 1 provides structures of exemplary nucleic acid analogs.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more. A "plurality" is two or more.

As used herein, the term "comprising" is open-ended and may be synonymous with "including", "containing", or "characterized by". The term "consisting essentially of" limits the scope of a claim to the specified materials or steps and those that do not materially affect basic and novel characteristic(s). The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

The following numbered clauses provide exemplary aspects or embodiments of the present invention.

Clause 1. A single-stranded tile (SST) structure, comprising a complex of one or more single-stranded gamma peptide-nucleic acid (ss-γPNA) species, the ss-γPNAs of the SST structure comprising one or more pairs of complementary binding domains arranged on the one or more ss-γPNA species to produce a periodic arrangement of at least 3 molecules of the one or more ss-γPNA species by hybridization of the complementary nucleobase sequences of the one or more pairs of complementary binding domains.

Clause 2. The structure of clause 1, comprising a periodic arrangement of three or more ss-γPNA species, each ss-γPNA species having at least one or more binding domain that is a member of one or more binding domain pairs of the ss-γPNA species of the structure, where the binding domains are arranged on the ss-γPNA species to produce the periodic arrangement.

Clause 3. The structure of clause 1 or 2, comprising at least 10, at least 25, or at least 100 periodically-arranged ss-γPNA molecules.

Clause 4. The structure of any one of clauses 1-3, wherein at least one of the ss-γPNA molecules of a first ss-γPNA species are hybridized to at least two ss-γPNA molecules of one or more different ss-γPNA species than the first ss-γPNA species.

Clause 5. The structure of clause 4, wherein at least two, at least three, or at least four ss-γPNA molecules having different sequences from each other are hybridized to at least two of the ss-γPNA molecules having different sequences.

Clause 6. The structure of any one of clauses 1-5, wherein the ss-γPNA backbone of the one or more ss-γPNA species comprises a plurality of γPNA backbone residues linked to a nucleobase, in which one or more of the γPNA backbone residues are substituted with a group an ethylene glycol unit having from 1 to 100 ethylene glycol residues, optionally at the gamma carbon.

Clause 7. The structure of clause 6, wherein the ethylene glycol unit is selected from the group consisting of: —(OCH$_2$—CH$_2$)$_q$OP$_1$; —(OCH$_2$—CH$_2$)$_q$—NHP$_1$; —(SCH$_2$—CH$_2$)$_q$—SP$_1$; —(OCH$_2$—CH$_2$)$_r$—OH; —(OCH$_2$—CH$_2$)$_r$—NH$_2$; —(OCH$_2$—CH$_2$)$_r$—NHC(NH)NH$_2$; or —(OCH$_2$—CH$_2$)$_r$—S—S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene and (C$_3$-C$_8$)cycloalkyl(C$_1$-C$_6$)alkylene; where q is an integer from 0 to 50; r is an integer from 1 to 50, and s is an integer from 1 to 50, wherein the ethylene glycol unit is optionally attached to the one or more γPNA backbone residues by a (C$_1$-C$_6$) divalent hydrocarbyl linker or a poly(ethylene glycol) linker comprising from two to six ethylene glycol moieties.

Clause 8. The structure of any one of clauses 1-7, wherein one or more of the ss-γPNA species comprises a RH-γPNA residue.

Clause 9. The structure of any one of clauses 1-7, wherein one or more of the ss-γPNA species comprises a LH-γPNA residue.

Clause 10. The structure of any one of clauses 1-9, wherein both LH-γPNA residues and RH-γPNA residues are present in the one or more ss-γPNA species.

Clause 11. The structure of any one of clauses 1-10, wherein one or more of the one or more ss-γPNA species has the structure:

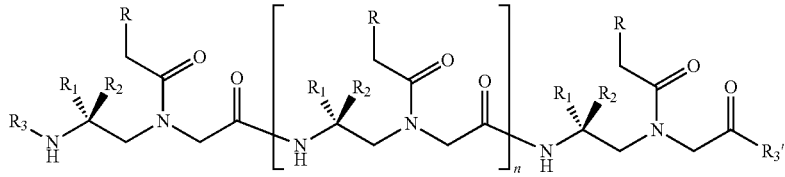

where, each R is independently, a nucleobase;

n is 3 or more, 4 or more, 5 or more, or 6 or more, such as an integer ranging from 3 to 30 or from 10 to 30, for example, 6, 7, 8, 9, 10, 11, 12, 13, 14, 15, 16, 17, 18, 19, 20, 21, 22, 23, 24, 25, 26, 27, 28, 29, or 30;

each R$_1$ and R$_2$ are, independently: a guanidine-containing group, an amino acid side chain, methyl, ethyl, linear or branched (C$_3$-C$_8$)alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$)cycloalkyl, (C$_3$-C$_8$)aryl(C$_1$-C$_6$)alkylene, (C$_3$-C$_8$)cycloalkyl(C$_1$-C$_6$)alkylene, each optionally substituted with a polyethylene glycol chain comprising from 1 to 50 units; H—CH$_2$—(OCH$_2$—CH$_2$)$_q$OP$_1$; —CH$_2$—(OCH$_2$—CH$_2$)$_q$—NHP$_1$; —CH$_2$—(SCH$_2$—CH$_2$)$_q$—SP$_1$; —CH$_2$—(OCH$_2$—CH$_2$)$_r$—OH; —CH$_2$—(OCH$_2$—CH$_2$)$_r$—NH$_2$; —CH$_2$—(OCH$_2$—CH$_2$)$_r$—NHC(NH)NH$_2$; or —CH$_2$—(OCH$_2$—CH$_2$)$_r$—S—S[CH$_2$CH$_2$]$_s$NHC(NH)NH$_2$, where P$_1$ is H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene or (C$_3$-C$_8$)cycloalkyl(C$_1$-C$_6$)alkylene; q is an integer from 0 to 50; r is an integer from 1 to 50, and s is an integer from 1 to 50;

R₃ is H or one or more natural or non-proteinogenic amino acids, a guanidine-containing group, a tag or a label; and R₃' is OH or one or more natural or non-proteinogenic amino acids, a guanidine-containing group, a tag or a label.

Clause 12. The structure of any one of clauses 1-11, comprising a plurality of linearly-arranged contiguous strands comprising at least one of the one or more of the ss-γPNA species, and each of the contiguous strands comprising binding domains complementary to a binding domain on a different contiguous strand, forming a linear structure.

Clause 13. The structure of clause 12, further comprising: two or more pluralities of linearly-arranged contiguous strands comprising at least one of the one or more of the ss-γPNA species producing two or more linear structures; and one or more crosslinking strands comprising at least one of the one or more of the ss-γPNA species that each bind nucleobase sequences in two different linear structures formed from the pluralities of linearly-arranged contiguous strands, forming an ordered bundle of the linear structures.

Clause 14. The structure of clause 13, comprising three different linear structures, and three different crosslinking ss-γPNA strands forming an ordered bundle of three linear structures.

Clause 15. The structure of any one of clauses 1-14, further comprising a single-stranded nucleic acid or a nucleic acid analog, such as a single-stranded deoxyribonucleic acid or a peptide nucleic acid, having a binding domain complementary to a binding domain of one or more of the one or more ss-γPNA species.

Clause 16. The structure of any one of clauses 1-15, wherein the complementary binding domains are less than 10 contiguous nucleobases each, such as from 3 to 8 contiguous nucleobases, such as 3, 4, 5, 6, 7, or 8 contiguous nucleobases.

Clause 17. The structure of any one of clauses 1-16, wherein at least one of the one or more of the ss-γPNA species has at least 10%, from 10% to 50%, or from 20% to 40%, by number, γPNA residues.

Clause 18. The structure of any one of clauses 1-17, wherein the SST structure is in a solvent mixture comprising a solvent that does not interfere with hydrogen-bonding donor/acceptor activity to the extent that it interferes with assembly and/or stability of the SST structure, such as a polar aprotic solvent or a polar aprotic organic solvent, such as dimethylsulfoxide (DMSO), dimethylformamide (DMF), or a combination thereof.

Clause 19. The structure of clause 18, wherein the solvent mixture comprises an anionic surfactant, such as sodium dodecyl sulfate (SDS), optionally below the critical micelle concentration of the surfactant in the solvent.

Clause 20. The structure of any one of clauses 1-19, wherein one or more of the of one or more ss-γPNA species is less than 20, less than 19, less than 18, less than 17, less than 16, less than 15, less than 14, or less than 13 bases long.

Clause 21. The structure of any one of clauses 1-20, wherein at least one of the one or more ss-γPNA species comprises: a guanidine-containing group, an amino acid side chain, and/or one or more contiguous amino acid residues at either or both the C-terminal and/or N-terminal ends of the ss-γPNA.

Clause 22. The structure of any one of clauses 1-21, formed into a ring or mesh.

Clause 23. A method of making a single-stranded tile (SST) structure, comprising: mixing one or more single-stranded gamma peptide-nucleic acid (ss-γPNA) species in a solvent for the ss-γPNA; and complexing the one or more ss-γPNA species in the solvent to form an ordered complex of the one or more single-stranded gamma peptide-nucleic acids (ss-γPNAs), wherein the ss-γPNA species comprising one or more pairs of complementary binding domains comprising complementary nucleobase sequences arranged on the one or more ss-γPNA species to produce a periodic arrangement of at least 3 molecules of the one or more ss-γPNA species by hybridization of the complementary nucleobase sequences to produce the SST structure.

Clause 24. The method of clause 23, comprising mixing in the solvent three or more ss-γPNA species, each ss-γPNA species having at least one or more binding domain that is a member of one or more binding domain pairs of the ss-γPNA species of the structure, where the binding domains are arranged on the ss-γPNA species to produce the periodic arrangement.

Clause 25. The method of clause 23 or 24, producing an SST structure comprising at least 10, at least 25, or at least 100 periodically-arranged ss-γPNA molecules.

Clause 26. The method of any one of clauses 23-25, wherein at least one of the ss-γPNA molecules of a first ss-γPNA species are hybridized to at least two ss-γPNA molecules of one or more different ss-γPNA species than the first ss-γPNA species.

Clause 27. The method of clause 26, wherein at least two, at least three, or at least four ss-γPNA molecules having different sequences from each other are hybridized to at least two of the ss-γPNA molecules having different sequences.

Clause 28. The method of any one of clauses 23-27, wherein the ss-γPNA backbone of the one or more ss-γPNA species comprises a plurality of γPNA backbone residues linked to a nucleobase, in which one or more of the γPNA backbone residues are substituted with a group an ethylene glycol unit having from 1 to 100 ethylene glycol residues, optionally at the gamma carbon.

Clause 29. The method of clause 28, wherein the ethylene glycol unit is selected from the group consisting of: —(OCH₂—CH₂)$_q$OP₁; —(OCH₂—CH₂)$_q$—NHP₁; —(SCH₂—CH₂)$_q$—SP₁; —(OCH₂—CH₂)$_r$—OH; —(OCH₂—CH₂)$_r$—NH₂; —(OCH₂—CH₂)$_r$—NHC(NH)NH₂; or —(OCH₂—CH₂)$_r$—S—S[CH₂CH₂]$_s$NHC(NH)NH₂, where P₁ is H, (C₁-C₅)alkyl, (C₂-C₅)alkenyl, (C₂-C₅)alkynyl, (C₃-C₈)aryl, (C₃-C₈)cycloalkyl, (C₃-C₈)aryl(C₁-C₆)alkylene and (C₃-C₈)cycloalkyl(C₁-C₆)alkylene; where q is an integer from 0 to 50; r is an integer from 1 to 50, and s is an integer from 1 to 50, wherein the ethylene glycol unit is optionally attached to the one or more γPNA backbone residues by a (C₁-C₆) divalent hydrocarbyl linker or a poly(ethylene glycol) linker comprising from two to six ethylene glycol moieties.

Clause 30. The method of any one of clauses 23-29, wherein one or more of the ss-γPNA species comprises a RH-γPNA residue.

Clause 31. The method of any one of clauses 23-29, wherein one or more of the ss-γPNA species comprises a LH-γPNA residue.

Clause 32. The method of any one of clauses 23-31, wherein both LH-γPNA residues and RH-γPNA residues are present in the one or more ss-γPNA species.

Clause 33. The method of any one of clauses 23-32, wherein one or more of the one or more ss-γPNA species has the structure:

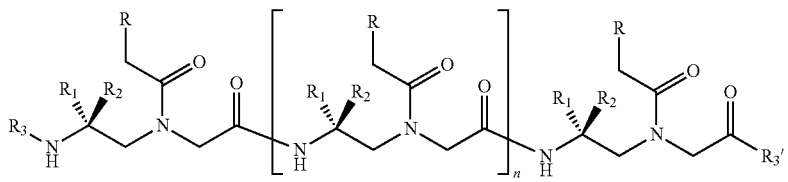

where,
each R is independently, a nucleobase;
n is 3 or more, 4 or more, 5 or more, or 6 or more, such as an integer ranging from 3 to 30 or from 10 to 30, for example, 6, 7, 8, 9, 10, 11, 12, 13, 14, 15, 16, 17, 18, 19, 20, 21, 22, 23, 24, 25, 26, 27, 28, 29, or 30;
each $R_1$ and $R_2$ are, independently: a guanidine-containing group, an amino acid side chain, methyl, ethyl, linear or branched $(C_3-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, each optionally substituted with a polyethylene glycol chain comprising from 1 to 50 units; H—$CH_2$—$(OCH_2$—$CH_2)_q OP_1$; —$CH_2$—$(OCH_2$—$CH_2)_q$—$NHP_1$; —$CH_2$—$(SCH_2$—$CH_2)_q$—$SP_1$; —$CH_2$—$(OCH_2$—$CH_2)_r$—OH; —$CH_2$—$(OCH_2$—$CH_2)_r$—$NH_2$; —$CH_2$—$(OCH_2$—$CH_2)_r$—$NHC(NH)NH_2$; or —$CH_2$—$(OCH_2$—$CH_2)_r$—S—S[$CH_2CH_2$]$_s NHC(NH)NH_2$, where $P_1$ is H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene or $(C_3-C_8)$cycloalkyl$(C_1-C_6)$alkylene; q is an integer from 0 to 50; r is an integer from 1 to 50, and s is an integer from 1 to 50;
$R_3$ is H or one or more natural or non-proteinogenic amino acids, a guanidine-containing group, a tag or a label; and
$R_3'$ is OH or one or more natural or non-proteinogenic amino acids, a guanidine-containing group, a tag or a label.

Clause 34. The method of any one of clauses 23-33, comprising mixing in the solvent a plurality of linearly-arranged contiguous strands comprising at least one of the one or more of the ss-γPNA species, and each of the contiguous strands comprising binding domains complementary to a biding domain on a different contiguous strand, forming a linear structure on hybridization of the complementary binding domains.

Clause 35. The method of clause 34, further comprising: mixing in the solvent two or more pluralities of contiguous strands comprising at least one of the one or more of the ss-γPNA species, and each of the contiguous strands comprising binding domains complementary to a binding domain on a different contiguous strand, producing two or more linear structures on hybridization of the complementary binding domains; and one or more crosslinking strands comprising at least one of the one or more of the ss-γPNA species that each bind complementary nucleobase sequences in two different linear structures formed from the pluralities of linearly-arranged contiguous strands, forming an ordered bundle of the linear structures on hybridization of the complementary binding domains.

Clause 36. The method of clause 35, comprising mixing in the solvent three pluralities of contiguous strands comprising at least one of the one or more of the ss-γPNA species, producing three linear structures on hybridization of the complementary binding domains; and three different crosslinking ss-γPNA strands, forming an ordered bundle of three linear structures on hybridization of the complementary binding domains.

Clause 37. The method of any one of clauses 23-36, further comprising mixing in the solvent a single-stranded nucleic acid or a nucleic acid analog, such as a single-stranded deoxyribonucleic acid or a peptide nucleic acid, having a binding domain complementary to a binding domain of one or more of the one or more ss-γPNA species.

Clause 38. The method of any one of clauses 23-37, wherein the complementary binding domains are less than 10 contiguous nucleobases each, such as from 3 to 8 contiguous nucleobases, such as 3, 4, 5, 6, 7, or 8 contiguous nucleobases.

Clause 39. The method of any one of clauses 23-38, wherein at least one of the one or more of the ss-γPNA species has at least 10%, from 10% to 50%, or from 20% to 40%, by number, γPNA residues.

Clause 40. The method of any one of clauses 23-39, wherein the solvent is a solvent that does not interfere with hydrogen-bonding donor/acceptor activity to the extent that it interferes with assembly and/or stability of the SST structure, such as a polar aprotic solvent or a polar aprotic organic solvent, such as dimethylsulfoxide (DMSO), dimethylformamide (DMF), or a combination thereof.

Clause 41. The method of clause 40, wherein the solvent comprises an anionic surfactant, such as sodium dodecyl sulfate (SDS), optionally below the critical micelle concentration of the surfactant in the solvent.

Clause 42. The method of any one of clauses 23-41, wherein one or more of the of one or more ss-γPNA species is less than 20, less than 19, less than 18, less than 17, less than 16, less than 15, less than 14, or less than 13 bases long.

Clause 43. The method of any one of clauses 23-42, wherein at least one of the one or more ss-γPNA method comprises: a guanidine-containing group, an amino acid side chain, and/or one or more contiguous natural or non-proteinogenicamino acid residues at either or both the C-terminal and/or N-terminal ends of the ss-γPNA.

Clause 44. The method of any one of clauses 23-43, wherein the one or more ss-γPNA species are complexed in the solvent by lowering the temperature of the solvent from a temperature at which no binding domains hybridize to a temperature at which all binding domains hybridize in the solvent, optionally at a rate of 0.1° C. per minute, or less.

Clause 45. The method of clause 43, wherein the temperature is lowered step-wise to hybridize different binding domain pairs in an order.

Clause 46. The method of any one of clauses 23-44, wherein the one or more ss-γPNA species are complexed in the solvent at a single temperature.

Clause 47. A nanoscale actuator comprising an SST structure according to any one of clauses 1-22 and a nucleic acid or nucleic acid analog able to hybridize with a binding domain of a strand of the SST structure and altering the structure of the SST structure.

Clause 48. A kit comprising an SST structure according to any one of clauses 1-22 and a nucleic acid or nucleic acid analog able to hybridize with a binding domain of a strand of the SST structure and altering the structure of the SST structure.

Clause 49. A method of modifying an SST structure, comprising contacting an SST structure comprising a PNA strand or of any one of clauses 1-22 with a nucleic acid or nucleic acid analog able to hybridize with a binding domain of a strand of the SST structure and altering the structure of the SST structure, and thereby changing the physical structure of the SST structure.

Clause 50. The method of clause 49, further comprising detecting a change in the physical structure of the SST structure from contacting the SST structure with the nucleic acid or nucleic acid analog able to hybridize with a binding domain of a strand of the SST structure and altering the structure of the SST structure.

Clause 50. A sensor system comprising an SST structure comprising a PNA strand or of any one of clauses 1-22 that is actuated by an analyte.

Clause 51. A kit comprising the sensor system of clause 50.

Clause 52. A method of sensing an analyte, comprising contacting the analyte with an SST structure comprising a PNA strand or of any one of clauses 1-22, that is actuated by the analyte, and detecting actuation of the SST structure by the analyte.

It should be noted that the structures made possible by the methods described herein are limited only by the imagination of a person of ordinary skill. While the examples, below, describe formation of essentially linear structures, such as nanotubes and nanotube bundles, different structures are made possible by the spatial configuration of the complementary binding domains on the various strands used to form the SST structure, and the choice of their sequences.

The SST structures are prepared in a solvent that does not interfere with hydrogen-bonding donor/acceptor activity to the extent that it interferes with assembly and/or stability of the SST structure, such as a polar aprotic solvent or a polar aprotic organic solvent, optionally in the presence of amounts of an anionic surfactant such as SDS, and optionally below the critical micelle concentration of the surfactant. Choice of solvent, surfactant, and concentrations thereof to optimize effects thereof for any given system may be determined empirically. Choice of modifications, and the degree of modification to the ss-γPNA strands, and, optionally and where present, other nucleic acids and nucleic acid analogs used to form an SST structure may be determined and optimized based on design constraints, and empirically. Further, the design of the SST structure and modifications of the constituents thereof may be chosen to permit changing of the solvent during or after formation (complexing) of SST structure from its constituents thereof, e.g., to optimize stability of the structure, or to permit an end use, e.g. as a sensor, or to allow for further chemical modification of the structure. For example, aqueous solubility may be encouraged by PEGylation or guanidine modification of γPNA residues.

Portions of, or the entire sequences of the ss-γPNA species described herein may be orthogonal to natural nucleic acids, such as RNA or DNA. By "orthogonal" it is meant that they do not hybridize to natural RNA or DNA sequences, or do not hybridize to natural RNA or DNA sequences to any significant extent in the context of the preparation and use of the compounds compositions, and methods described herein. This may be accomplished by use of an orthogonal nucleic acid analog backbone, such as left-handed γPNA, and/or by using orthogonal nucleobases. Both orthogonal nucleic acid analog backbones and orthogonal nucleobases may be used in one or more γPNA, nucleic acid, or nucleic acid analog strands forming the SST structures described herein.

As used herein, "protecting group" may refer to a moiety of a compound that masks or alters the properties of a functional group to which it bound, or the properties of the compound as a whole. Non-limiting examples of protecting groups include, but are not limited to, methyl, formyl, ethyl, acetyl, anisyl, benzyl, benzoyl, carbamate, trifluoroacetyl, diphenylmethyl, triphenylmethyl, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonyl, 9-fluorenylmethyloxycarbonyl, 2-nitrophenylsulfenyl, 2,2,5,7,8-pentamethyl-chroman-6-sulfonyl, N-succinimidyl, and p-bromobenzenesulfonyl.

As used herein, the term "nucleic acid" refers to deoxyribonucleic acids (DNA) and ribonucleic acids (RNA). Nucleic acid analogs include, for example and without limitation: 2'-O-methyl-substituted RNA, locked nucleic acids, unlocked nucleic acids, triazole-linked DNA, peptide nucleic acids including γPNA, morpholino oligomers, dideoxynucleotide oligomers, glycol nucleic acids, threose nucleic acids and combinations thereof including, but not limited to, ribonucleotide or deoxyribonucleotide residue(s). Herein, "nucleic acid" and "oligonucleotide," in reference to nucleic acids and nucleic acid analogs, are used interchangeably, and can refer to a short, single-stranded structure made of up nucleotides. An oligonucleotide may be referred to by the length (i.e. number of nucleotides) of the strand, through the nomenclature "-mer". For example, an oligonucleotide of 22 nucleotides would be referred to as a 22-mer.

A "nucleic acid analog" can be a composition comprising a sequence of nucleobases arranged on a substrate, such as a polymeric backbone, and can bind DNA and/or RNA by hybridization by Watson-Crick, or Watson-Crick-like hydrogen bond base pairing. Non-limiting examples of common nucleic acid analogs include peptide nucleic acids (PNAs), such as γPNA, morpholino nucleic acids, phosphorothioates, locked nucleic acid (2'-O-4'-C-methylene bridge, including, but not limited to, oxy, thio or amino versions thereof), unlocked nucleic acid (the C2'-C3' bond is cleaved), 2'-O-methyl-substituted RNA, threose nucleic acid, glycol nucleic acid, etc.

A conformationally preorganized nucleic acid analog can be a nucleic acid analog that has a backbone (a preorganized backbone) that forms either a right-handed helix or a left-handed helix, depending on the structure of the nucleic acid backbone. As shown herein, one example of a conformationally preorganized nucleic acid analog is γPNA, which has a chiral center at the γ carbon, and, depending on, and due to, the chirality of the groups at the γ carbon, forms a right-handed helix or a left-handed helix. Likewise, locked nucleic acids can comprise a ribose with a bridge between the 2' oxygen and the 4' carbon, which "locks" the ribose into a 3'-endo (North) conformation.

In the context of the present disclosure, a "nucleotide" may refer to a monomer comprising at least one nucleobase and a backbone element (backbone moiety), which in a nucleic acid, such as RNA or DNA, is ribose or deoxyribose. "Nucleotides" also typically comprise reactive groups that permit polymerization under specific conditions. In native DNA and RNA, those reactive groups are the 5' phosphate and 3' hydroxyl groups. For chemical synthesis of nucleic acids and analogs thereof, the bases and backbone monomers may contain modified groups, such as blocked or protected amines. A "nucleotide residue" may refer to a single nucleotide that is incorporated into an oligonucleotide or polynucleotide. Likewise, a "nucleobases residue" may refer to a nucleobases incorporated into a nucleotide or a nucleic acid or analog thereof. A nucleic acid or a nucleic acid analog may comprise a sequence of nucleobases, referred to herein as a binding domain, that is able to hybridize to (e.g., bind to) a complementary nucleic acid or nucleic acid analog sequence, e.g., a complementary binding domain or binding partner, on a nucleic acid by cooperative base pairing, e.g., Watson-Crick base pairing or Watson-Crick-like base pairing. Complementary binding domains may be referred to individually as binding partners, and together as a binding pair.

In further detail, nucleotides, for either RNA, DNA, or nucleic acid analogs, can have the structure A-B wherein A is a backbone monomer moiety and B is a nucleobase as described herein. The backbone monomer can be any suitable nucleic acid backbone monomer, such as a ribose triphosphate or deoxyribose triphosphate, or a monomer of a nucleic acid analog, such as peptide nucleic acid (PNA), such as a gamma PNA (γPNA). In one example the backbone monomer is a ribose mono-, di-, or tri-phosphate or a deoxyribose mono-, di-, or tri-phosphate, such as a 5' monophosphate, diphosphate, or triphosphate of ribose or deoxyribose. The backbone monomer can include both the structural "residue" component, such as the ribose in RNA, and any active groups that are modified in linking monomers together, such as the 5' triphosphate and 3' hydroxyl groups of a ribonucleotide, which are modified when polymerized into RNA to leave a phosphodiester linkage. Likewise for PNA, the C-terminal carboxyl and N-terminal amine active groups of the N-(2-aminoethyl)glycine backbone monomer can be condensed during polymerization to leave a peptide (amide) bond. In another aspect, the active groups are phosphoramidite groups useful for phosphoramidite oligomer synthesis. The nucleotide also optionally may comprise one or more protecting groups, such as 4,4'-dimethoxytrityl (DMT). A number of additional methods of preparing synthetic genetic recognition reagents depend on the backbone structure and particular chemistry of the base addition process. Determination of which active groups to utilize in joining nucleotide monomers and which groups to protect in the bases, and the required steps in preparation of oligomers is well within the abilities of those of ordinary skill in the chemical arts and in the field of nucleic acid and nucleic acid analog oligomer synthesis.

Figure 3:
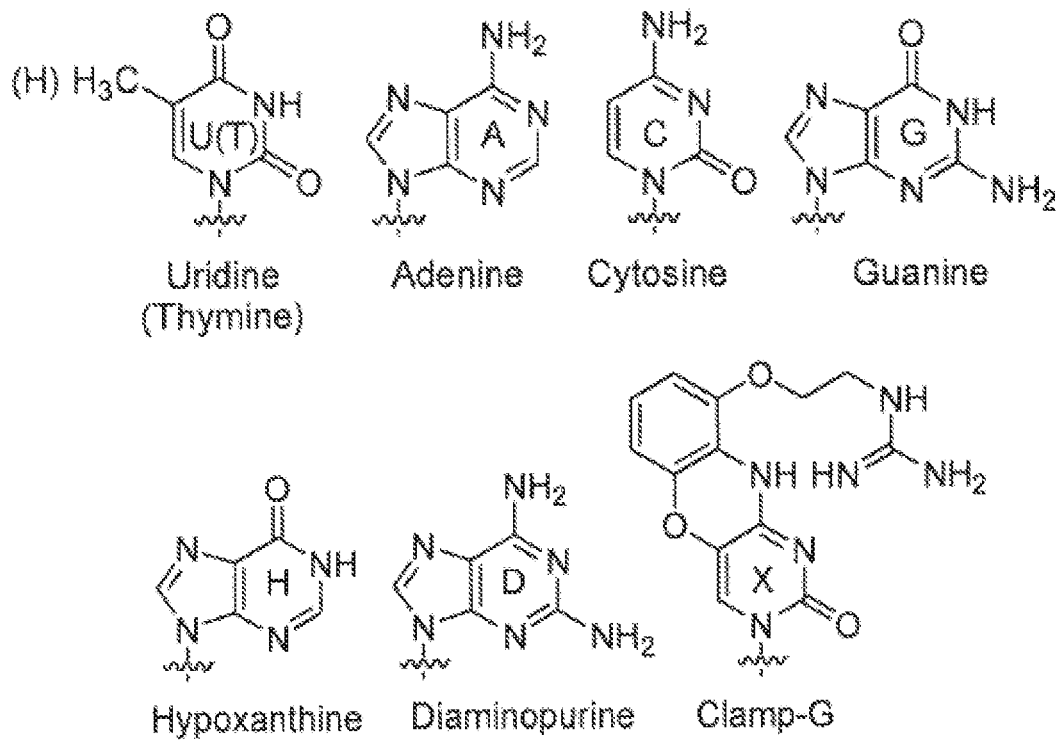
Figure 3:
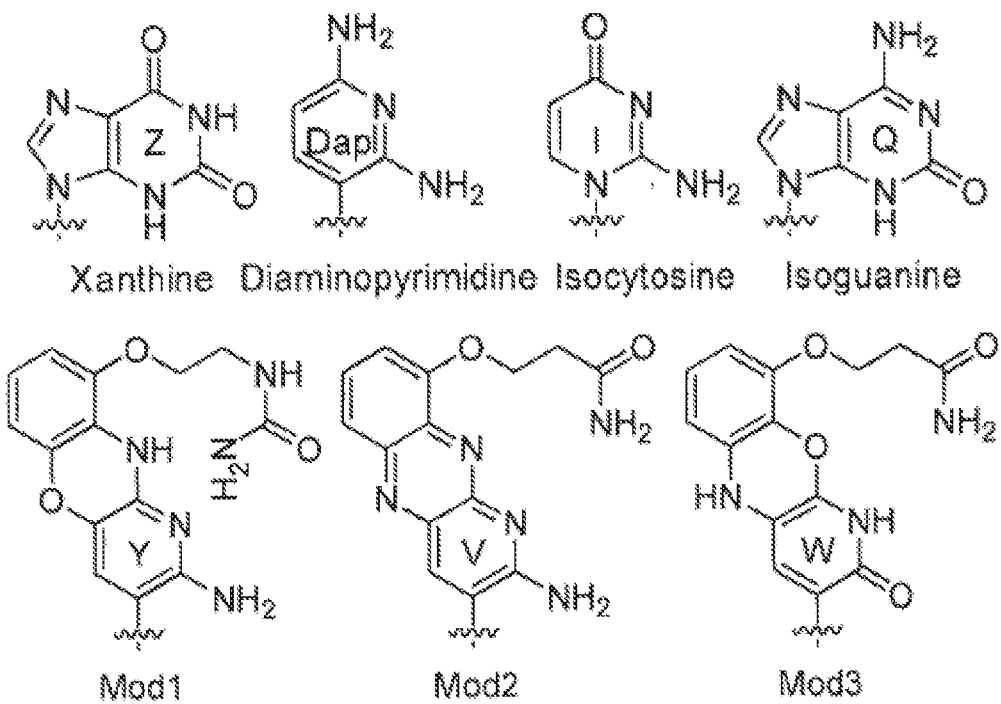
Figure 4B:
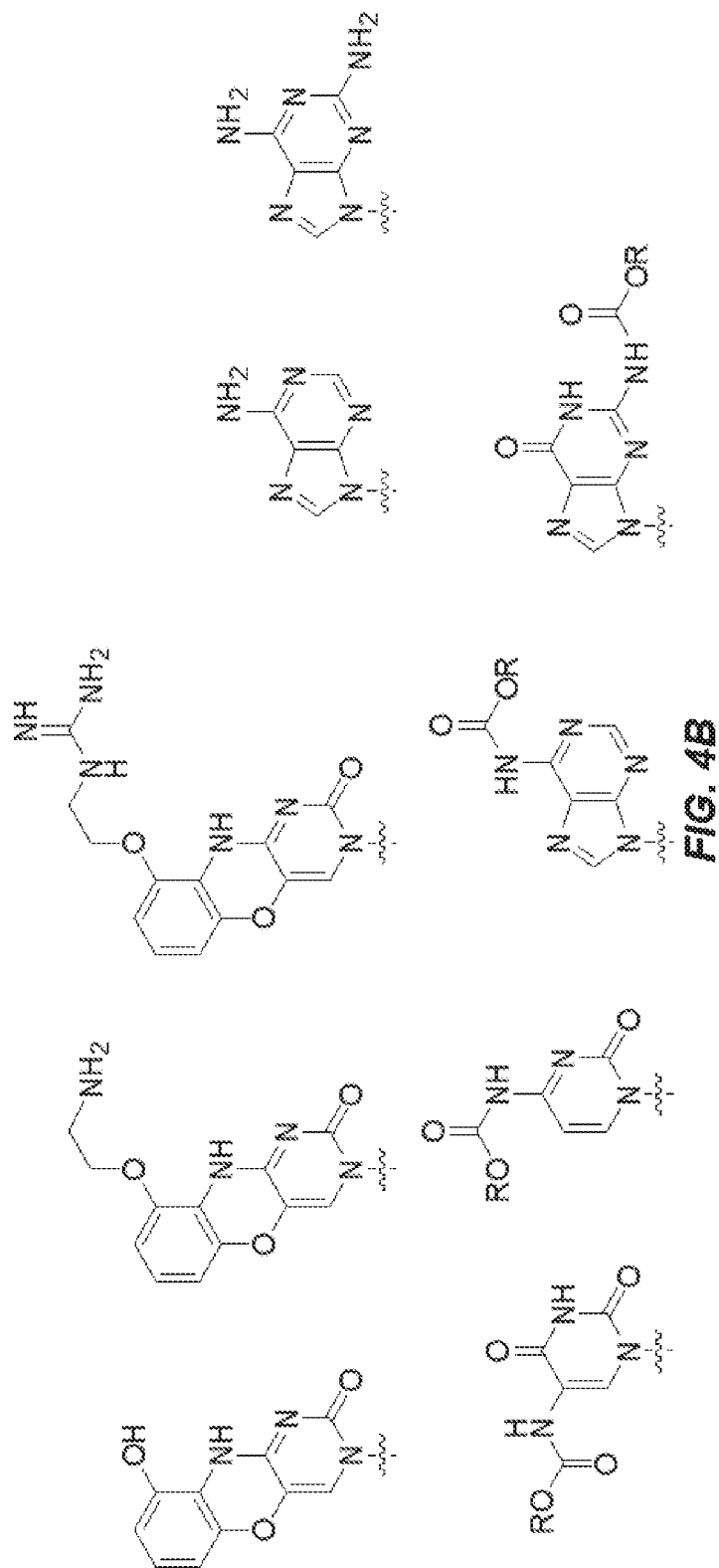
Figure 5A:
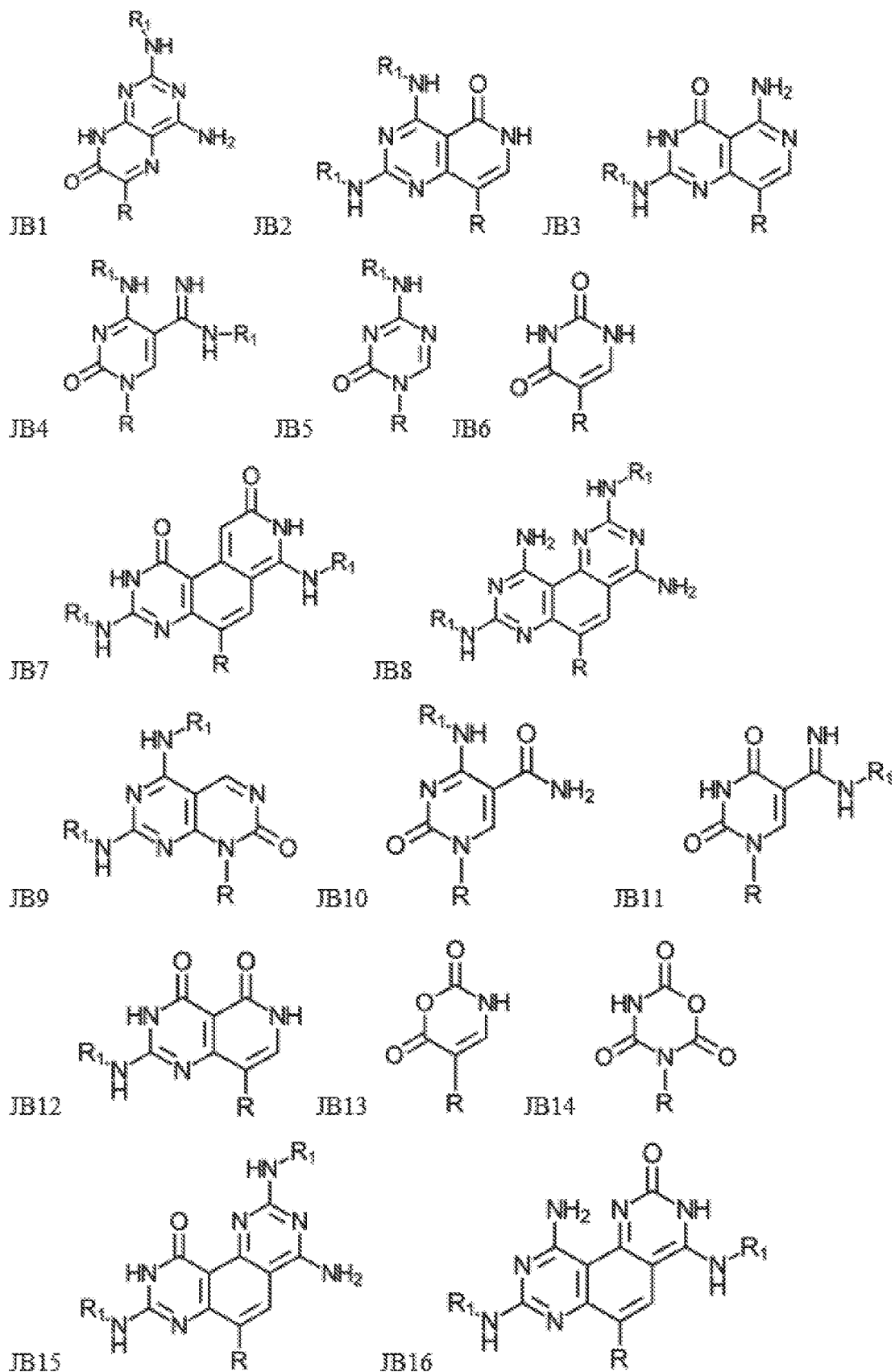
Figure 5B:
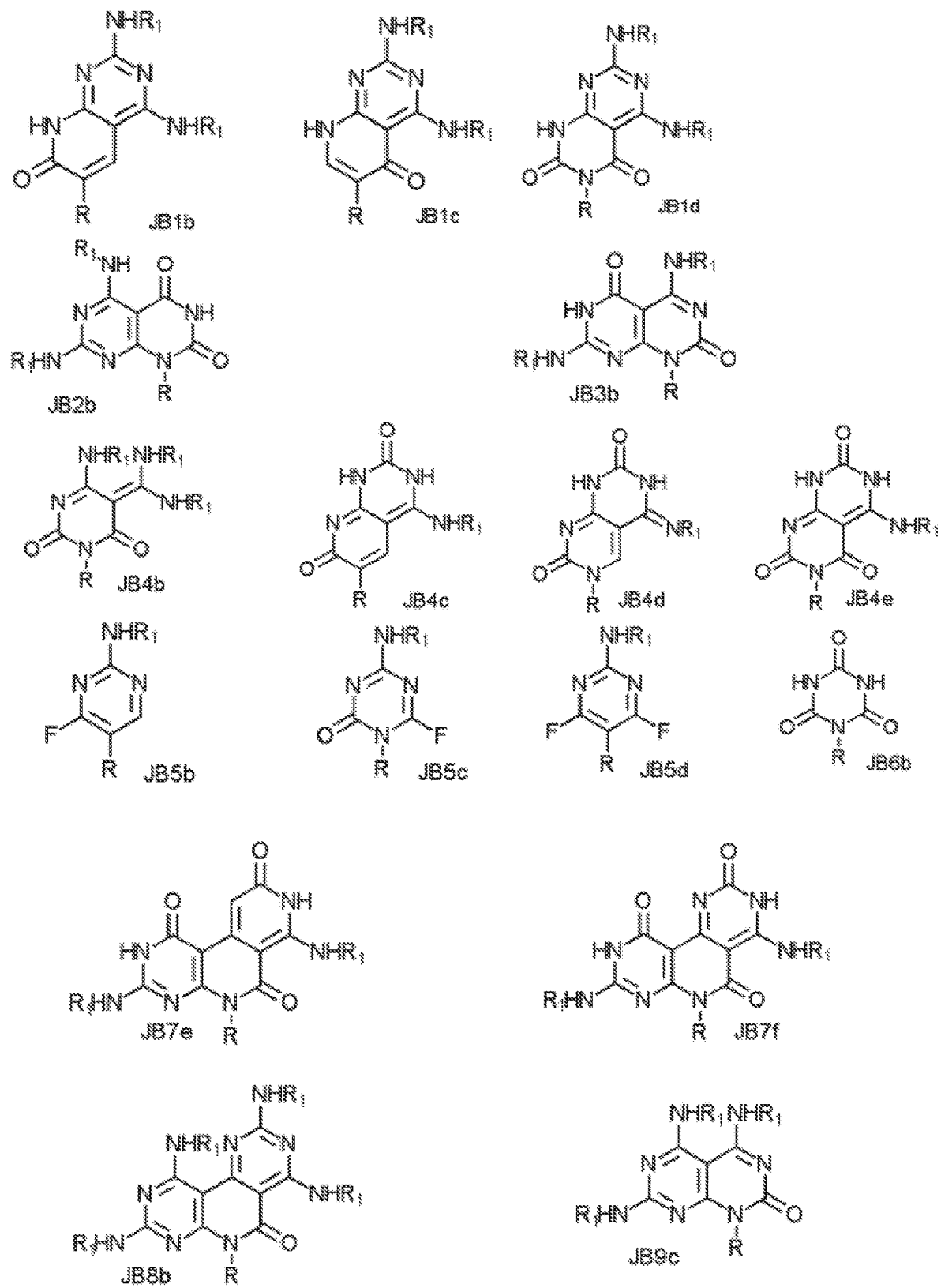
Figure 5C:
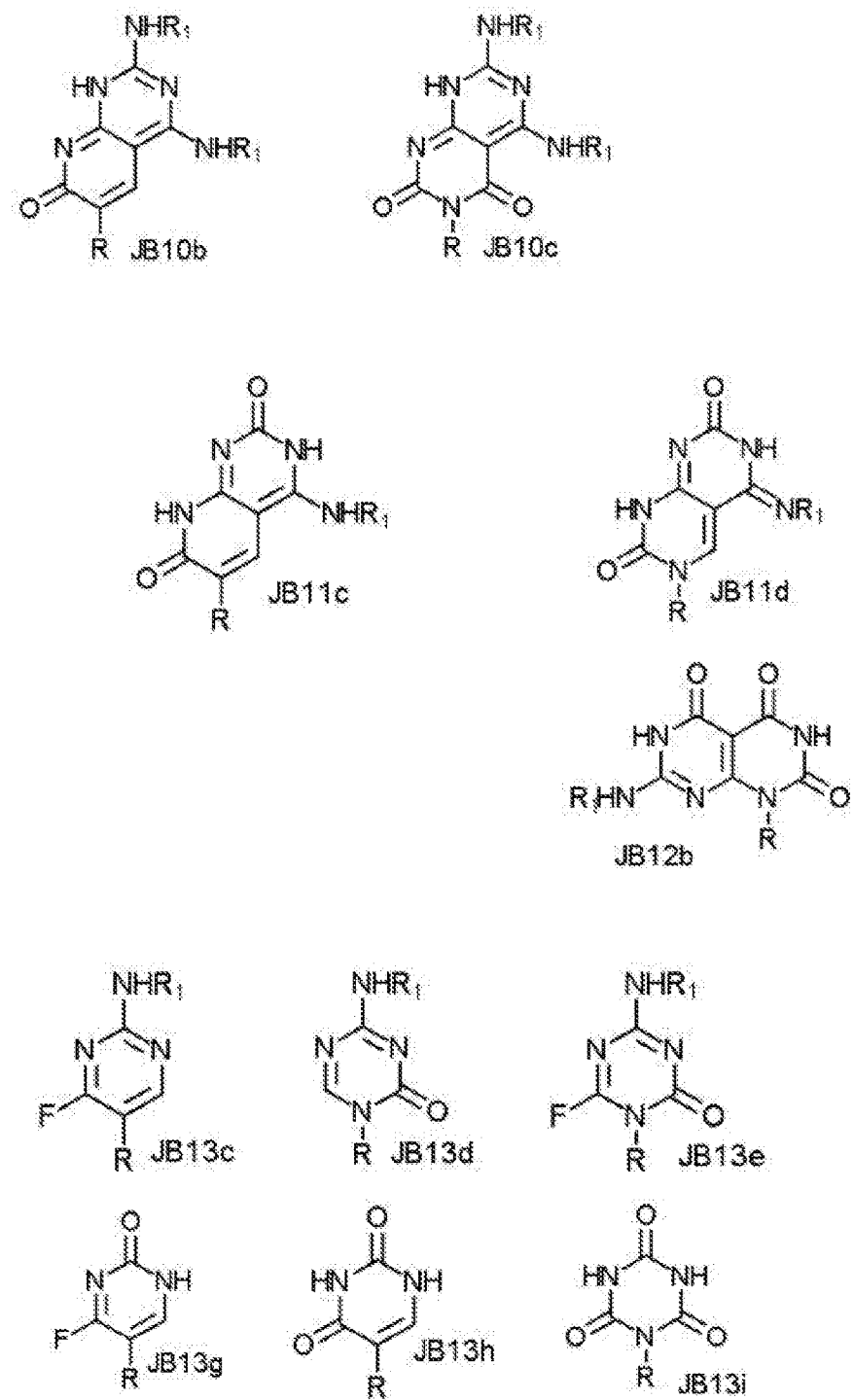

Non-limiting examples of common nucleic acid analogs include peptide nucleic acids, such as γPNA, phosphorothioate (e.g., FIG. 1 (A)), locked nucleic acid (2'-O-4'-C-methylene bridge, including, but not limited to, oxy, thio or amino versions thereof, e.g., FIG. 1 (B)), unlocked nucleic acid (the C2'-C3' bond is cleaved, e.g., FIG. 3 (C)), 2'-O-methyl-substituted RNA, morpholino nucleic acid (e.g., FIG. 1 (D)), threose nucleic acid (e.g., FIG. 3 (E)), glycol nucleic acid (e.g., FIG. 1 (F), showing R and S Forms), phosphorodiamidate morpholino oligomer (PMO). FIG. 1 (A-F) shows monomer structures for various examples of nucleic acid analogs. FIG. 1 (A-F) each show two monomer residues incorporated into a longer chain as indicated by the wavy lines. Incorporated monomers are referred to herein as "residues" and the part of the nucleic acid or nucleic acid analog excluding the nucleobases is referred to as the "backbone" of the nucleic acid or nucleic acid analog. As an example, for RNA, an exemplary nucleobase is adenine, a corresponding monomer is adenosine triphosphate, and the incorporated residue is an adenosine monophosphate residue. For RNA, the "backbone" consists of ribose subunits linked by phosphates, and, thus, the backbone monomer is ribose triphosphate prior to incorporation and a ribose monophosphate residue after incorporation. Like γPNA, Locked Nucleic Acid (e.g., FIG. 1 (B)) is conformationally preorganized.

A "moiety" is a part of a molecule, and can include as a class "residues", which are the portion of a compound or monomer that remains in a larger molecule, such as a polymer chain, after incorporation of that compound or monomer into the larger molecule, such as a nucleotide as-incorporated into a nucleic acid or an amino acid as-incorporated into a polypeptide or protein.

The term "polymer composition" may be a composition comprising one or more polymers. As a class, "polymers" can include, without limitation, homopolymers, heteropolymers, co-polymers, block polymers, block co-polymers and can be both natural and synthetic. Homopolymers contain one type of building block, or monomer, whereas co-polymers contain more than one type of monomer. An "oligomer" can be a polymer that comprises a small number of monomers, such as, for example, from 3 to 100 monomer residues. As such, the term "polymer" can include oligomers. The terms "nucleic acid" and "nucleic acid analog" can include nucleic acid and nucleic acid polymers and oligomers.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain linking groups are incorporated into the polymer backbone or certain groups are removed in the polymerization process. A polymer is said to comprise a specific type of linkage if that linkage is present in the polymer. An incorporated monomer can be a "residue". A typical monomer for a nucleic acid or nucleic acid analog is referred to as a nucleotide.

"Non-reactive", in the context of a chemical constituent, such as a molecule, compound, composition, group, moiety, ion, etc. can mean that the constituent does not chemically react with other chemical constituents in its intended use to any substantial extent. The non-reactive constituent is selected to not interfere, or to interfere insignificantly, with the intended use of the constituent, moiety, or group as a recognition reagent. In the context of linker moieties, the constituents can be non-reactive in that they do not interfere significantly with the binding of the strands in formation of an SST structure and/or the use thereof.

As used herein, "alkyl" refers to straight, branched chain, or cyclic hydrocarbon groups including, for example, from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_5O$ group that is substituted or unsubstituted. Non-limiting examples of straight alkyl groups include methyl, ethyl, propyl, butyl, pentyl, hexyl, heptyl, octyl, nonyl, and decyl. Branched alkyl groups comprises any straight alkyl group substituted with any number of alkyl groups. Non-limiting examples of branched alkyl groups include isopropyl, isobutyl, sec-butyl, and t-butyl. Non-limiting examples of cyclic alkyl groups include cyclopropyl, cyclobutyl, cyclopentyl, cyclohexyl, cycloheptlyl, and cyclooctyl groups. Cyclic alkyl groups also comprise fused-, bridged-, and spiro-bicycles and higher fused-, bridged-, and spiro-systems. A cyclic alkyl group can be substituted with any number of straight, branched, or cyclic alkyl groups. "Substituted alkyl" can include alkyl substituted at 1 or more (e.g., 1, 2, 3, 4, 5, or even 6) positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" can include divalent alkyl and divalent substituted alkyl, respectively, including, without limitation, methylene, ethylene, trimethylene, tetramethylene, pentamethylene, hexamethylene, hepamethylene, octamethylene, nona methylene, or decamethylene. "Optionally substituted alkylene" can include alkylene or substituted alkylene.

"Alkene or alkenyl" can include straight, branched chain, or cyclic hydrocarbyl (comprising only carbon and hydrogen) groups including, e.g., from 2 to about 20 carbon atoms, such as, without limitation $C_{2-3}$, $C_{2-6}$, $C_{2-10}$ groups having one or more, e.g., 1, 2, 3, 4, or 5, carbon-to-carbon double bonds. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. A halo-alkenyl group can be any alkenyl group substituted with any number of halogen atoms. "Substituted alkene" can include alkene substituted at 1 or more, e.g., 1, 2, 3, 4, or 5 positions, which substituents are attached at any available atom to produce a stable compound, with substitution as described herein. "Optionally substituted alkene" can include alkene or substituted alkene. Likewise, "alkenylene" can refer to divalent alkene. Examples of alkenylene include without limitation, ethenylene (—CH═CH—) and all stereoisomeric and conformational isomeric forms thereof "Substituted alkenylene" can refer to divalent substituted alkene. "Optionally substituted alkenylene" can refer to alkenylene or substituted alkenylene.

"Alkyne" or "alkynyl" refers to a straight chain, branched chain, or cyclic unsaturated hydrocarbon having the indicated number of carbon atoms and at least one triple bond. The triple bond of an alkyne or alkynyl group can be internal or terminal Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne.

An alkynyl group can be unsubstituted or optionally substituted with one or more substituents as described herein below. An alkyne or alkynyl group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. A halo-alkynyl group can be any alkynyl group substituted with any number of halogen atoms. The term "alkynylene" refers to divalent alkyne. Examples of alkynylene include without limitation, ethynylene, propynylene. "Substituted alkynylene" refers to divalent substituted alkyne.

The term "alkoxy" can refer to an —O-alkyl group having the indicated number of carbon atoms. An ether or an ether group comprises an alkoxy group. For example, a ($C_1$-$C_6$) alkoxy group includes —O-methyl (methoxy), —O-ethyl (ethoxy), —O-propyl (propoxy), —O— isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_1$-$C_{10}$)alkyl group wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$O H, —CH$_2$CH$_2$CH$_2$CH$_2$CH$_2$CH$_2$OH, and branched versions thereof. The term "ether" or "oxygen ether" refers to an alkyl group wherein one or more of the alkyl group's carbon atoms is replaced with an —O— group. The term ether can include —CH$_2$—(OCH$_2$—CH$_2$)$_q$OP$_1$ compounds where P$_1$ is a protecting group, —H, or a ($C_1$-$C_{10}$)alkyl. Exemplary ethers include polyethylene glycol, diethylether, methylhexyl ether and the like.

"PEG" refers to polyethylene glycol. "PEGylated" refers to a compound comprising a moiety, comprising two or more consecutive ethylene glycol moieties. Non-limiting examples of PEG moieties for PEGylation of a compound include, one or more blocks of a chain of from 1 to 50 ethylene glycol moieties, such as —(O—CH$_2$—CH$_2$)$_n$—, —(CH$_2$—CH$_2$—O)$_n$—, or —(O—CH$_2$—CH$_2$)$_n$—OH., where n ranges from 2 to 50.

"Heteroatom" refers to any atom other than carbon or hydrogen, for example, N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with any atom other than carbon or hydrogen, for example, N, O, P or S.

"Aryl," alone or in combination refers to an aromatic ring system such as phenyl or naphthyl. "Aryl" also can include aromatic ring systems that are optionally fused with a cycloalkyl ring. A "substituted aryl" is an aryl that is independently substituted with one or more substituents attached at any available atom to produce a stable compound, wherein the substituents are as described herein. The substituents can be, for example, hydrocarbyl groups, alkyl groups, alkoxy groups, and halogen atoms. "Optionally substituted aryl" refers to aryl or substituted aryl. An aryloxy group can be, for example, an oxygen atom substituted with any aryl group, such as phenoxy. An arylalkoxy group can be, for example, an oxygen atom substituted with any aralkyl group, such as benzyloxy. "Arylene" denotes divalent aryl, and "substituted arylene" refers to divalent substituted aryl. "Optionally substituted arylene" refers to arylene or substituted arylene. A "polycyclic aryl group" and related terms, such as "polycyclic aromatic group" refers to a group composed of at least two fused aromatic rings. "Heteroaryl" or "hetero-substituted aryl" refers to an aryl group substituted with one or more heteroatoms, such as N, O, P, and/or S.

"Cycloalkyl" refers to monocyclic, bicyclic, tricyclic, or polycyclic, 3- to 14-membered ring systems, which are either saturated, or partially unsaturated. The cycloalkyl group may be attached via any atom. Cycloalkyl also contemplates fused rings wherein the cycloalkyl is fused to an aryl or heteroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl. The term "optionally substituted cycloalkylene" refers to cycloalkylene that is substituted with at least 1, 2 or 3 substituents, attached at any available atom to produce a stable compound, wherein the substituents are as described herein.

"Carboxyl" or "carboxylic" refers to group having an indicated number of carbon atoms, where indicated, and terminating in a —C(O)OH group, thus having the structure —R—C(O)OH, where R is an unsubstituted or substituted divalent organic group that can include linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc.

"Amine" or "amino" refers to group having the indicated number of carbon atoms, where indicated, and terminating in a —$NH_2$ group, thus having the structure —R—$NH_2$, where R is a unsubstituted or substituted divalent organic group that, e.g. includes linear, branched, or cyclic hydrocarbons, and optionally comprises one or more heteroatoms. The term "alkylamino" refers to a radical of the formula —$NHR^x$ or —$NR^xR^x$ where each $R^x$ is, independently, an alkyl radical as defined above.

Terms combining the foregoing refer to any suitable combination of the foregoing, such as arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl. As an example, "arylalkylene" refers to a divalent alkylene wherein one or more hydrogen atoms in an alkylene group is replaced by an aryl group, such as a ($C_3$-$C_8$)aryl group. Examples of ($C_3$-$C_8$)aryl-($C_1$-$C_6$)alkylene groups include without limitation 1-phenylbutylene, phenyl-2-butylene, 1-phenyl-2-methylpropylene, phenylmethylene, phenylpropylene, and naphthylethylene. The term "($C_3$-$C_8$)cycloalkyl-($C_1$-$C_6$)alkylene" refers to a divalent alkylene wherein one or more hydrogen atoms in the $C_1$-$C_6$ alkylene group is replaced by a ($C_3$-$C_8$)cycloalkyl group. Examples of ($C_3$-$C_8$)cycloalkyl-($C_1$-$C_6$)alkylene groups include without limitation 1-cyclopropylbutylene, cyclopropyl-2-butylene, cyclopentyl-1-phenyl-2-methylpropylene, cyclobutylmethylene and cyclohexylpropylene.

Figure 2:
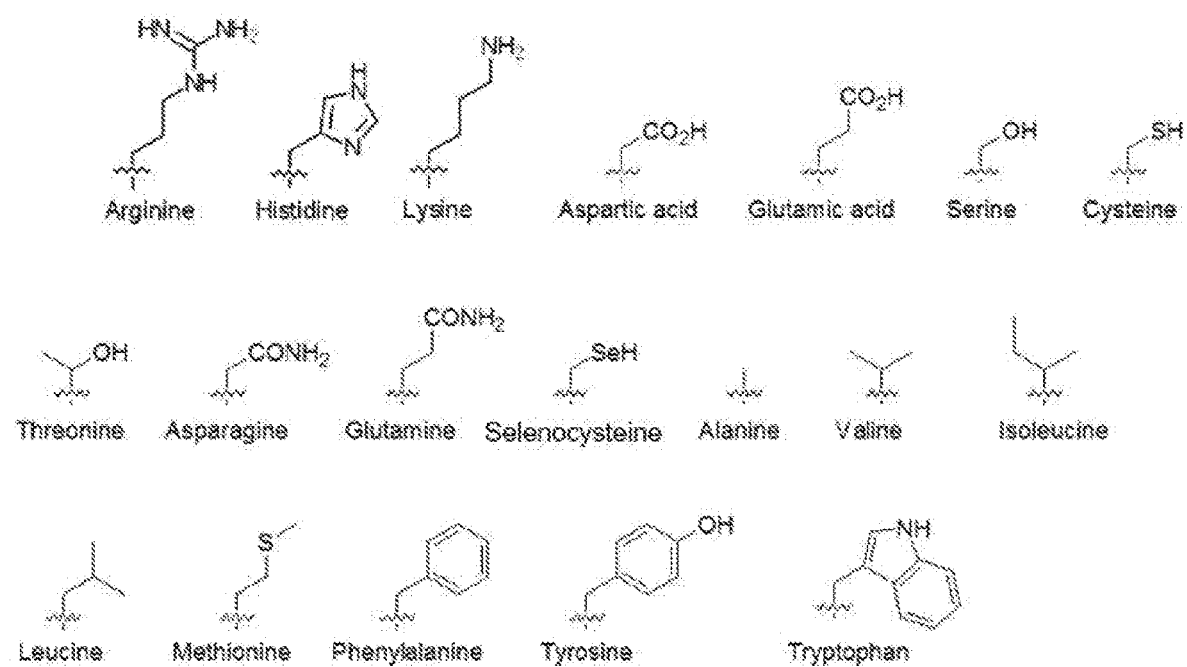
FIG. 2 provides structures of exemplary amino acid side chains.

An "amino acid" can include compounds that have the structure $H_2N$—C(R)—C(O)OH, where R is a side chain or H, such as an amino acid side chain. An "amino acid residue" represents the remainder of an amino acid when incorporated into a chain of amino acids, such as when incorporated into a recognition reagent as discloses herein, e.g., having the structures —NH—C(R)—C(O)—, $H_2N$—C(R)—C(O)— (when at the N-terminus of a polypeptide), or —NH—C(R)—C(O)OH (when at the C-terminus of a polypeptide). An "amino acid side chain" is a side chain for an amino acid, including, but not limited to, proteinogenic or non-proteinogenic amino acids. Non-limiting examples of amino acid side chains are shown in FIG. 2. Glycine ($H_2N$—$CH_2$—C(O)OH) has no side chain.

A non-proteinogenic amino acid includes naturally-occurring, or synthetic amino acids other than the natural, protienogenic amino acids (L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenyl alanine, L-proline, L-serine, L-threonine, L-tryptophan, L-tyrosine, L-valine, L-selenocysteine, L-and pyrrolysine). Non-proteinogenic amino acids may include D-amino acids. Non-limiting examples of non-proteinogenic amino acids may include naturally-occurring metabolic intermediates, such as ornithine, as well as synthetic amino acids, such as, without limitation: β-amino acids ($β^3$ and $β^2$), homo-amino acids, proline and pyruvic acid derivatives, 3-substituted alanine derivatives, glycine derivatives, ring-substituted phenylalanine and tyrosine derivatives, linear core amino acids, and N-methyl amino acids, among many others.

A "peptide nucleic acid" refers to a nucleic acid analog, or DNA or RNA mimic, in which the sugar phosphodiester backbone of the DNA or RNA is replaced by an N-(2-aminoethyl)glycine unit. A gamma PNA (γPNA) is an oligomer or polymer of gamma-modified N-(2-aminoethyl) glycine monomers of the following structure:

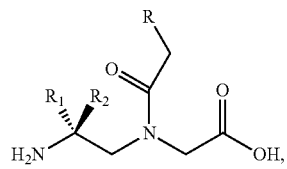

where R is a nucleobase moiety, and at least one of $R_1$ or $R_2$ attached to the gamma carbon is not a hydrogen, such that the gamma carbon is a chiral center. When $R_1$ and $R_2$ are hydrogen (N-(2-aminoethyl)-glycine backbone), or the same, there is no such chirality about the gamma carbon. Where $R_2$ is hydrogen, and $R_1$ is not, the γPNA is said to be left-handed. Where $R_1$ is hydrogen, and $R_2$ is not, the γPNA is said to be right-handed. Right-handed PNA is able to hybridize in a Watson-Crick or Watson-Crick-like manner with complementary single-stranded DNA or RNA. In some cases where neither $R_1$ nor $R_2$ are hydrogen but $R_1$ and $R_2$ are different, the handedness of the residue or oligomer may be dictated by the respective bulkiness of the $R_1$ and $R_2$ groups, or by other physical or chemical properties of the groups, and the chirality may be designated right-handed where the configuration hybridizes to complementary DNA or RNA strands, but the opposite configuration does not.

$R_1$ and $R_2$ may include, but are not limited to, any one of the following function groups:

(1) Amino acid sidechains (Ala, —CH$_3$; Val, —CH(CH$_3$)$_2$; Ile, —CH(CH$_3$)CH$_2$CH$_3$; Leu, —CH$_2$CH(CH$_3$)$_2$; Met, —CH$_2$CH$_2$SCH$_3$; Phe, —CH$_2$C$_6$H$_5$; Tyr, —CH$_2$C$_6$H$_4$OH; Trp, —CH$_2$C$_{8-15}$NH; Ser, —CH$_2$OH; HSer, —CH$_2$CH$_2$OH; Thr, —CHCH$_3$OH; Asn, —CH$_2$CONH$_2$; Gln, —CH$_2$CH$_2$CONH$_2$; Cys, —CHSH; Sec, —CH$_2$SeH; Gly, —H; Pro, —(CH$_2$)$_3$—; Arg, —(CH$_2$)$_3$NHC(NH)NH$_2$; His, —CH$_2$C$_3$H$_3$N$_2$; Lys, —(CH$_2$)$_4$NH$_2$; Asp, —CH$_2$CO$_2$H; and Glu, —(CH$_2$)$_2$CO$_2$H).

(2) Linear or branched (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene, (C$_3$-C$_8$)cycloalkyl(C$_1$-C$_6$)alkylene, —CH$_2$—(OCH$_2$—CH$_2$)$_q$OH, —CH$_2$—(OCH$_2$—CH$_2$)$_q$—NH$_2$, —CH$_2$—(OCH$_2$—CH$_2$)$_q$—NHC(NH)NH$_2$, —CH$_2$—(OCH$_2$—CH$_2$—O)$_q$—SH and —CH$_2$—(SCH$_2$—CH$_2$)$_q$—SH, —(CH$_2$CH$_2$)$_q$—NHC(NH)NH$_2$, where subscript q is an integer between 0-25.

An incorporated PNA or γPNA monomer,

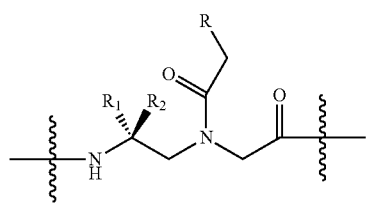

is referred to herein as a PNA or γPNA "residue", in reference to the remaining structure after integration into an oligomer or polymer, with each residue having the same or different R group as its base (nucleobase), such as adenine, guanine, cytosine, thymine and uracil bases, or other bases, such as the monovalent and divalent bases described herein, such that the order of bases on the PNA is its "sequence", as with DNA or RNA. A sequence of nucleobases in a nucleic acid or a nucleic acid analog oligomer or polymer, such as a PNA or γPNA oligomer or polymers, binds to a complementary sequence of adenine, guanine, cytosine, thymine and/or uracil residues in a nucleic acid or nucleic acid analog strand by nucleobase pairing, in a Watson-Crick or Watson-Crick-like manner, essentially as with double-stranded DNA or RNA.

A "guanidine" or "guanidinium" group may be added to the recognition reagent to increase solubility and/or bioavailability. Because PNA is produced in a similar manner to synthetic peptides, a simple way to add guanidine groups is to add one or more terminal arginine (Arg) residues to the N-terminal and/or C-terminal ends of the PNA, e.g., γPNA, recognition reagent. Likewise, an arginine side group,

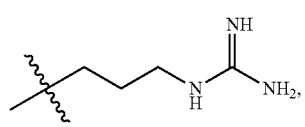

or a guanidine-containing moiety, such as

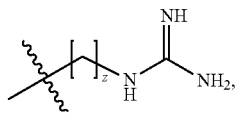

where z, for example and without limitation, ranges from 1-5, or a salt thereof, can be attached to a recognition reagent backbone as described herein. A guanidine-containing group is a group comprising a guanidine moiety, and may have less than 100 atoms, less than 50 atoms, e.g., less than 30 atoms. In one aspect, the guanidine-containing group has the structure:

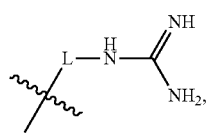

where L is a non-reactive linker, e.g., a non-reactive aliphatic hydrocarbyl linker, such as a methylene, ethylene, trimethylene, tetramethylene, or pentamethylene linker. The guanidine-containing group may have the structure:

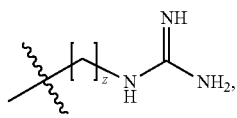

where z is 1-5, e.g., the guanidine group may be an arginine side group.

A "nucleobase" can include primary nucleobases: adenine, guanine, thymine, cytosine, and uracil, as well as modified, non-natural, purine and pyrimidine bases, such as, without limitation, hypoxanthine, xanthene, 7-methylguanine, 5, 6, dihydrouracil, 5-methylcytosine, and 5-hydroxymethylcytosine. FIGS. 3, 4A, 4B, and 5A-5C also depict non-limiting examples of nucleobases, including, but not limited to, monovalent nucleobases (e.g., adenine, cytosine, guanine, thymine or uracil, which bind to one strand of nucleic acid or nucleic acid analogs), and divalent nucleobases (e.g., JB1-JB16 described herein) which bind complementary nucleobases on two strands of DNA simultaneously, and "clamp" nucleobases, such as a "G-clamp," which binds complementary nucleobases with enhanced strength. Additional purine, purine-like, pyrimidine and pyrimidine-like nucleobases are disclosed, for example in U.S. Pat. Nos. 8,053,212, 8,389,703, and 8,653,254. For divalent nucleobases JB1-JB16, shown in FIG. 5A, Table A shows the specificity of the different nucleobases. Of note, JB1-JB4 series bind complementary bases (C-G, G-C, A-T and T-A), while JB5-JB16 bind mismatches, and, thus, can be used to bind two strands of matched and/or mismatched bases. Divalent nucleobases are described in further detail in United States Patent Application Publication No. 2016/0083434 A1 and International Patent Publication No. WO 2018/058091, both of which are incorporated herein by reference.

TABLE A

Divalent Nucleobases

| Nucleobase | Bases represented |
|---|---|
| JB1 | T/D* |
| JB2 | D/T |
| JB3 | G/C |
| JB4 | C/G |
| JB5 | C/C |
| JB6 | U/U |
| JB7 | G/G |
| JB8 | D/D |
| JB9/JB9b | A/C |
| JB10 | C/A |
| JB11 | U/G |
| JB12 | G/U |
| JB13 | C/U |
| JB14 | U/C |
| JB15 | G/D |
| JB16 | D/G |

*diaminopurine, an adenine analog.

Exemplary γPNA structures are disclosed in International Patent Publication No. WO 2012/138955, incorporated herein by reference. The γPNA may be left-handed PNA, which is orthogonal to natural RNA and DNA.

Complementary refers to the ability of polynucleotides (nucleic acids) to hybridize to one another, forming interstrand base pairs. Base pairs are formed by hydrogen bonding between nucleotide units in polynucleotide or polynucleotide analog strands that are typically in antiparallel orientation. Complementary polynucleotide strands can base pair (hybridize) in the Watson-Crick manner (e.g., A to T, A to U, C to G), or in any other manner that allows for the formation of duplexes. In RNA as opposed to DNA, uracil rather than thymine is the base that is complementary to adenosine. Two sequences, e.g., binding domains as described herein, comprising complementary sequences can hybridize if they form duplexes under specified conditions, such as in water, saline (e.g., normal saline, or 0.9% w/v saline) or phosphate-buffered saline), in a polar aprotic solvent or polar aprotic organic solvent, such as DMSO and/or DMF, optionally in the presence of an anionic surfactant, as described herein, or under other stringency conditions, such as, for example and without limitation, 0.1× SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be "fully complementary", though one sequence (e.g., a target sequence in an mRNA) may be longer than the other, as in the case of the small recognition reagents described herein in relation to the much longer target sequences on which they concatenate, such as mRNAs containing repeat expansions.

Of note, γPNA does not require a minimum of 10 complementary bases to bind strongly in the context of SST structure assembly and stability. Depending on the choice of nucleobase, γPNA may only need 3, 4, 5, 6, 7, 8, or 9 consecutive complementary based to form adequately stable duplexes for purposes herein. As shown herein binding domains of six nucleobases are able to form robust structures.

All nucleotide sequences are provided in a 5' to 3' direction, left to right, unless indicated otherwise.

A moiety in a compound, such as a nucleobase, is covalently attached to the recognition domain backbone, and thus is said to be "linked" to the backbone. Depending on the chemistry used to prepare the compound, the linkage may be direct, or through a "linker" which is a moiety that covalently attaches two other moieties or groups. The linker may be a non-reactive moiety that links the aromatic group to the backbone of the recognition reagent, and, in some aspects includes from 5-25 carbon atoms ($C_1$-$C_{10}$), optionally substituted with a hetero-atom, such as a N, S, or O, or a non-reactive linkage, such as an amide linkage (peptide bond) formed by reacting an amine with a carboxyl group. Examples of $C_1$-$C_{10}$ alkylenes include linear or branched, alkylene (bivalent) moieties such as a methylene, ethylene, trimethylene, tetramethylene, pentamethylene, hexamethylene, hepamethylene, octamethylene, nonamethylene, or decamethylene moiety (e.g., —$CH_2$—[$CH_2$]$_n$—, where n=1 to 9), optionally comprising an amide linkage and optionally comprising a cyclic moiety. The linkers may comprise from one to four ethylene oxide (e.g., —O—$CH_2$—$CH_2$— or —$CH_2$—$CH_2$—O—) moieties. The linkers are non-bulky in that they do not sterically hinder or otherwise interfere to any substantial extent with the formation of an SST structure. The linker, when incorporated into a compound is the remaining moiety or residue resulting from the linking.

A linker or linking group may be an organic moiety that connects two parts of a compound, e.g., covalently attaches two parts of a compound, such as, for example and without limitation, connection of the aromatic groups to the backbone of the recognition reagent, connection of a nucleobase to the nucleic acid or nucleic acid analog backbone, and/or connection of a guanidium group to the recognition reagent. Linkers typically comprise a direct bond or an atom such as oxygen, nitrogen, phosphorus, or sulfur, a unit such as, C(O), C(O)NH, SO, $SO_2$, $SO_2$NH, or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, in which one or more carbons, e.g., methylenes or methylidynes (—CH═) is optionally interrupted or terminated by a hetero atom, such as O, S, or N, substituted or unsubstituted aryl, substituted or unsubstituted heteroaryl, substituted or unsubstituted heterocyclic. In one aspect, the linker may comprise or consist of between about 5 to 25 atoms, e.g., 5-20, 5-10, e.g., 5, 6, 7, 8, 9, 10, 11, 12, 13, 14, 15, 16, 17, 18, 19, or 20 atoms, or a total of from 1 to 10, e.g., 1, 2, 3, 4, 5, 6, 7, 8, 9, or 10 C and heteroatoms, e.g., O, P, N, or S atoms. The linker may have a molecular weight, based on the atomic mass of its constituent atoms, of less than 500 Daltons (Da) or less than 400 Da.

For linkage to a PNA, such as a γPNA, an expedient and available linker may be one that reacts an amine with a carboxyl group to form an amide linkage, e.g., using peptide synthesis chemistries to add amino acids to the recognition reagent, where amino acids, such as arginine, may be pre-modified with a chemical moiety, such as a left-handed γPNA, or a guanidine group. Linking to non-peptide nucleic acid analogs can be achieved using any suitable linking chemistry, such as by using carbodiimide chemistry.

A compound or single-stranded gamma peptide nucleic acid (ss-γPNA) may be provided. The composition may comprise a PNA backbone, and thus has a structure exemplified by:

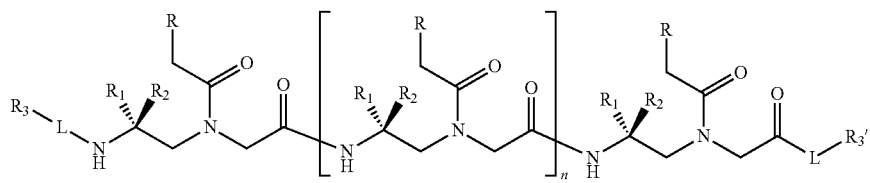

where, each R is independently, nucleobases;
n is an integer ranging from 1 and 6, such as 1, 2, 3, 4, 5, or 6;
each L is independently, linkers;
each $R_1$ and $R_2$ may be, independently: a guanidine-containing group such as

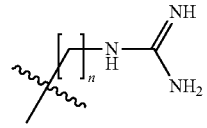

where n=1, 2, 3, 4, or 5; an amino acid side chain, such as:

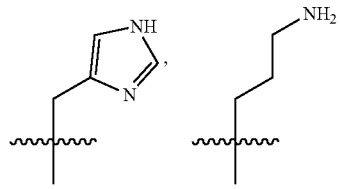

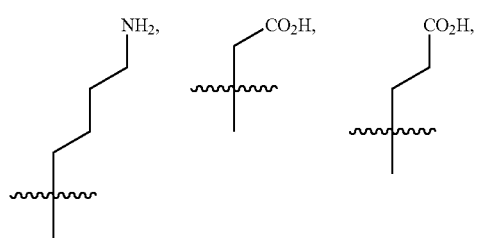

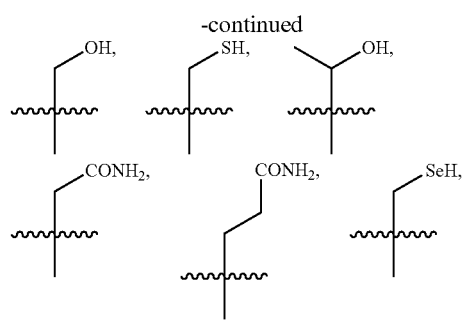

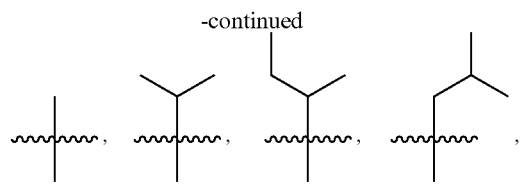

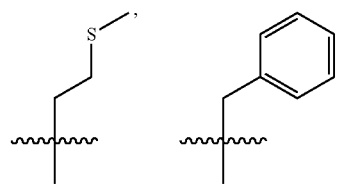

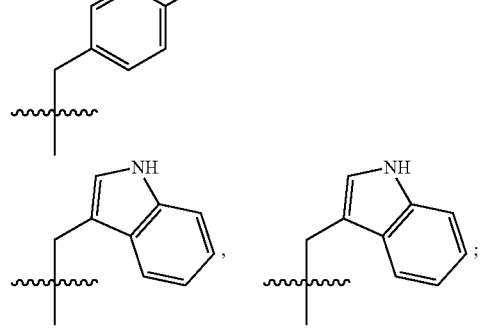

methyl, ethyl, linear or branched $(C_3-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, each optionally substituted with a polyethylene glycol chain of 1 to 50 units; H, —$CH_2$—$(OCH_2—CH_2)_q OP_1$; —$CH_2$—$(OCH_2—CH_2)_q$—$NHP_1$; —$CH_2$—$(SCH_2—CH_2)_q$— $SP_1$; —$CH_2$—$(OCH_2—CH_2)_r$—OH; —$CH_2$—$(OCH_2—CH_2)_r$—$NH_2$; —$CH_2$—$(OCH_2—CH_2)_r$—$NHC(NH)NH_2$; or —$CH_2$—$(OCH_2—CH_2)_r$—S—$S[CH_2CH_2]_s NHC(NH)NH_2$, where $P_1$ is H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene or $(C_3-C_8)$cycloalkyl$(C_1-C_6)$alkylene; q is an integer from 0 to 50; r is an integer from 1 to 50, and s is an integer from 1 to 50;

where, for γPNA $R_1$ and $R_2$ are different, $R_1$ is H and $R_2$ is not H, $R_2$ is H and $R_1$ is not H, or $R_2$ is not H and $R_1$ is not H but is different than $R_2$ so as to form a chiral center at the γ carbon. For binding to natural nucleic acids, such as RNA or DNA, $R_1$ is H and $R_2$ is not H, thereby forming "right-handed" L-γPNA. "Left-handed" D-γPNA, in which $R_2$ is H and $R_1$ is not H, does not bind natural nucleic acids; and $R_3$ and $R_3'$ are terminal groups, such as H, a guanidine-containing group, a tag, a dye or fluorophore, one or more consecutive amino acids, such as arginine or lysine, or a detectable or capturable moiety, such as, for example and without limitation, a cyanine dye, a his tag, or biotin.

Each instance of L is, independently, a linker, and may comprise one or more amino acid residues, or substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, in which one or more carbons, e.g., methylenes or methylidynes (—CH=) is optionally interrupted or terminated by a hetero atom, such as O, S, or N, substituted or unsubstituted aryl, substituted or unsubstituted heteroaryl, substituted or unsubstituted heterocyclic, and optionally comprises a guanidine-containing group such as

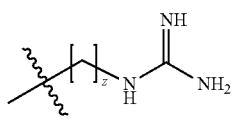

where z=1, 2, 3, 4, or 5, and/or an amino acid side chain.

Each L is optional and may comprise or consist of between about 5 to 25 atoms, e.g., 5-20, 5-10, e.g., 5, 6, 7, 8, 9, 10, 11, 12, 13, 14, 15, 16, 17, 18, 19, or 20 atoms, or a total of from 1 to 10, e.g., 1, 2, 3, 4, 5, 6, 7, 8, 9, or 10 C and heteroatoms, e.g., O, P, N, or S atoms. In one aspect, $R_1$ or $R_2$ may be ($C_1$-$C_6$)alkyl substituted with —(OCH$_2$—CH$_2$)$_q$OP$_1$; —(OCH$_2$—CH$_2$)$_q$—NHP$_1$; —(SCH$_2$—CH$_2$)$_q$—SP$_1$; —(OCH$_2$—CH$_2$)$_r$—OH; —(OCH$_2$—CH$_2$)$_r$—NH$_2$; —(OCH$_2$—CH$_2$)$_r$—NHC(NH)NH$_2$; or —(OCH$_2$—CH$_2$)$_r$—S—S[CH$_2$CH$_2$]$_s$NHC(NH)NH$_2$, where $P_1$ is H, ($C_1$-$C_8$) alkyl, ($C_2$-$C_8$)alkenyl, ($C_2$-$C_8$)alkynyl, ($C_3$-$C_8$)aryl, ($C_3$-$C_8$) cycloalkyl, ($C_3$-$C_8$)aryl($C_1$-$C_6$)alkylene or ($C_3$-$C_8$)cycloalkyl($C_1$-$C_6$)alkylene; q is an integer from 0 to 50; r is an integer from 1 to 50, and s is an integer from 1 to 50.

Unless otherwise indicated, the γPNAs, nucleic acids, and nucleic acid analogs described herein are not described with respect to any particular sequence of nucleobases. The present disclosure is directed to SST structures and methods and compositions for use in preparing SST structures, and is independent of the identity and sequence of bases attached thereto. Any nucleobase sequence attached to the backbone of the described γPNA oligomers can hybridize in a specific manner with a complementary nucleobases sequence of a target nucleic acid or nucleic acid analog by Watson-Crick or Watson-Crick-like hydrogen bonding. The compositions and methods described herein are sequence-independent and describe a novel, generalized method, and related compositions, for SST production.

Nucleobases of the binding domains described herein are arranged in a sequence complementary to target sequences of other binding domains, so that binding domains as described herein bind by base pairing, e.g., by Watson-Crick, or Watson-Crick-like base pairing.

Provided herein are single-stranded tile (SST) structures formed from the hybridization of ss-γPNA species comprising binding domains that interconnect the ss-γPNA molecules into a defined or ordered structure, such as a structure having a periodic structure comprising two or more repeats of a specific structural motif formed from the binding of one or more ss-γPNA molecules in a particular arrangement, optionally in combination with one or more nucleic acids or nucleic acid analogs in addition to the ss-γPNA molecules. By SST, it is meant, without limitation, a repeated organization of nucleic acid or nucleic acid analog strands, such as PNA and γPNA strands, and should not be construed as limiting to any particular structure or structure design or organization. The arrangement of the ss-γPNA molecules may be dictated by one or more nucleobase sequences each forming a binding domain on the ss-γPNA molecule that binds or hybridizes as a member of a binding pair with a complementary nucleobase sequence forming a binding domain on a different ss-γPNA molecule. Complementary binding domains form a binding pair. Although they may be longer, each ss-γPNA binding domain may be from 3 to 9, e.g., 3, 4, 5, 6, 7, 8, or 9 bases in length, typically having 100% sequence identity with its complementary binding partner. "Species" in the context of ss-γPNAs used to produce an SST refers to identical nucleic acids and nucleic acid analogs, such as ss-γPNA molecules having the same sequence and structure. As such, more than one nucleic acid species may be used to produce SST structures.

The binding partners may be on a single γPNA strand, allowing the same strand to concatenate to form a linear, double-stranded nanostructure. More typically, and to facilitate more complex SST structures, members of binding domain pairs are located on different nucleic acid or nucleic acid analog species that form an SST structure. Each species of nucleic acid or nucleic acid analog, such as ss-γPNA, used to produce the SST structure may include one, two, three, four, or more binding domains, dependent on the desired SST structure to be formed. For example, two or more different species, such as ss-γPNA species, may be configured with suitable binding domains to form a nanotube of those species. Ss-γPNA species, and more broadly, nucleic acid and nucleic acid analog species, that form the body of a contiguous structure, such as a linear, sheet, or tube structure, may be referred to as contiguous strands. Ss-γPNA species, and more broadly, nucleic acid and nucleic acid analog species, that link two or more contiguous structures, such as a linear, sheet, or tube structure, may be referred to as cross-linking strands. Binding domains may be included in a contiguous strand, with its binding partners included in a crosslinking strand to direct specific arrangement of multiple contiguous structures, such as, for example to form an ordered bundle of tubes, as shown in the Examples below, where, for example, three nanotubes, each formed from two different contiguous strand ss-γPNA species (six total ss-γPNA species), are crosslinked and thereby bundled by three crosslinking strand ss-γPNA species.

The SST may be formed from a combination of ss-γPNA species and one or more nucleic acid species or nucleic acid analog species, which confer different properties to the SST structure. For example a contiguous strand in a nanotube SST structure may comprise a ss-γPNA molecule and a ss-DNA molecule, e.g., as in the example, below. Of note, LH-γPNA does not bind natural nucleic acid, and, as such, may not be used to bind DNA or RNA in an SST structure. As indicated elsewhere, PNA binds both left-handed and right-handed γPNA as well as nucleic acids and most nucleic acid analogs. RH-γPNA does not bind LH-γPNA, but binds PNA, nucleic acids, and typical nucleic acid analogs. This "handedness" can be exploited to assist in designing complex SST structures. An ss-γPNA molecule or species may comprise only LH-γPNA residues, only RH-γPNA residues, or two or more, e.g., three, four, or five, binding domains, with both LH-γPNA and RH-γPNA binding domains included on the same ss-γPNA molecule.

The SST structures may be prepared in a polar aprotic solvent, such as DMSO, DMF, or a mixture thereof. A surfactant, such as an anionic surfactant, may be added to the polar aprotic solvent, which may improve structural uniformity and stability. The SST structures are prepared by mixing the precursors, that is the nucleic acid or nucleic acid analog species, including at least one ss-γPNA species, in appropriate stoichiometric ratios with the solvent, and complexing the precursors to form the SST structure. Addition of the precursors to the solvent may be enough to form a desired the SST structure. It may be that each precursor is already stored in a suitable solvent prior to mixing and complexing, such as a solvent used to produce the precursor. The precursors may be added in an organized, step-wise manner to first form intermediate structures, and later to form higher-complexity structures. The precursors may be mixed together and maintained at any temperature or series of temperatures useful to make an SST structure therefrom. The precursors may be maintained at a single temperature to form the SST structure. The solvent containing the precursors may be heated to a temperature above which the precursors do not bind, such as a temperature above the Tm of one or more, or all, binding domain pairs in the mixture, followed by cooling the mixture to a temperature at which the precursors bind, such as a temperature below the Tm of one or more, or all, binding domain pairs in the mixture. The temperature may be lowered in a step-wise fashion to allow for partial binding of certain precursors before binding of other precursors. Certain precursors may be added at one time point, and others at a second time point, optionally combined with manipulation of the temperature as described to order the assembly of the SST structure. Additional reagents, such as solvents, surfactants, emulsifiers, lipids, water and salts, etc. may be included in the mixture, or added to the mixture to further manipulate and facilitate a desired SST structure assembly scheme.

Surfactants are amphiphiles typically comprising a hydrophilic head and a hydrophobic or lipophilic tail. Their tails often are hydrocarbyl. The heads of anionic surfactants are negatively-charged, such as, without limitation, sulfate, sulfonate, phosphate, and carboxylates. Non-limiting examples of anionic surfactants include alkyl sulfates, such as sodium dodecyl sulfate (SDS) and sodium laureth sulfate. Other useful anionic surfactants may include: sodium decyl sulfate, sodium N-lauroyl N-methyltaurate, sodium tetradecyl sulfate Solvents useful in assembly of the SST structures described herein are solvents that permit assembly of the structures by hybridization of the recognition domains of the ss-γPNA strands, and, when present, other nucleic acid or nucleic acid analog strands. As such, useful solvents may include a solvent that does not interfere with hydrogen-bonding donor/acceptor activity to the extent that it interferes with assembly and/or stability of the SST structure. Such solvents may be a polar aprotic solvent or a polar aprotic organic solvent. Polar aprotic solvents are solvents that lack an acidic hydrogen and therefore are not hydrogen bond donors, examples of which include, without limitation: dimethylsulfoxide (DMSO), dimethylformamide (DMF), hexamethylphosphoramide (HMPA, which not organic), dichloromethane, N-methylpyrrolidone, tetrahydrofuran, acetonitrile, propylene carbonate, pyridine, and ethyl acetate, including combinations of two or more of any of the preceding. Other useful solvents may include: dimethylacetamide, valerolactone, 2,5-dimethyltetrahydrofuran.

Critical micelle concentration (CMC) may refer to the concentration of surfactants in a solution above which micelles form and all additional surfactants added to the system or liquid mixture incorporate into micelles. The CMC may be dependent upon the specific surfactant(s) used in a liquid mixture and the solvents.

The SST structures described herein may be provided in the solvent in which they are formed. The solvent of the mixture in which the SST structure was formed may be exchanged by any suitable method with a different solvent using suitable exchange methods, such as partitioning or binding to a surface by affinity via tags or binding partners, such as biotin, incorporated into the structure. So long as the SST structure is maintained or modified into a desired form, any suitable solvent or exchange method may be used. Tags and labels, such as a polyhistidine tag, biotin, or a fluorochrome, among others as may be known and/or commercially-available, e.g. in a labeling kit, is a moiety attached to a compound such as a polypeptide, a nucleic acid, or a nucleic acid analog that may facilitate, for example and without limitation, purification, capture, binding, separation, or identification of the tag-modified reagent.

A nanoscale actuator is provided, comprising an SST structure as described herein and a nucleic acid or nucleic acid analog able to hybridize with a binding domain of a strand of the SST structure and altering the structure of the SST structure. The nucleic acid or analog thereof, such as an ss-γPNA, may displace (invade) a bound binding domain strand forming the SST structure, or may hybridize to an unbound binding domain partner in the SST structure. By "actuator" it is meant a structure that changes its shape or size, or another physical parameter, wherein actuation refers to the action of causing a machine or device to operate. An actuator may be a sensor that senses the presence of the nucleic acid or nucleic acid analog able to hybridize with a binding domain of a strand of the SST structure and altering the structure of the SST structure. The binding or displacement of a strand of the SST structure by the nucleic acid or nucleic acid analog able to hybridize with a binding domain of a strand of the SST structure and altering the structure of the SST structure, may be detected in a sensor system by any suitable method, such as, without limitation, microscopy, electrophoresis, fluorescence, or mechanically, e.g., by physical action of the actuator. The actuator may form part of a mechanical device in which actuation of the actuator results in a mechanical force applied to another structure. In one example, the SST is in the form of a ring, and coiling of the ring, and therefore the dimensions of the ring is altered on actuation.

The compositions, structures and methods described herein offer the following features:
- A novel design that accommodates special properties of PNA. For example, the length of binding segments can be tuned to alter melting temperature, improve yields, and improve stability. Short PNA strands with 6-base overlap segments have been demonstrated. In addition, the nanostructure design accounts for the helical twist of PNA, which at 18-20 bases per turn, is much less twisted than DNA which has 10.5 bases per turn. Similar to single-stranded tile approach used in DNA origami, but substantially different.
- Demonstration of 3-helix nanotube and 2-helix nanoribbon, and design approach that can be extended to nanotubes consisting of larger numbers of helices. Approach could also be used to form straight tubes, twisted tubes, and ring nanostructures.
- Demonstration of design-appropriate mini peg functionalization of gamma-PNAs that is compatible with the nanotube design and enables proper formation of designed structure.
- A novel synthesis protocol including solutions and anneal ramps for forming these nanostructures.

EXAMPLES

Responsive and programmable nucleic acid-based materials have the potential to revolutionize fields including biophysics, diagnostics, therapeutics, photonics, and nanofabrication. The sub-nanometer precision in self-assembly enabled by structural DNA nanotechnology, however has been limited to aqueous or substantially hydrated media. Reduced water activity or transfer to organic solvents commonly used in polymer and peptide synthesis, typically results in the alteration of DNA helical structure or reduced thermal stabilities. Here we demonstrate a structural nucleic acid nanotechnology that enables formation of solvent-compatible, self-assembling nanostructures defined by Watson-Crick base pairing. In selecting polar aprotic solvents, e.g., polar aprotic organic solvents, we find that gamma-modified peptide nucleic acids (γPNAs) can form micron-scale filaments. Unlike the diameter-monodisperse populations of nanotubes formed using analogous DNA approaches, γPNA structures appear to form bundles of nanotubes. A tight distribution of the nanotube diameters may be achieved in the presence of the surfactant SDS during self-assembly. Further, the morphologies of these γPNA structures can be tuned by means of solvent solution and by strand substitution with DNA and unmodified PNA. This work introduces a science of γPNA nanotechnology, which permits nanofabrication and nanosensing in harsh environments.

Modification at the gamma position of N-(2-aminoethyl) glycine backbone of PNA causes the single-stranded molecule to assume a pre-organized helical arrangement. This molecule is called γPNA, and it can bind to DNA and RNA with exceptionally high affinity and sequence selectivity. While the development of γPNA was largely aimed at improving anti-sense therapies and molecular diagnostics, we hypothesized that the resulting higher binding affinity due to the pre-organized helical arrangement of (R)-diethylene glycol (mini-PEG) containing γPNA would enable it to be used for the formation of complex nucleic acid nanostructures in organic solvent mixtures.

Example 1

Complementary PNA binds more strongly to DNA than DNA does to its own complement and PNA-DNA duplexes have more bases per turn than DNA-DNA duplexes. This difference is expected to cause PNA invasion to apply torque to untwist DNA. (FIG. 6 (a)). Described herein is a system and method that measure supercoiling of DNA nanorings to quantify the induced twist caused by strand invasion with PNA and γPNA. The PNA strand invasion is expected to induce twist in nanorings, and PNA with larger densities of γ modifications are expected to induce greater twist and thus compensatory writhe in a closed ring structure.

Figure 6:
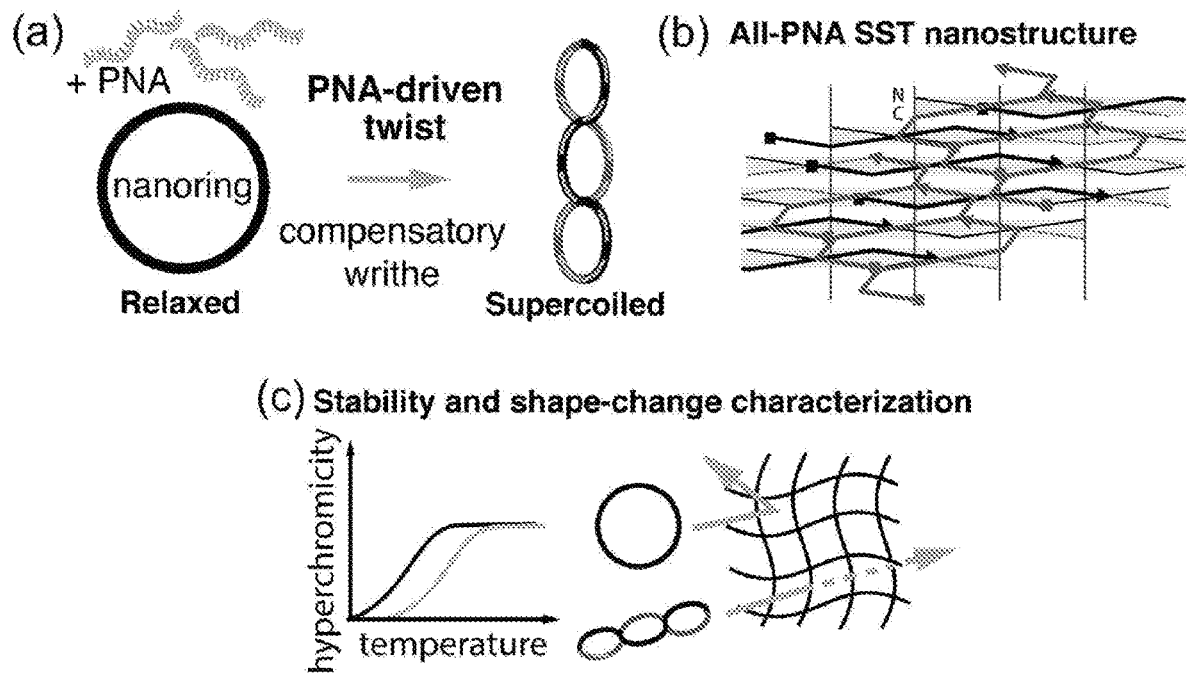
FIG. 6 provides a summary of the method described in Example 1.
Figure 7:
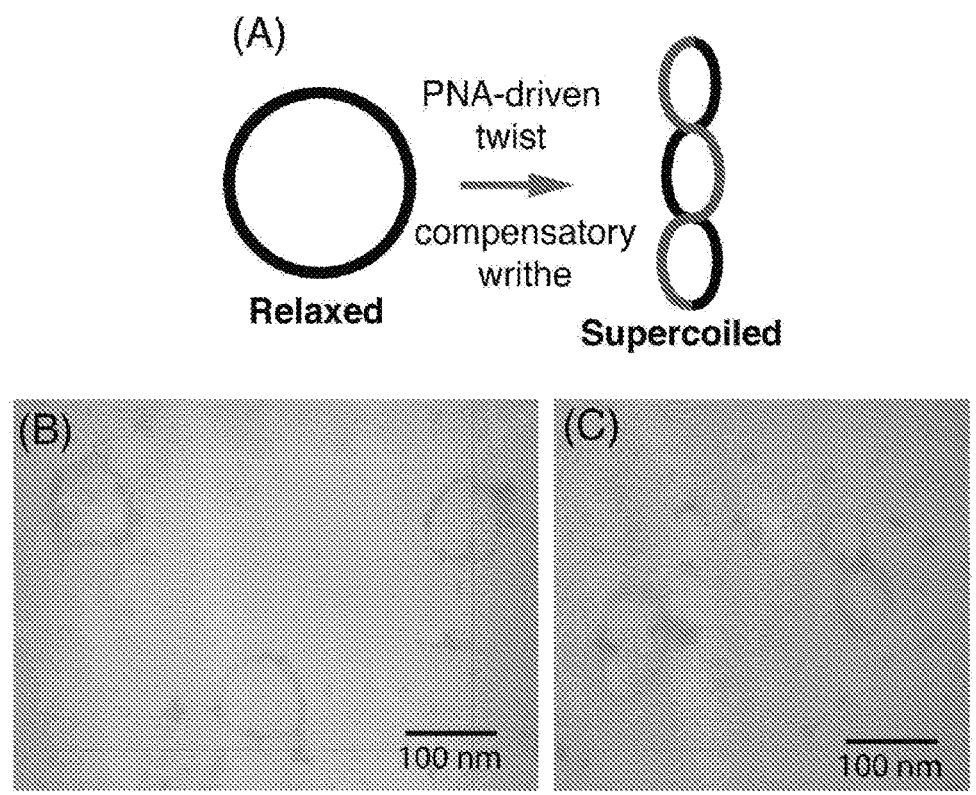
FIG. 7: Coiling and nanoring constructs (A) PNA strand invasion impalts twist and resulting writhe for supercoiling. (B) As shown in TEM images, we have synthesized with 86 nm diameters. (C) Initial strand invasion studies with single PNA invasion sites few twisted rings, and we will aim to increase the yield of twisted segments using increased numbers of PNA invasion sites and γPNA.

The system and method are also based on the rationale that PNA-PNA duplexes have higher melting temperatures and more bases per turn than DNA-DNA duplexes, but the general conceptual approach for designing DNA SST systems can remain the same (FIG. 6 (b)). Described system and method design and synthesize all-PNA SST systems with minimal components. Analogous designs for all-PNA SSTs can be based on existing SST approaches, but due to higher stability of PNA-PNA duplexes, PNA SST sub-segment lengths should be shorter than existing DNA SST sub-segments while the number of bases per turn must be higher for all-PNA designs.

The system and method is further based on the rationale that PNA-PNA duplexes are known to be more salt-insensitive, more thermally stable, and more flexible than DNA-DNA duplexes. So PNA systems should be more stable and their inherent flexibility could allow for larger or directional twisting effects by strand invasion by torsional stiffened, chiral γPNA. The application further characterize stability, shape distribution, effective shape change due to strand invasion by left- and right-handed γPNA for both all-DNA and all-PNA nanorings. All-PNA nanorings are expected to be more flexible in torsion, more temperature and salt-resistant than DNA nanorings, and resulting shape distributions and effective shape change may vary from DNA nanorings. Handedness of γPNA may enable handed twisting.

We take advantage of the difference between DNA and PNA in terms of bases per turn to achieve this. PNA-PNA duplexes have on average 18 bases per turn, and owing to the flexibility (low torsional stiffness) of PNA, PNA-DNA duplexes have about 13 bases per turn, much closer to period of DNA duplexes than PNA duplexes. γPNA is less flexible (more torsionally stiff) than standard PNA, so γPNA-DNA duplexes have 15 bases per turn. We predict that strand invasion by PNA and γPNA can induce untwisting of DNA and may therefore be used to apply internal torsion to DNA nanostructures without applying substantial axial loads on the system.

To aid in the quantification of twist, we may study the twist and resultant writhe in Yang-style nanorings upon strand invasion by PNA and γPNA. Closed geometries obey topological supercoiling rules wherein twist (Tw) and writhe (Wr) sum to an invariant, the linking number (Lk).

$$L_k = T_w + W_r \tag{1}$$

Since $L_k$ is fixed, if internal twist is decreased by strand invasion, the positive writhe is expected occur; more untwisting will lead to more writhe. Writhe in nanorings will be visualized via TEM and also captured via increases in mobility in gel electrophoresis experiments. With the nanoring designs shown, each nanoring has a diameter of approximately 86 nm, which equates to 250 nm in circumference and about 37 repeating segments each 7.14 nm in length. We can use an energy balance to derive an expression for the expected twist in a six-helix bundle induced by the strand invasion of a single PNA strand. We assume that the moment applied to untwist a single PNA-DNA tube from 10.5 bases/turn to 13 bases/turn is the same moment that applied to a six-helix bundle structure. For small angles, the twist angle formula states that the angle of untwist in a DNA-DNA tube can be calculated as follows:

$$\phi_{helix} = \frac{T_{invasion}L}{G_{DNA}J_{helix}} \quad (2)$$

where T is the applied torque, G is the shear modulus (modulus of rigidity for DNA and PNA), J is the polar moment of ineltia of a single helix, and L is the length of a repeating segment. This torque due to strand invasion will deform the six-helix bundle and the expression for that deformation is as follow:

$$\phi_{bundle} = \frac{nT_{invasion}L}{G_{bundle}J_{bundle}} \quad (3)$$

where n is the number of invasion sites per bundle segment, $G_{bundle}$ is the weighted average of helical stiffness and $J_{bundle}$ is the polar moment inertia of the six-helix bundle:

$$G_{bundle} = \tfrac{5}{6}G_{DNA} + \tfrac{1}{6}G_{PNA} \quad (4).$$

We can use the parallel axis theorem to calculate the polar moment of inertia of the six-helix bundle by assuming that each helix is offset a single diameter, D (2 nm), from the central axis of the nanotube:

$$J_{bundle} = 6*\left(J_{helix} + \frac{\pi D^4}{4}\right). \quad (5)$$

We can solve equations (2) and (3) for $T_{invasion}$ and equate them:

$$T_{invasion} = \frac{G_{bundle}J_{bundle}\phi_{bundle}}{nL} = \frac{G_{DNA}J_{helix}\phi_{helix}}{L}. \quad (6)$$

Simplifying and solving for the twist of the bundle we get the following:

$$\phi_{bundle} = \frac{nG_{DNA}J_{helix}\phi_{helix}}{G_{bundle}J_{bundle}}. \quad (7)$$

Further assume the simple case that $G_{DNA}$ equals $G_{PNA}$, $G_{bundle}$ simplifies to $G_{DNA}$ and cancels out of the expression for bundle twist:

$$\phi_{bundlesimple} = \frac{nJ_{helix}\phi_{helix}}{6*\left(J_{helix} + \frac{\pi D^4}{4}\right)}. \quad (8)$$

Simply increasing n, the number of invasions per bundle is the easiest way to increase twist. We can assume that $J_{helix}$, the rotational moment of area of each helix, is fixed since even with strand invasion we don't expect large changes in double helical cross-sectional area or shape. The angle of twist induced in a single helix is dependent on the type of PNA and we can estimate them to be as follows:

$$\phi_{helixPNA} = (360°)\frac{(13 - 10.5 \text{ bases})}{10.5 \text{ bases}} = 85.7° \text{ rotation} \quad (9)$$

$$\phi_{helix\gamma PNA} = (360°)\frac{(15 - 10.5 \text{ bases})}{10.5 \text{ bases}} = 154.3° \text{ rotation.} \quad (10)$$

If the effective stiffness of the bundle does not change with PNA or γPNA invasion, we predict that invasion by γPNA will induce nearly twice the twist of standard PNA invasion. However, invasion by a stiffer γPNA strand should yield a slightly stiffer overall bundle with an invading PNA strand, so this estimate is likely an upper limit of expected rotation. For now we will assume that the bundle stiffness is approximately fixed.

To increase twist ($\Phi_{bundlesimple}$) we can test increasing numbers of strand-invasion sites (n), and we can also use γPNA instead of PNA. Since DNA-PNA is typically more flexible than DNA-DNA, the above estimate is likely an overestimate. In order to improve twist, γPNA, which is pre-organized and more torsionally stiff, can be used to increase applied twist. If we need to account for changes in bundle stiffness, we assume complete strand invasion, and then be able to extract the relative stiffness of each DNA-PNA and DNA-γPNA duplex from the equation (7). Finally, equation (7) tells us that decreasing the polar moment of inertia of the bundle will increase the bundle twist. And we can consider designing and fabricating four-helix bundles instead of six-helix bundles since the four-helix bundles will have a smaller polar moment of inertia. However, the bundle size also effects the attainable diameters and thus number of repeat units for the Yang-style nanorings. Table B summarizes the predicted twist in different rings for invasion by PNA and γPNA.

TABLE B

Predicted nanoring twist by bundle type, invasion strand, and number of insertions per segment

| Bundles | Diameter [nm] | # Segs | Invasion Strand | Helix Tw [degrees] | Tw/seg/n [degrees] | Tw (n = 1) [degrees] | Tw (n = 2) [degrees] |
| --- | --- | --- | --- | --- | --- | --- | --- |
| 4 helix (+2/−2) | 52.6 +/− 0.21 | 23.1 | PNA | 85.7 | 7.14 | 165.3 | 330.6 |
| 4 helix (+1/−1) | 81.3 +/− 0.31 | 35.8 | PNA | 85.7 | 7.14 | 255.5 | 511.0 |
| 6 helix (+2/−2) | 84.8 +/− 0.18 | 37.3 | PNA | 85.7 | 1.59 | 59.2 | 118.5 |
| 6 helix (+1/−1) | 165.5 +/− 0.25 | 72.8 | PNA | 85.7 | 1.59 | 115.6 | 231.2 |
| 4 helix (+2/−2) | 52.6 +/− 0.21 | 23.1 | γPNA | 154.3 | 12.86 | 297.6 | 595.1 |
| 4 helix (+1/−1) | 81.3 +/− 0.31 | 35.8 | γPNA | 154.3 | 12.86 | 459.9 | 919.8 |

TABLE B-continued

Predicted nanoring twist by bundle type, invasion strand, and number of insertions per segment

| Bundles | Diameter [nm] | # Segs | Invasion Strand | Helix Tw [degrees] | Tw/seg/n [degrees] | Tw (n = 1) [degrees] | Tw (n = 2) [degrees] |
|---|---|---|---|---|---|---|---|
| 6 helix (+2/−2) | 84.8 +/− 0.18 | 37.3 | γPNA | 154.3 | 2.86 | 106.6 | 213.2 |
| 6 helix (+1/−1) | 165.5 +/− 0.25 | 72.8 | γPNA | 154.3 | 2.86 | 208.1 | 416.1 |

We would expect four-helix bundles to twist up to ⅔ of turn per invasion site whereas six-helix bundles twist up to ⅓ of a turn per PNA invasion site and nearly twice that for γPNA. We may investigate both four- and six-helix bundles, varying invasion strand type (PNA and γPNA) and varying the number of invasion sites per bundle segment. This work is further supported by our finding that for a subsection of a Yang-style nanoring, PNA is indeed able to invade the particular DNA duplex structure in the nanorings. We measured the melting temperature of a DNA subsection of a six-helix nanoring. For a subsection of the nanoring construct, melting studies were performed before and after strand invasion by a 9-base PNA strand. While the initial all-DNA construct has a melting temperature of 36° C., after PNA strand invasion the melting temperature was increased more than 20 degrees to 57° C. Further computational modeling, synthesis of PNA and γPNA, design and synthesis of DNA nanorings, and imaging with AFM and TEM to quantify extent of twist and variation of observed twist may be tested.

Example 2—Design and Synthesis of all-PNA Nanostructures

Any device made of synthetic DNA must be protected from enzymatic degradation in the natural world. Further, if DNA-based nanosensors are to be introduced into the body, they must be passivated to avoid provoking an immune response in the host. Evaluation of molecular shielding is expected to prove valuable. One way to protect DNA is to create hybrid DNA-PNA systems having higher stability and offering improved resistance to nucleases. However, a more radical approach to dealing with both of these challenges would be to build nanostructures entirely out of PNA. Such systems, being constructed out of a bioorthogonal material, are not substrates for endogenous proteases and nucleases and should not stimulate an immune response from a host (although toxicity should be considered). They would also benefit from higher thermal stability than typical DNA-based nanosystems and reduced sensitivity to salt concentrations after formation.

The current practical limitations associated with PNA synthesis include high cost per sequence and low yields for long sequences, which means that any all-PNA nanosystem would need to be formed from as few, short sequences as possible. And with a practical PNA synthesis length limit of approximately 20 bases, existing SST designs with 42 bases for Yin-style SSTs and 21 bases for Yang-style SSTs may be adapted for shorter-stranded, e.g., all-PNA nanostructures.

Example 3—Triggerable all-PNA Nanostructure

γPNA is investigated as a shape-change triggering molecule for all-PNA constructs. Given the flexibility of PNA, we expect an all-PNA SST nanosystem to be more flexible than its all-DNA SST cousin. Thus strand invasion by torsionally stiffened γPNA is expected to lead to structural twisting that may be quantified using TEM, AFM, or even more simply, via gel electrophoresis (coiled rings with smaller effective radii should run faster through gels). An additional benefit of strand invasion by γPNA has to do with handedness. γPNA can be made to assume a right-handed chiral structure or a left-handed chiral structure, and while each can bind to standard PNA, left- and right-handed γPNA cannot bind to each other. We propose to test this by creating all-PNA nanoring constructs that have 2 invasion sites per bundle segment, and may image these nanorings after invasion first by a right-handed γPNA (right-handed twist application), and then image again after invasion by a second left-handed γPNA (left-handed twist to cancel initial right-handed twist). If twist and writhe are visible on TEM or AFM after invasion by the first strand, we would expect that the ring would untwist and unwrithe after addition of the left-handed γPNA. Such a mechanism would allow for reversible twist without removal of the invading strands. To identify the proportion of strand invasion sites that are invaded, we can strand-invade with fluorescently-labeled γPNA and use total internal reflection fluorescence (TIRF) microscopy to look for co-localization nanoring-anchored fluorophore (e.g. Cy3) and γPNA-carried fluorophore (e.g. Cy5). We may also perform melting experiments on PNA duplexes treated with left-handed and right-handed invading γPNA. Toe-holds (small, un-hybridized binding domains) may be added to the all-PNA SST nanoring designs to promote strand-displacement by γPNA.

The nanorings may be characterized using TEM and AFM. We may measure diameters for rings and quantify observed writhe twisted structures. Additionally, we can quantify the percentage of rings that are twisted and those that remain ring-shaped after strand-invasion across a range of reanneal conditions. We can also perform complementary gel electrophoresis studies to identify gel parameters necessary to distinguish nanoring populations with varying levels of twist. Stability of these constructs in salt may be tested by subjected them to low Mg conditions and then running control and low-salt populations on gels. We also can run our all-PNA nanorings and twisted nanoring constructs through gels of varying pore size to investigate size exclusion of rings. This final investigation points to an application for selective delivery of nanorings by precoiling to enable entry into constricted environments.

Example 4—Applications for Nanomaterials Made Entirely of PNA

The following are examples of uses for the materials and structures described herein.
Environmental monitoring, for example using fluorescent nanosensors to detect contaminants or chemical byproducts of undesired reactions.
Cell-compatible nanobiosensors that can resist nuclease and protease degradation. Sensors could be attached to substrates for cell culture or attached to the cell for membrane or intracellular proteins.

Mechanosensors and other detector platforms made of PNA with fluorescent functionalization could be used for long-term monitoring of organic and inorganic structures in aqueous environments.

PNA nanomaterials designed consisting entirely of short stranded PNA building blocks could be used as entirely synthetic systems for molecular computation and storage of information.

PNA computing platforms that are structurally-analogous to DNA based computing platforms.

Toehold-mediated strand displacement reactions using PNA strands can be used to impart or relieve prestress (via addition of force and torque) in a PNA nanostructure, allowing for remote actuation and shape change. Further, by use of left-handed γPNA, right-handed γPNA, and/or achiral PNA, we may be able to alter the twist of a PNA nanostructure without imparting or relieving axial stresses.

PNAs have been used to turn off translation of specific regions of cellular DNA. Long-residing, enzyme-resistant PNA nanostructures could potentially be used as cellular reservoirs for transcription-regulating PNAs. Using strand displacement and simple hybridization reactions, PNA nanostructures could act as sensors to regulate transcription on demand.

Example 5—Production of .BILD Files

U.S. Provisional Patent Application No. 62/919,781, filed Mar. 29, 2019, which is incorporated herein by reference in its entirety, and to which the present application claims priority provides a Python script (createBILD.py) written to create .BILD files (test60degSimpler.bild) of the PNA nanotube structures. These .BILD files can be viewed using the open source software UCSF Chimera. The script is for generating 3-helix tube visualizations (createBILD.py), the .BILD output file (test60degSimpler.bild), and screenshots of that structure viewed in UCSF Chimera (3helixBILDfile).

Example 6—Ss-γPNA SST Structures

Methods

Materials. Unmodified and HPLC-purified modified DNA were purchased from IDT DNA. All diethylene-glycol containing γ-modified PNA were obtained from Trucode Gene Repair, Inc. (Woburn, MA). Oligomer sequences are shown in Table C. Polar aprotic solvents like DMF, DMSO and ACN were purchased in their anhydrous form from Sigma-Aldrich. All aqueous buffers were prepared in-house with chemicals like NaCl, KCl, SDS, $Na_2HPO_4$ and $KH_2PO_4$ purchased from VWR.

TABLE C

Individual γPNA and DNA oligomer sequences used with modifications as indicated. Underlined bases indicate the gamma-position modification on each sequence. Sequences were generated and verified using the DNA Design software developed by the Winfree Lab at Caltech.

| γPNA oligomer name | Sequence (SEQ ID NO:) | DNA oligomer name | Sequence (SEQ ID NO:) |
|---|---|---|---|
| P1 | N-AATAGCGTTCAC-C (1) | D1 | 5'-AATAGCGTTCAC-3' (1) |
| P2 | N-GCTATTGAGTAA-C (2) | D2 | 5'-GCTATTGAGTAA-3' (2) |
| P3 | N-GACATCTTACTC-C (3) | D3 | 5'-GACATCTTACTC-3' (3) |
| P4 | N-CTGGCGTGCGGA-C (4) | D4 | 5'-CTGGCGTGCGGA-3' (4) |
| P5 | N-CGCCAGCCCTCG-C (5) | D5 | 5'-CGCCAGCCCTCG-3' (5) |
| P6-biotin | N-Biotin-GTGAACCGAGGG-C (6) | D6 | 5'-GTGAACCGAGGG-3' (6) |
| P7 | N-AGTTTTGATGTC-C (7) | D7 | 5'-AGTTTTGATGTC-3' (7) |
| P8-Cy3 | N-Cy3-AAAACTACAGAA-C (8) | D8 | 5'-AAAACTACAGAA-3' (8) |
| P9 | N-TCCGCATTCTGT-C (9) | D9 | 5'-TCCGCATTCTGT-3' (9) |
| P2m (mismatch) | N-GCTATTGAGTAAA-C (10) | D3-FAM | 5'-GACATCTTACTC-FAM-3' (3) |

Solid-Phase PNA Synthesis. The aeg-PNA monomers were purchased from Polyorg Inc. (Leominster, MA) and used without further purification. PNA sequences (see Table D) were synthesized using the solid-phase BOC-protection peptide synthesis strategy. Oligomers were synthesized off of p-Methyl-benzhydrylamine resin_HCl (0.45 mequiv/g, Peptides International). The number of active amine sites on the resin was lowered to 0.1 mequiv/g by coupling the first monomer of the respective sequence to the resin at 0.1 mmol and then capping unreacted amine sites by acetic anhydride (Sigma-Aldrich). Boc-PNA were coupled to the resin using 2-(1H-benzotriazol-1-yl)-1,1,3,3-tetramethyluronium hexafluorophosphate (379 mg, 1.0 mmol, HBTU, Chem-Impex) with N,N-dicyclohexylmethylamine (Sigma-Aldrich) as the base, respectively. Qualitative Kaiser tests were performed to assess resin deprotection and successful monomer coupling. Oligomers were cleaved from the solid support using m-cresol/thianisole/TFMSA/TFA (1:1:2:6). PNA is precipitated using cold diethyl ether. Purification of the PNA oligomers was performed by reverse-phase high pressure liquid chromatography (HPLC) with a C18 silica column on a Waters 600 controller and pump with a Waters 2996 photodiode array detector to monitor absorbance changes.

TABLE D

Individual aeg-PNA oligomer sequences.

| aeg-PNA oligomer name | Sequence (SEQ ID NO:) |
|---|---|
| aeg-P1 | N-AATAGCGTTCAC-C (1) |
| aeg-P2 | N-GCTATTGAGTAA-C (2) |
| aeg-P3 | N-GACATCTTACTC-C (3) |
| aeg-P4 | N-CTGGCGTGCGGA-C (4) |
| aeg-P5 | N-CGCCAGCCCTCG-C (5) |
| aeg-P7 | N-AGTTTTGATGTC-C (7) |
| aeg-P9 | N-TCCGCATTCTGT-C (9) |

Characterization of aeg- and γ-modified PNA oligomers was performed using matrix assisted laser desorption ionization coupled to time-of-flight (MALDI-ToF) mass spectrometry on an Applied Biosystems Voyager biospectrometry workstation using α-cyano-4-hydroxycinnamic acid as the matrix (10 mg/mL in water/acetonitrile, 0.1% TFA). MALDI-ToF spectra were obtained for aeg oligomers: aeg-P1, aeg-P2, aeg-P3, aeg-P4, aeg-P5, aeg-P7, and aeg-P9, and for mini-PEG γ-modified oligomers: P1, P2, P3, P4, P5, P6, P7, P8, P9, and P2m, confirming the quality of those products.

Melting Experiment Assay. Variable temperature UV-Vis experiments were performed in a Varian Cary 300 spectrophotometer equipped with a programmable temperature block in 1 cm optical path, quartz cells. The melting curves were primarily recorded over a temperature range 15-90° C. for both cooling (annealing) and heating (melting) cycles at a rate of 0.5° C./min. The lower temperature was sometimes extended to 4° C. The samples were kept for 10 min at 90° C. before cooling and at 4 or 15° C. before heating. The melting temperature (Tm) was determined from the peak of the first derivative of the heating curve.

Thermal melting curves in 100% DMF show severe noise or signal disturbances partly because of high absorbance of DMF at the wavelength range used during experimentation. This is a noted phenomenon in literature. However, it was possible to obtain Tm values for select 3-oligomer PNA systems at 5 µM concentration per oligomer.

Nanostructure assembly. Individual γPNA, DNA or aeg-PNA strands were added to different solvent conditions at 500 nM final concentration per oligomer based on the conditions for the study mentioned in the text and annealed using a Bio-Rad C1000 thermal cycler (Table E) by decreasing the temperature from 90 to 70° C. over 200 min, from 70 to 40° C. over 900 min, from 40 to 20° C. over 200 min and finally holding at 4° C.

TABLE E

Thermodynamic parameters from UV melting curve analysis of 2- and 3- oligomer γPNA systems indicating both trends in cooperativity and reasonable thermal stability of γPNA duplexes in organic solvents.

| Helix | No. of oligomers | Oligomer strand ID | Buffer/ solvent | $T_m$ (° C.) |
|---|---|---|---|---|
| A | 2 | P2, P3 | 1X PBS | 39 ± 1 |
| A | 3 | P2, P3, P7 | 1X PBS | 28 ± 1, 59 ± 1 |
| A | 3 | P2, P3, P7 | DMF | 51 ± 1 |
| A | 3 | P2, P3, P7 | DMSO | 54 ± 1 |
| B | 2 | P4, P5 | 1X PBS | 43 ± 1 |
| B | 3 | P4, P5, P6 | 1X PBS | 53 ± 1 |
| B | 3 | P4, P5, P6 | DMF | 50 ± 1 |
| C | 2 | P8, P9 | 1X PBS | 56 ± 1 |
| C | 3 | P7, P8, P9 | 1X PBS | 63 ± 1 |
| C | 3 | P7, P8, P9 | DMF | 56 ± 1 |

TIRF imaging. Nanotubes were imaged at 60× and 90× magnification on a Nikon Ti2 microscope equipped with a 60×1.4 NA Plan-Apo oil-immersion objective, 1.5× magnifier, Prime 95B sCMOS camera (Photometrics), Nikon Perfect Focus System, and Nikon NIS-Elements software. To create flow chambers, channels ~3 mm apart were made with double-sided tapes on a glass slide. The coverslips were coated with 0.1% collodion in amyl acetate (EMS). Nanotubes were then immobilized to the coverslip surface at room temperature as follows. Biotinylated-BSA at 0.1 mg/mL in 1×PBS was incubated for 2-4 minutes. Excess biotin-BSA was washed out, and the surface was incubated with BSA (10 mM DTT+1 mg/mL BSA in 1×PBS) for 2 minutes. Next, streptavidin at 0.1 mg/mL in BSA solution was incubated for 2-4 minutes. Excess streptavidin was washed out with BSA. In the case of polar-aprotic solvent mixtures, the flow chamber was then washed with the same solvent mixture as the sample. Finally, 15 µL of nanotubes was added and incubated for 3-5 minutes. Excess nanotubes were washed out of the chamber with 1 mM Trolox.

TEM imaging. 4 µL of annealed nanotubes sample was introduced on to a formvar-coated copper TEM grids. After 15 seconds the solution was wiped off and the sample was stained by addition of 1% uranyl acetate (EMS), incubated on the sample for 5 seconds. Samples were imaged at 80 keV on a Joel JEM1011 TEM.

Results

Concept and design of γPNA 3-helix tube. We present here a structural motif for building periodic nanotubes with 9 unique γPNA strands. Our design is adapted from the single-stranded tile (SST) approach in DNA nanotechnology. Forming DNA SST nanotubes generally requires only a few distinct oligonucleotide species (4 to 20) that can polymerize and grow to become multiple microns in length.

Figure 8:
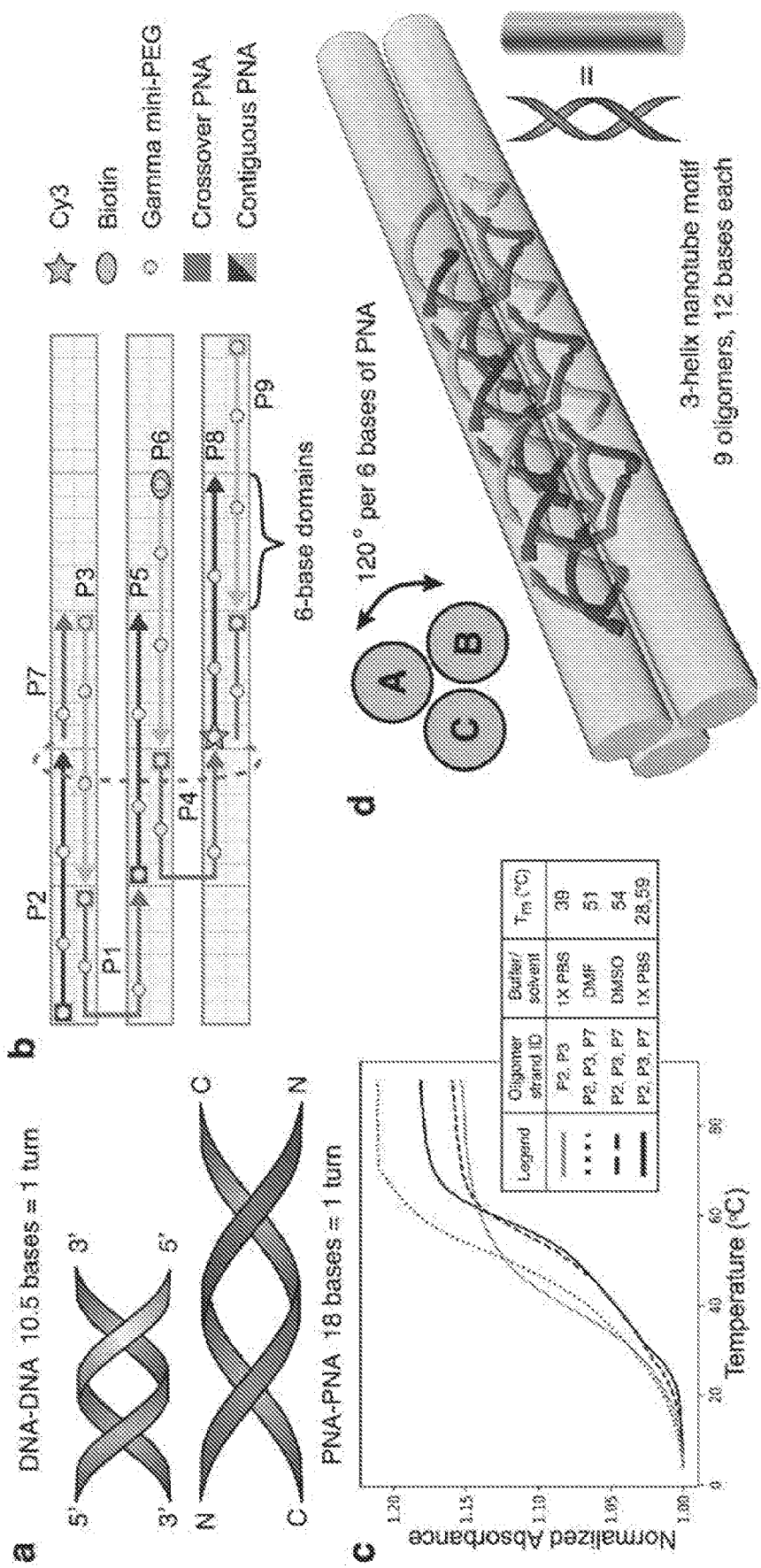
FIG. 8: The design of 3-helical γPNA nanotubes. a) Schematic comparison between a full helical turn of DNA and PNA double helix. B-form DNA is typically stable with 10.5 bases per helical turn while PNA has a helical pitch of 18 bases per turn. b) A schematic representation of the structural motif for the SST design that shows 6-base domains and an overall repeat unit of 18 bases. Each PNA oligomer is modified at the 1, 4 and 8 γ-positions with (R)-diethylene glycol (gray dots) to enable pre-organized helical conformation. γPNA oligomers are classified into contiguous or crossover PNAs based on their position in the motif. Specific γPNA oligomers (P8 and P6) are labelled with fluorescent Cy3 (star) and biotin (oval) respectively, to enable detection of structure formation using fluorescence microscopy. c) Melt curve studies show the melting temperatures of 2-oligomer and 3-oligomer substructures in different solvent conditions vary between 39 to 59° C. This indicates that 6-base domains are sufficiently stable for γPNA-γPNA systems in PBS, DMSO and DMF. The lower temperature transitions evident in the three-stranded systems are attributed to melting of helical structure within the overhanging γPNA domains. To substantiate this prediction, we measured melting temperatures of the associated single-stranded γPNAs with the same buffer conditions, in which melt curves of ss-γPNA oligomers P2, P3 and P7 indicated a $T_m$ between 28 and 34° C., and two of the associated oligomers showed melting temperatures around 28° C. d) 6-base domains correspond to 120° rise in helical rotation enabling the structural motif to program the assembly of 3-helix nanotubes that can polymerize lengthwise.

FIG. 8 (a) shows one structural difference between PNA and DNA double helices. B-form 95 DNA are right-handed double helices that rotate 34.3° per base pair, or 10.5 base pairs per helical turn. To account for this property and prevent undesired pre-stress, DNA SST designs usually aim for 10.4-10.7 bases per helical revolution Unlike DNA, PNA double helices are reported to have 18 base pairs per turn. Therefore, we chose to design an SST motif with 18 bases-long repeat unit to make a nanotube consisting of three interwoven double helices. The design reported here (FIG. 8 (b)) is based on repeating tubular units where the number of unique oligomers required to form the individual units are 3× the number of helices in the corresponding bundles (i.e. 9 oligomers for 3-helix nanotube). The constituent strands fall into one of two categories: two-thirds of them (6 oligomers) are contiguous strands that are arranged linearly and the other one-third (3 oligomers) are crossover strands that each form a crossover from one helix to a neighboring helix. Each γPNA sequence contains 3 gamma modifications with (R)-diethylene glycol (mini-PEG) at the 1, 4 and 8 positions (FIG. 8 (b), gray dots). In order to immobilize and visualize PNA nanostructures using fluorescence microscopy, N-terminal functionalization of select strands with biotin (FIG. 8 (b), oval) and Cy3 (FIG. 8 (b), star) was performed. Each oligomer consists of 12 bases, which follows a 6+6 domain-binding pattern. For PNA double helices with 18 base pairs per full helical turn, 6 base pairs correspond to 120° rise in helical rotation in a triangular-sectioned nanotube (FIG. 8 (b and d).

For thermal stability, most DNA-based SST systems use domains of 10 or 11 bases. To verify that 6-base γPNA domains would bind sufficiently strongly, we measured the melting temperatures with 2- and 3-oligomer γPNA-γPNA systems using 6-base domains (FIG. 8 (c)) and compared them to studies of DNA-DNA systems in aqueous buffers from literature (Table F). Table F summarizes UV-melting studies in PBS and 1×TAE, 12.5 mM $Mg^{2+}$ of 2-oligomer and 3-oligomer DNA systems. Data sets demonstrate that the maximum melting temperatures ($T_m$) for 7-base overlaps is 37° C. (3-oligomer, TAE-Mg buffer) and for 10-base overlaps is 50° C. (3-oligomer, TAE-Mg buffer).

TABLE F

| Number of DNA oligomers | Length of domain | Buffer | $T_m$ (° C.) |
| --- | --- | --- | --- |
| 2 | 7 bp | 1xPBS | <20° C. |
| 3 | 7 bp | 1XPBS | 30 ± 1 |
| 3 | 7 bp | 1X TAE, 12.5 mM Mg | 37 ± 1 |
| 2 | 10 bp | 1xPBS | 39 ± 1 |
| 3 | 10 bp | 1XPBS | 43 ± 1 |
| 3 | 10 bp | 1X TAE, 12.5 mM Mg | 28 ± 1 |
| | | | 50 ± 1 |

These studies demonstrate that the thermal stability of 6-base γPNA domains are similar to or exceed that of 10-base DNA domains. The 3-oligomer DNA-DNA system showed two-transitions in its melt-curve in aqueous buffer condition supplemented with Magnesium. The lower transitions in this case are attributed to melting of helical structure within the overhanging DNA domains. Additionally, the 3-oligomer γPNA-γPNA system in the aqueous buffer condition (FIG. 8 (c)— black solid line) showed two-transitions in its melt curve. The lower temperature transitions evident in the three-stranded systems are attributed to melting of helical structure within the overhanging γPNA domains. To substantiate this prediction, we measured melting temperatures of the associated single-stranded γPNAs with the same buffer conditions, in which melt curves of ss-γPNA oligomers P2, P3 and P7 indicated a $T_m$ between 28 and 34° C., and two of the associated oligomers showed melting temperatures around 28° C.

Melt curve studies for these 3-oligomer systems were also performed in organic solvents including DMSO and DMF as shown in FIG. 8 (c). These results indicate γPNA duplexes formed successfully in organic solvents and experienced only minor reductions in melting temperatures in DMSO and DMF as compared to aqueous buffers formation (FIG. 8 (c)—dotted and dashed black lines). This is in stark contrast with assemblies of short DNA oligomers, which are denatured in DMSO. Unlike their DNA counterparts, organic solvent mixtures have a much smaller effect on the thermal stability of PNA-PNA duplex because the destabilization of DNA duplexes in an aprotic solvent is assumed to be predominantly caused by dehydration and ion exclusion.

Comparing melt curve studies between unmodified aeg-PNA and γPNA duplexes for isosequential 2- and 3-oligomer systems in aqueous buffer as well as DMF and DMSO verified that both aeg-PNA and γPNA systems experience either minor or no reductions in melting temperatures (FIG. 8 (c) and Table G). However, the isosequential 3-oligomer γPNA system shows considerably higher melting temperatures in comparison to the 3-oligomer aeg-PNA system in aqueous buffer as well as DMF and DMSO solvents.

TABLE G

| Oligomer Strand ID | Buffer/ Solvent | $T_m$ (° C.) |
| --- | --- | --- |
| aeg-P2, P3 | 1x PBS | 39 |
| aeg-P2, P3, P7 | DMF | 38 |
| aeg-P2, P3, P7 | DMSO | 40 |
| aeg-P2, P3, P7 | 1x PBS | 42 |

DNA nanostructures with multiple DNA oligomers fold cooperatively at temperature ranges higher and narrower than the melting temperatures of associated individual domains. Given that we find an increase in melting temperature from 7 to 19° C. for our 2- to 3-stranded γPNA systems (FIG. 8 (c)), we expect that 3-helix SST nanotubes will have further increased thermal stability than 2- and 3-oligomer systems (see Table F).

In total, 9 oligomers make up this γPNA nanotube structural motif, and each oligomer is 12 bases long. The structural motif programs the self-assembly of 3-helix nanostructures that can polymerize along lengthwise (FIG. 8 (d)). This structure is notable in being made of SSTs with only two domains each. A resulting property of this design is that theoretically, all sequences must be present and successfully bound in order to enable polymerization. In other words, structural formation indicates that every oligomer has been successfully incorporated.

Figure 9:
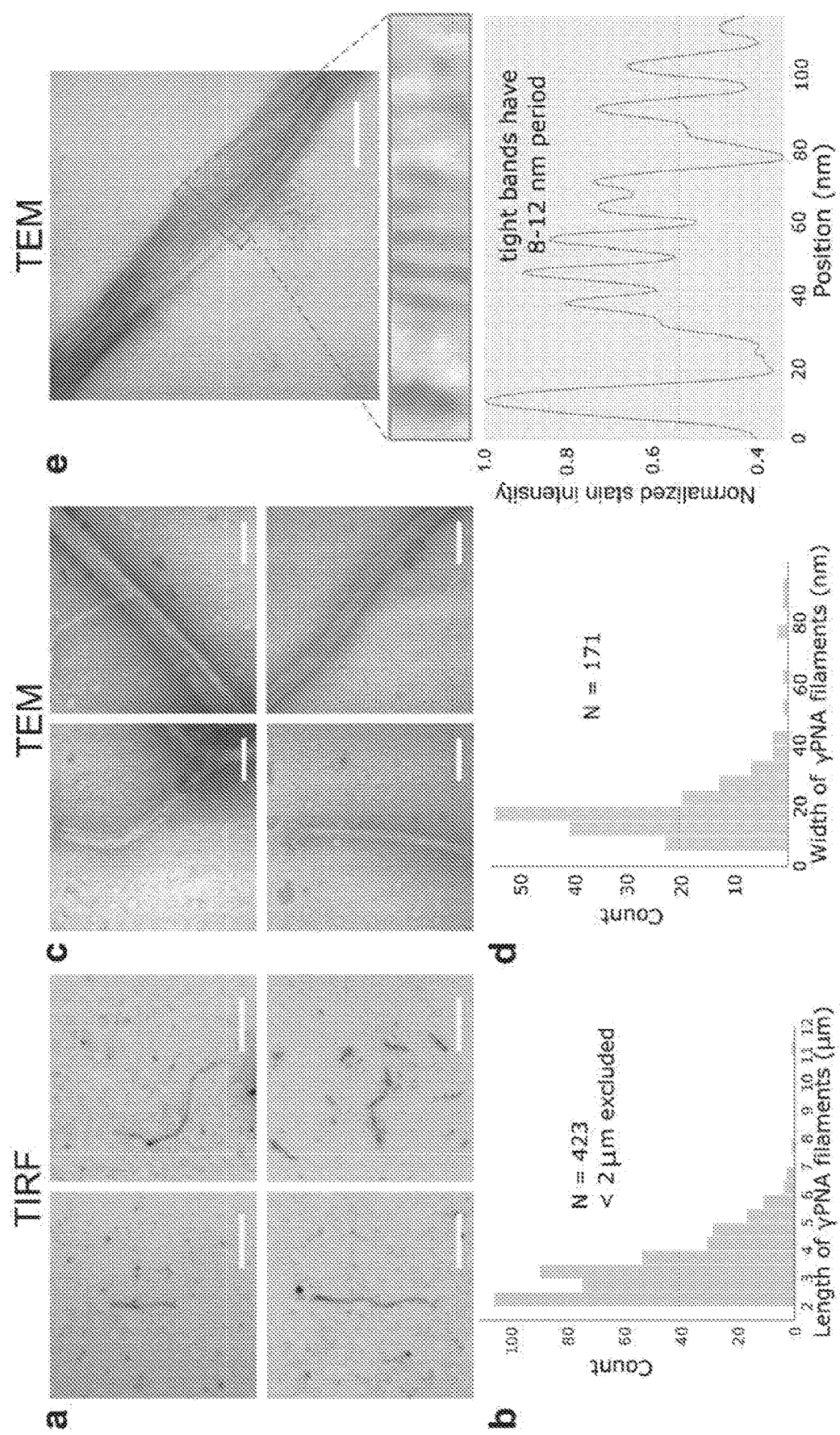
FIG. 9: Evidence and characterization of self-assembly of γPNAs to form 3-helix nanotubes using TIRF and TEM assays. a) TIRF panels (5 μm scale bar) of γPNA self-assembly in 75% DMSO:H$_2$O (v/v) obtained through monitoring the Cy3 channel provides evidence of well-organized, micron-scale filamentous structures. b) The length distribution of 3-helix tube structures (sample size, N=423) self-assembled in 75% DMSO:H$_2$O is thresholded to include elongated nanostructures at least 2 μm in length. While short filaments are more prevalent, filaments up to 11 μm in length were also observed. c) TEM panels (100 nm scale bar) of γPNA nanostructures annealed in 75% DMSO:H$_2$O (v/v) shows bundling of γPNA nanostructures at the nanoscale level along its width. d) Width distribution of γPNA nanostructures (sample size, N=171) using TEM studies shows a right-skew with a median width of 16.4 nm and maximum values beyond 80 nm. This suggests that nanostructures bundle together when annealed in 75% DMSO:H$_2$O (v/v). e) Line profile scan along the width of any bundled γPNA nanotubes shows the presence of thinner γPNA sub-structures occurring between periods of 8 to 12 nm, which agrees with constituent structures of 5 to 6 nm diameter as predicted by our motif.

Evidence of γPNA self-assembly. Favorable conditions for self-assembly of γPNA oligomers were thereafter determined by screening combinations of various temperature anneal ramp cycles [0.5-0.1° C./min and 0.1° C./1-3 minutes], various functional additives [5-30% (w/v) PEG8000, 10-40% (v/v) formamide, 1-8 M urea in varying concentrations], and a variety of solvent mixtures including organic solvents like DMF [10-87.5% (v/v)], DMSO [10-87.5% (v/v)], acetonitrile [10-50% (v/v)] and primary alcohols [10-50% (v/v) methanol, ethanol]. These systems were then characterized using Total Internal Reflection Fluorescence (TIRF) microscopy to visualize structure formation. While self-assembly was observed in organic solvent mixtures such as 75% $DMF:H_2O$ (v/v %) and 40% 1,4-dioxane:$H_2O$ (v/v %), the microscopic observation of well-organized architectures was most evident from our TIRF studies when oligomers were annealed with a slow temperature ramp. (Table H) in 75% $DMSO:H_2O$ (v/v %) as shown in FIG. 9 (a).

TABLE H

Temperature ramp protocol for γPNA nanotubes.

| Temperature Range | Temperature change | Time interval per temperature change |
| --- | --- | --- |
| 90-80° C. | 0.1° C. | 1 min |
| 80-70° C. | 0.1° C. | 1 min |
| 70-60° C. | 0.1° C. | 3 min |

TABLE H-continued

Temperature ramp protocol for γPNA nanotubes.

| Temperature Range | Temperature change | Time interval per temperature change |
|---|---|---|
| 60-50° C. | 0.1° C. | 3 min |
| 50-40° C. | 0.1° C. | 3 min |
| 40-30° C. | 0.1° C. | 1 min |
| 30-20° C. | 0.1° C. | 1 min |
| 4° C. | 0.1° C. | Hold |

In contrast, no structures were visible under TIRF assays when the system of oligomers introduced had one missing PNA sequence or a mismatched PNA sequence indicating the Watson-Crick base pair driven self-assembly of these micron-scale structures. Moreover, replacing the entire system with sequence-identical DNA oligomers also did not show structure formation in either 75% DMSO:H$_2$O, 1×PBS (a physiological buffer) or 1× TAE plus 12.5 mM MgCl$_2$ (a typical DNA SST buffer) for similar and slower annealing ramps largely indicating that this structure formation is due to the large cooperativity, specificity and stability of conformationally pre-organized PNA oligomers.

Figure 10:
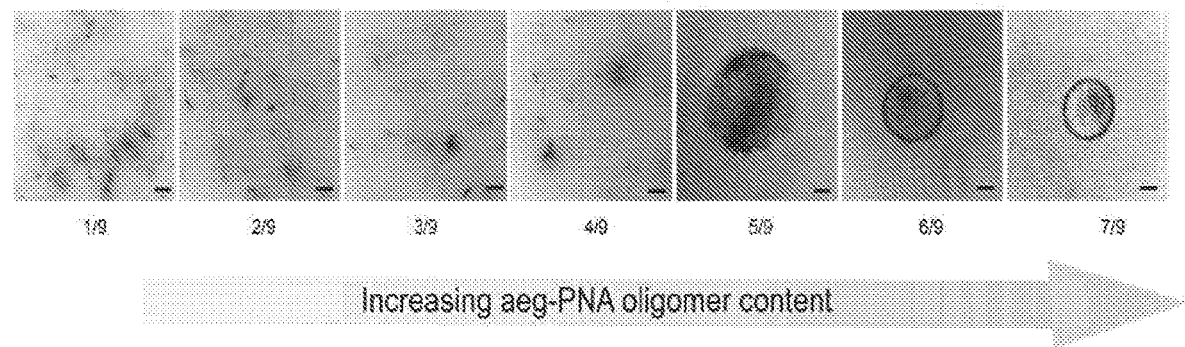
FIG. 10 provides TIRF panels (5 μm scale bar) of the self-assemblies formed by aeg-PNA-γPNA hybrids in 75% DMSO:H$_2$O (v/v) with increasing content of aeg-PNA oligomer content as indicated. Formation of aggregates are visible under TIRF microscopy when the overall aeg-PNA content is more than 50%.

For further substantiation, we sequentially introduced increasing amounts of aeg-PNA up to 7 oligomers. Systems containing combinations of up to 4 aeg-PNA oligomers under similar conditions of 75% DMSO:H$_2$O continued to form nanotubes robustly. However, when several combinations of oligomer sets containing 5 to 7 aeg-PNA oligomers were included, we observed formation of aggregates and no nanostructure formation using TIRF assays (FIG. 10).

Additionally, a histogram of contour length profile measurements of self-assembled γPNA in 75% DMSO:H$_2$O shows that nanostructures form multi-micron filaments, with some structures reaching ~11 µm (FIG. 9 (b)). These lengths compare well with existing DNA SST strategies to construct nanotubes. Transmission Electron Microscopy (TEM) imaging of the PNA system in the 75% DMSO:H$_2$O solvent mixture confirmed the formation of nanotubes at nanoscopic resolutions providing proof of concept, but showed further features that suggest bundling of nanotubes (FIG. 9 (c)).

Width measurements and line profile analysis across the width of 'bundled' γPNA 3-helix tubes using TEM data. TEM images of the designed γPNA nanotubes bundle revealed multiple dark striated regions (a cavity or hole) flanked by brighter regions (γPNA) along the middle of our constructs. This contrast occurs as uranyl acetate staining can fill only the space around the γPNA constructs. An intensity profile along the filament's cross section confirmed the existence of multiple cavities which appear as alternating bands of light and dark under TEM, suggesting bundling on nanotubes.

Additionally, the intensity profile scans provide full widths across the bundled nanotubes cross-section. The scan and analysis were performed via ImageJ.

Median widths for individual constructs were determined using quartile ranges. Outliers were excluded using interquartile range. Mann-Whitney tests were performed between all-γPNA construct and each γPNA-DNA construct to compare width measurements to verify any statistically significant difference.

Width profiles of TEM images shows a right-skew with a median width of 16.2 nm and maximum values beyond 80 nm providing further evidence that the PNA nanotubes in 75% DMSO:H$_2$O has tendencies to bundle along their widths (FIG. 9 (d)). Based on previously published γPNA-DNA and PNA-DNA helix diameters of 2.3 nm, we estimated that individual three-helix nanotubes would have diameters of 5 to 6 nm. Line profile analysis across the widths of these "bundled" nanotubes, however, show alternating bands of light and dark, with tighter alternating bands occurring in 8 to 12 nm periods, consistent with substructures that have diameters in the 5 to 6 nanometer range (FIG. 9 (e)).

Figure 11:
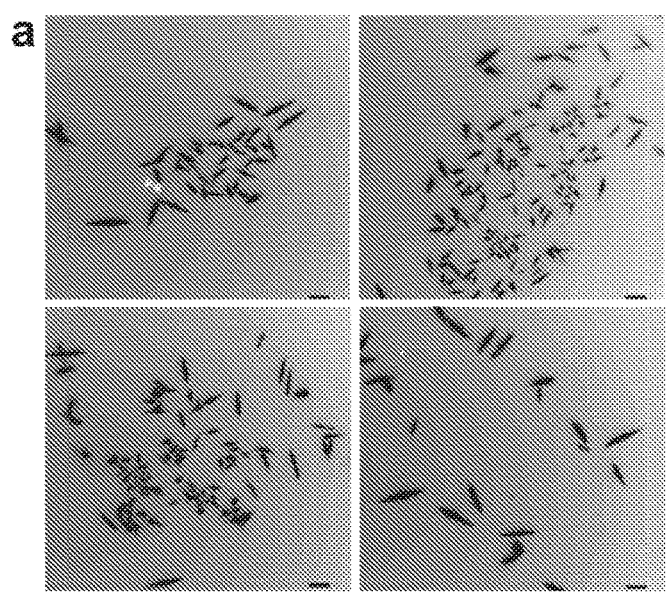
FIG. 11: TIRF assay characterization of different morphologies for self-assembling γPNA oligomers in DMF and 1,4-dioxane solvent mixtures a) TIRF microscopy images of self-assembly of γPNA oligomers in 75% DMF:H$_2$O (v/v) showing needle-like nanostructures. (5 μm scale bar) b) TIRF microscopy images of self-assembly of γPNA oligomers in 40% 1,4 dioxane:H$_2$O (v/v) showing sparse decoration of filamentous nanostructures.
Figure 11:
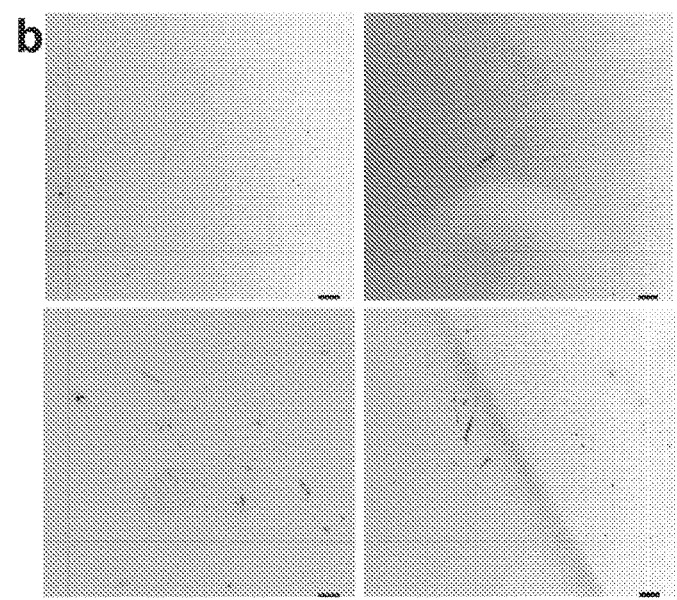

At the microscale γPNA nanostructures show a different, more spicular shape when annealed using the same thermal anneal ramp in 75% DMF:H$_2$O and sparse structure formation in 40% 1,4-dioxane:H$_2$O (v/v) indicating the role of solvent in modifying the bundling characteristics or even potentially the Watson-Crick base pair interactions between multiple PNA oligomers (FIG. 11).

Figure 12:
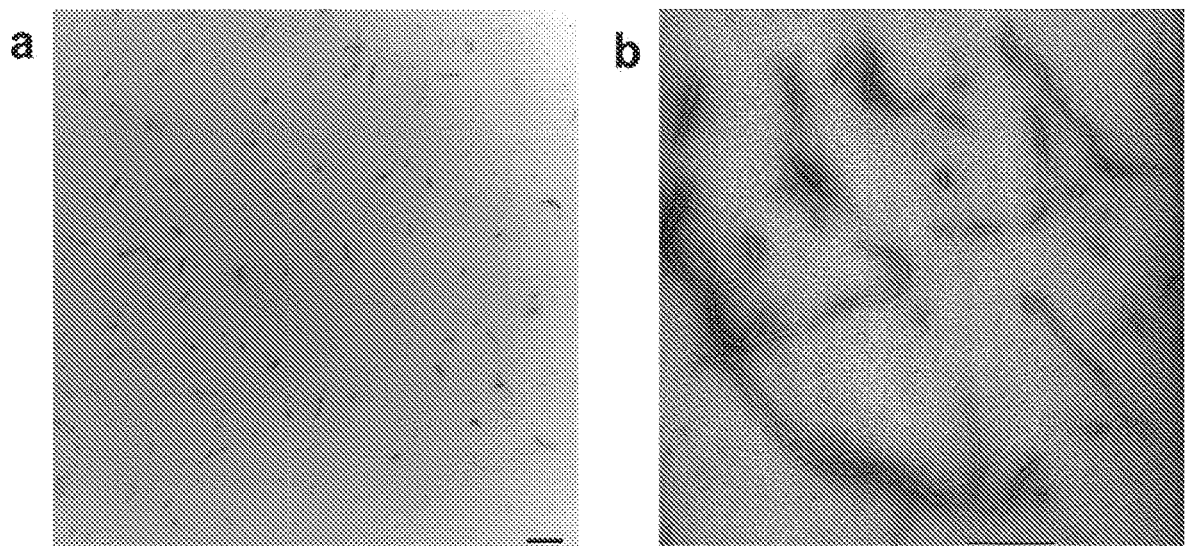
FIG. 12: TIRF and TEM data of self-assembled γPNA nanotubes in 75% DMSO:H$_2$O a) Wide view field image (5 μm scale bar) of γPNA nanotubes visualized using a TIRF microscopy while monitoring the 561 nm laser line (Cy3). b) TEM images of γPNA nanotubes visualized under low magnification (500 nm scale bar).
Figure 13:
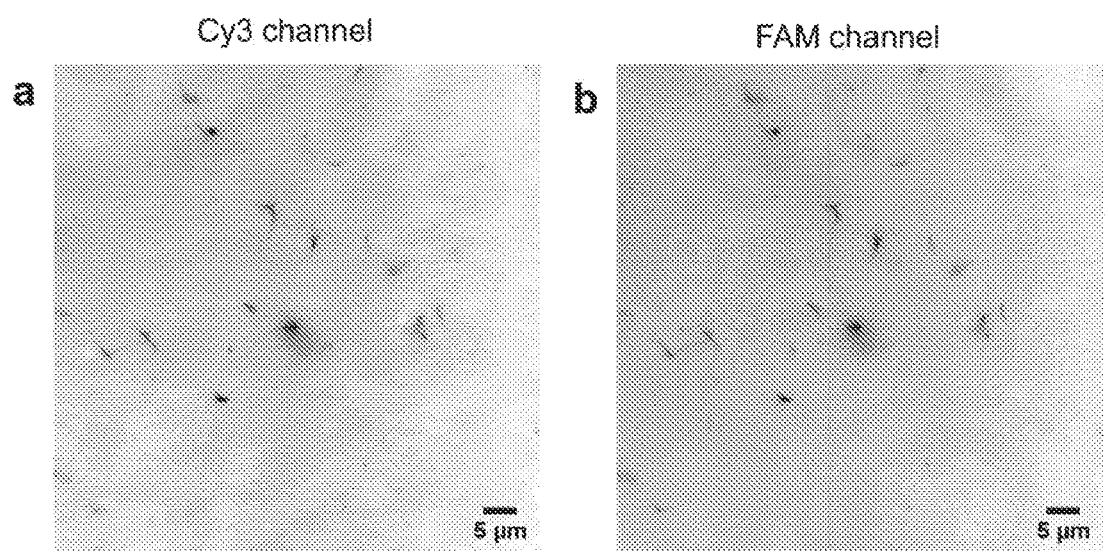
FIG. 13: TIRF co-localization study of self-assembled γPNA-DNA nanotubes in 75% DMSO:H$_2$O. Evidence of nanotube formation on replacing one γPNA oligomer (P3) with a FAM-labeled DNA oligomer (D3-FAM) through dye-colocalization studies. Image shows colocalized dyes on tubular constructs when viewed under Cy3 channel (a) and the FAM channel (b) indicating that constructs continue to self-assemble upon introduction of a dye-labelled DNA oligomer.

To investigate the capacity to form hybrid γPNA-DNA structures, analogous DNA oligomers were selectively introduced into γPNA nanostructures. DNA oligomers can introduce novel functionalization, alter charge and potentially increase hydrophilicity. For example, replacing P3 with a fluorescein-labeled DNA enabled colocalization studies shown in FIGS. 12 and 13.

In order to explore the role of DNA in modifying hydrogen-bonding and hydrophobic effects influenced by organic solvent mixtures, we introduced through sequential replacement, several combinations of up to 3 PNA oligomers with their equivalent unmodified DNA oligomers. Such an investigation leads to a better understanding of contributions from hydrophobic forces that affect nanotube structure formation and the thermodynamic feasibility of PNA-DNA hybrid nanostructures due to the introduction of a less stable PNA-DNA duplexes during self-assembly.

Figure 14A:
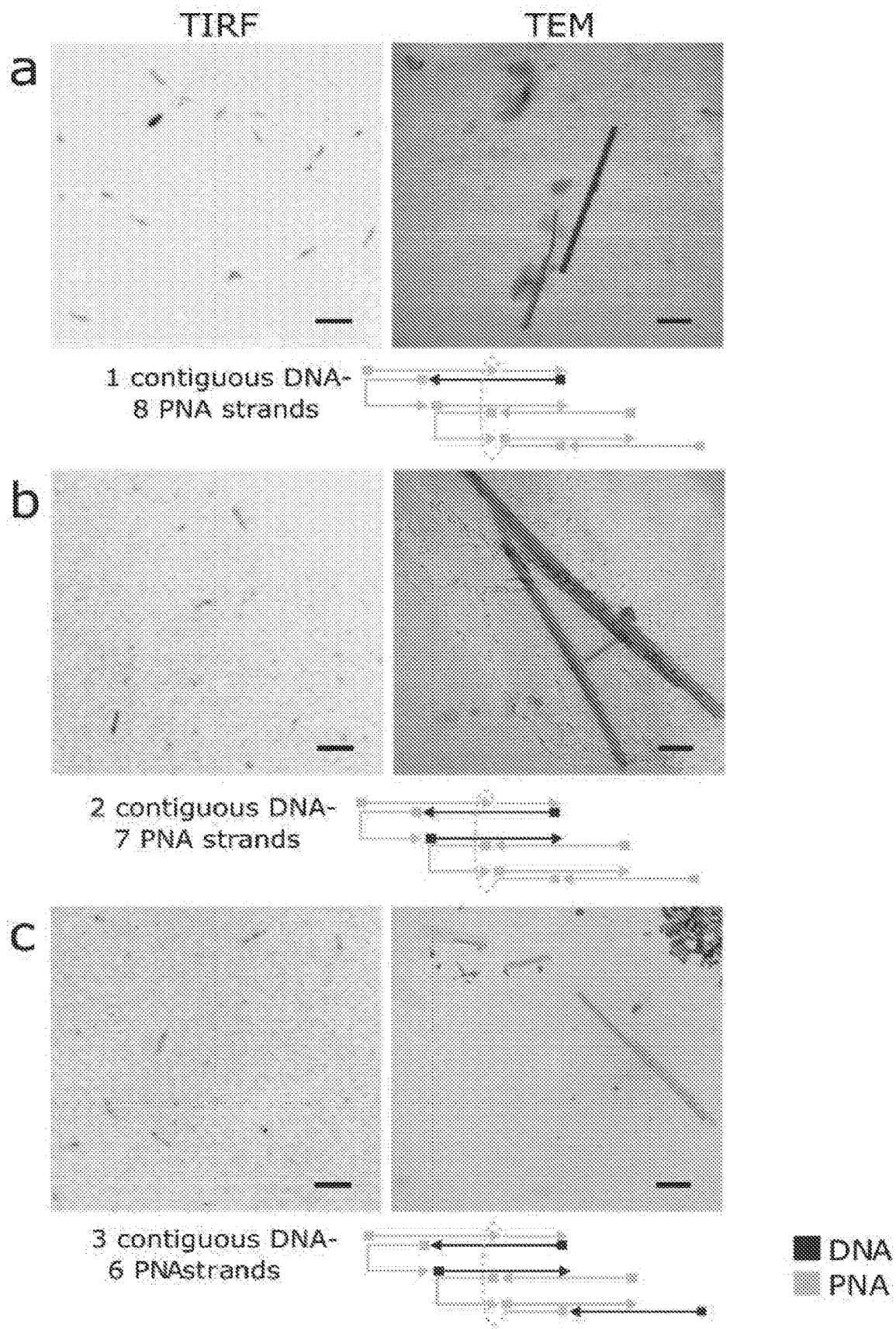
FIGS. 14A and 14B: Self-assembly and characterization of γPNA-DNA hybrid nanotubes TIRF and TEM characterization of γPNA-DNA hybrid filaments through selective and sequential replacement of γPNA oligomers with DNA. Schematic representations shown in a)-f) show the position in the SST motif replaced with DNA in the context of other γPNA sequences. Sequential replacement of: a) 1 contiguous γPNA sequence with DNA, b) 2 contiguous γPNA sequences with DNA, and c) 3 contiguous PNA sequences with DNA resulted in straight filaments. However, sequential replacement of: d) 1 crossover γPNA sequence with DNA, e) 2 crossover γPNA sequences with DNA, and f) 3 crossover γPNA sequences with DNA resulted in stellate structures with pronounced bundling effects. Scale bars on TIRF images are 5 μm and scale bars on TEM images are 100 nm.
Figure 14B:
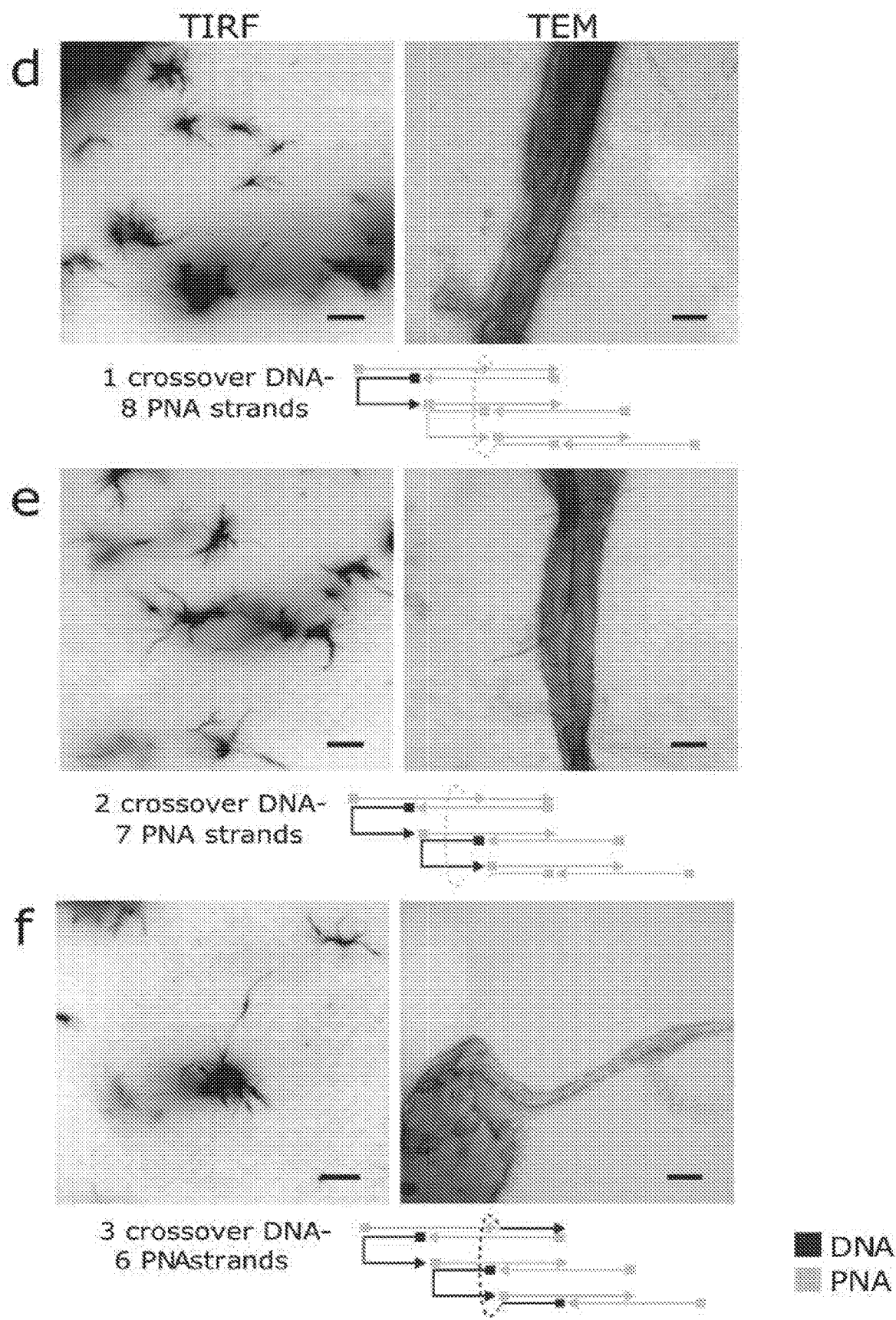
Figure 15:
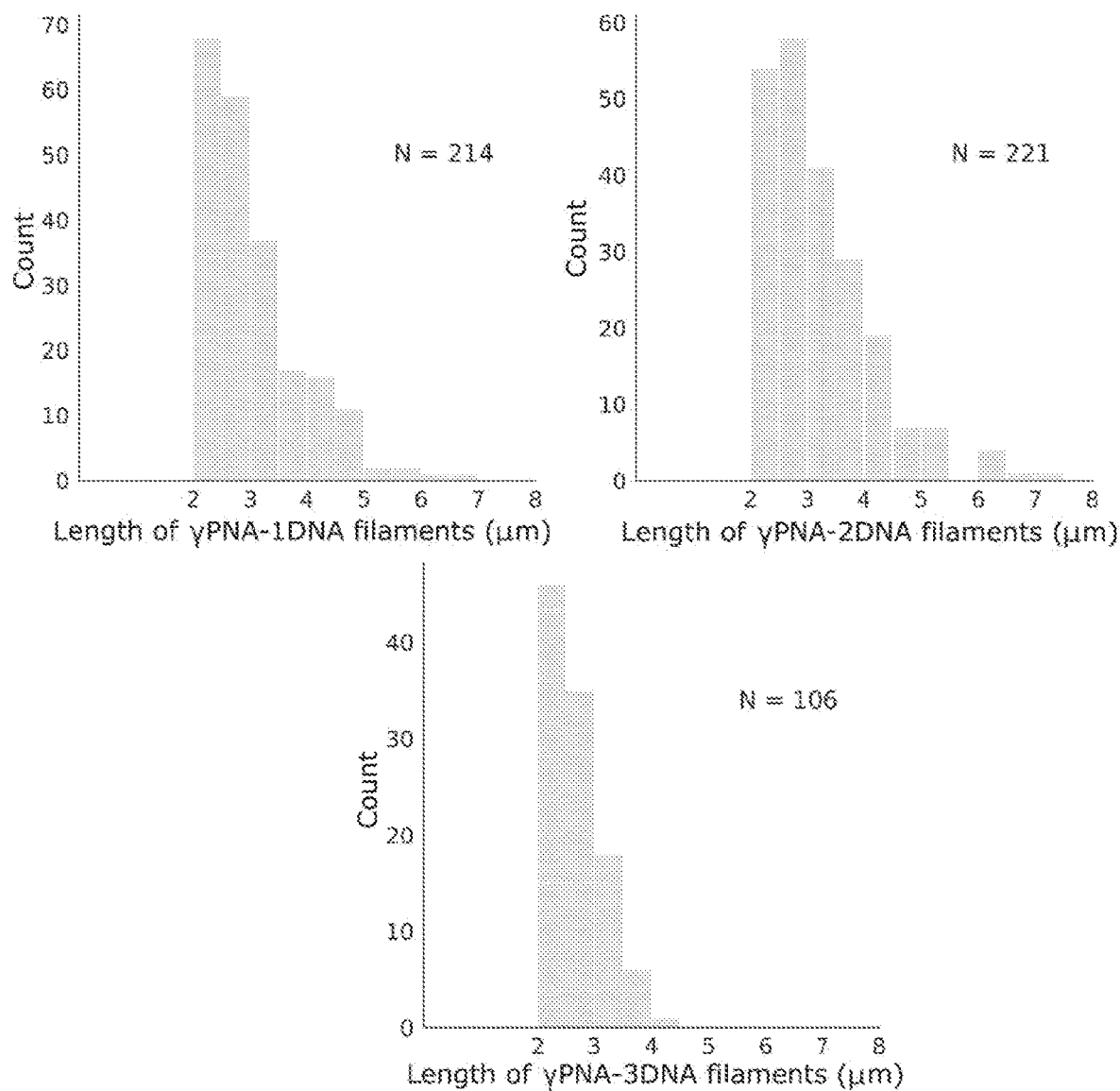
FIG. 15: Length profiles of self-assembled γPNA-DNA hybrid nanotubes (Left to Right) Length profile histograms of 3-helix γPNA-DNA hybrid tubes self-assembled in 75% DMSO:H$_2$O introducing 1 contiguous DNA oligomer (left, D3 oligomer, N=214), 2 contiguous DNA oligomers (center, oligomers—D3 and D5, N=221) and 3 contiguous DNA oligomers (right, oligomers-D3, D5 and D9, N=106) obtained from TIRF assay data sets. Analyses shows that tendencies for γPNA-DNA hybrid systems to grow beyond 2 μm reduces because of lower stabilities associated with γPNA-DNA duplexes in organic solvent mixtures.

As shown in FIGS. 14A and 14B, we sequentially replaced both the contiguous (P3, P5, P9) and crossover (P1, P4, P7) γPNA oligomers with their corresponding DNA oligomers. In all cases, the introduction of DNA did not prevent nanostructure formation, and structures were visible under TIRF microscopy. Contour length profile measurements made from TIRF studies of the contiguous γPNA replacements with DNA showed proportionally sparser fields of filaments for constructs longer than 2 µm (FIG. 15).

Figure 16:
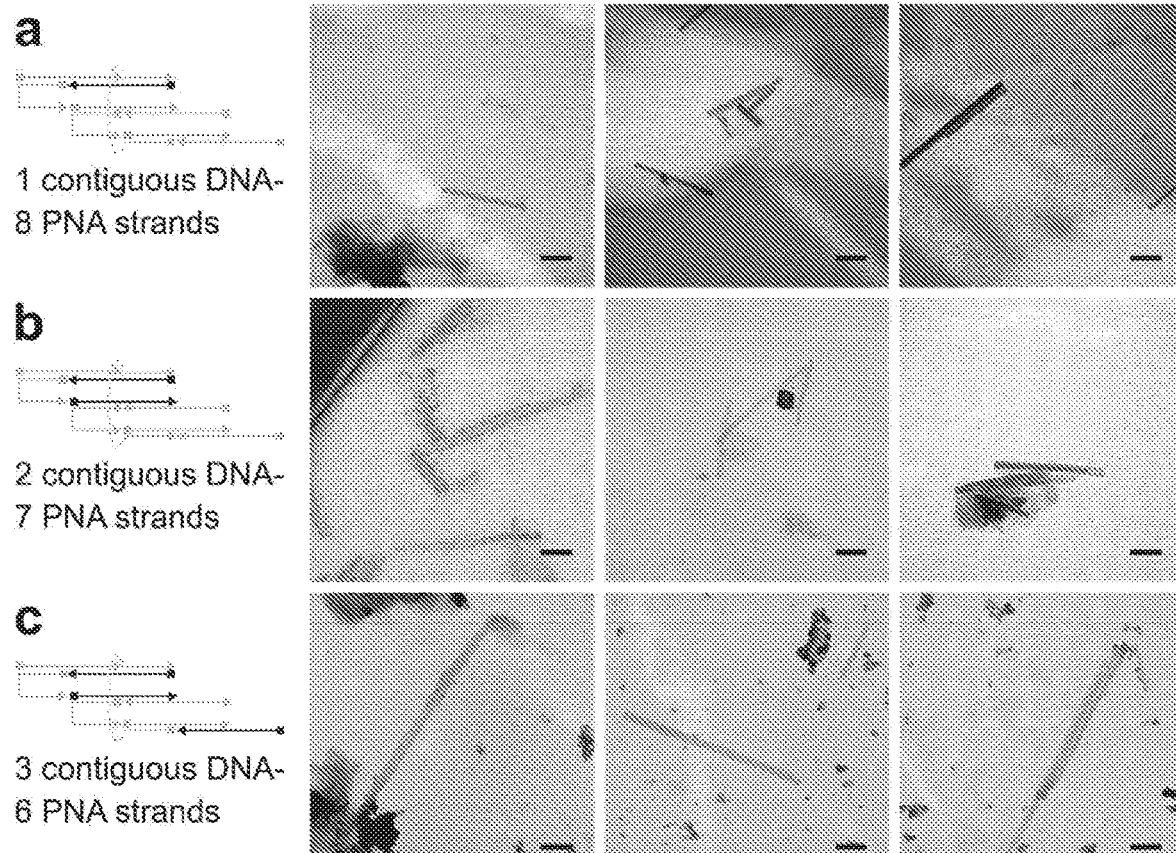
FIG. 16: TEM images of replacing contiguous γPNA oligomers with DNA. TEM image panel (scale bar 100 nm) shows that sequential replacement of contiguous γPNA with increasing amounts of analogous DNA oligomers resulted in straight filaments.
Figure 17A:
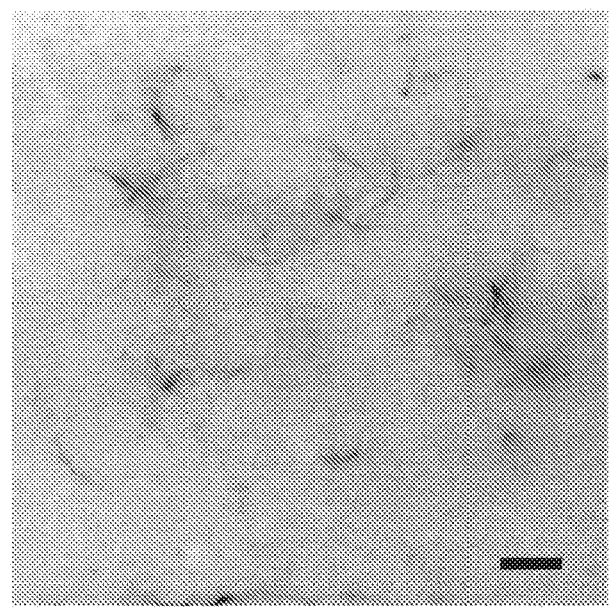
FIGS. 17A and 17B provide TIRF characterization (5 μm scale bar) of γPNA-aeg-PNA hybrid filaments through selective replacement of γPNA oligomers with aeg-PNA. Schematic representations show the position in the SST motif replaced with aeg-PNA (black arrows) in the context of other γPNA sequences (orange arrows). Sequential replacement of c) 3 contiguous γPNA sequence with aeg-PNA show no discernible morphological change and d) 3 crossover γPNA sequences with aeg-PNA resulted in stellate structures with pronounced bundling effects.
Figure 17A:
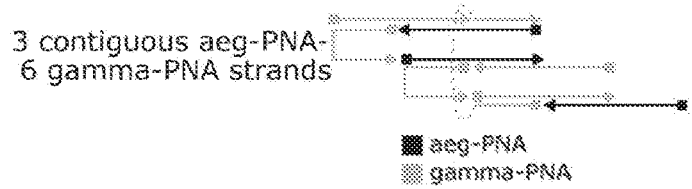

The replacement of contiguous γPNA oligomers with DNA resulted in straight filaments (FIG. 14A (a-c), FIG. 16), suggesting γPNA-DNA nanostructures adopt different morphologies upon the introduction of oligomers that carry a different charge and helical conformation. In parallel, the replacement of the same contiguous γPNA oligomers with the corresponding aeg-PNA oligomers showed no discernible difference in comparison to all-γPNA nanotubes under TIRF assays (FIG. 17A). While the mechanisms driving the differences in morphology between contiguous DNA and aeg-PNA replacements are unclear, differences may be related to the preorganization of γPNA backbone. In the context of multiple γPNA oligomers that have a helical pitch of 18 base pairs/turn, complimentary γPNA strands may not have the flexibility or the conformational freedom to accommodate corresponding DNA oligomers. Under such circumstances, DNA oligomers would have to undergo a conformational change of their own for hybridization to take place. If helical properties of γPNA and DNA determine the nanostructure morphologies, then previous studies of γPNA-DNA duplexes can be used to predict twist in a hybrid structure. Specifically, given that γPNA-DNA helical pitch has been reported to 15 bases per turn as opposed to 18 base pairs per turn found in γPNA-γPNA nanostructures. Incorporation of DNA into a structure cause right-handed twist. However, given the lack of evidence for twist, in the context of a complex nanostructure, complimentary γPNA strands sometimes may not have the flexibility or the conformational freedom to accommodate corresponding DNA oligomers. Under such circumstances, DNA oligomers would have to undergo a conformational change of their own for hybridization to take place.

Figure 17B:
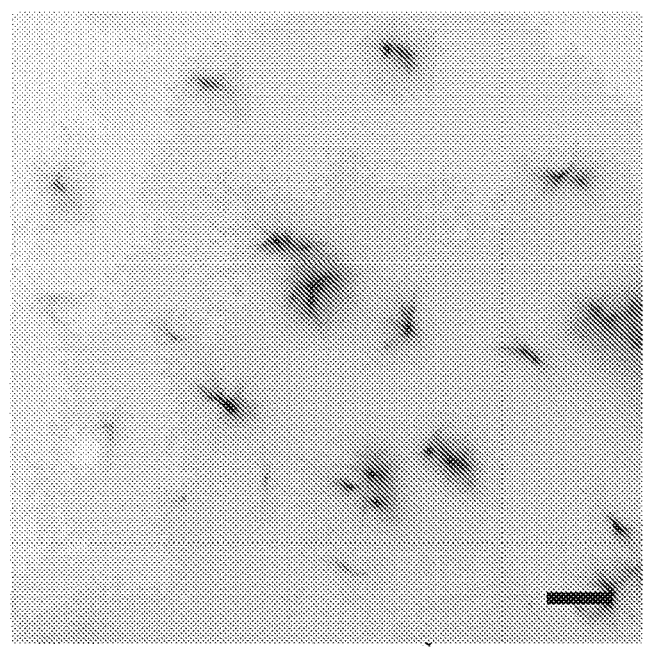
Figure 17B:
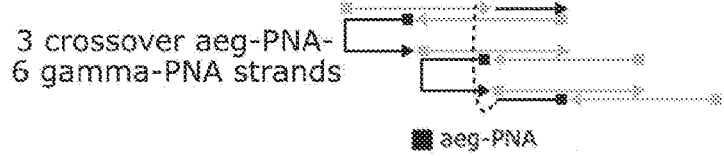

In contrast, the introduction of crossover DNA oligomers promoted more pronounced bundling of these nanotubes, with stellate structures visible under TIRF and TEM (FIG. 14B (d-f)). It is particularly interesting to note that the geometrical position of oligomeric replacement with DNA in the SST motif has a direct effect on the shape and morphology of the resultant structure. Moreover, the stellate structure morphology continues to persist albeit to a proportionally lesser degree, when the same crossover PNA oligomers are substituted with aeg-PNA oligomers (See FIG. 17B). This pronounced bundling in both DNA and aeg-PNA crossover substitution case may be the result of a combination of effects. It may depend on 1) the degree of surface and solvent exposure of the replacement oligomers affecting the overall hydrophobicity of the self-assembled architecture and 2) helical form changes associated with shorter per helix DNA-PNA binding regions of crossover oligomers.

Figure 18:
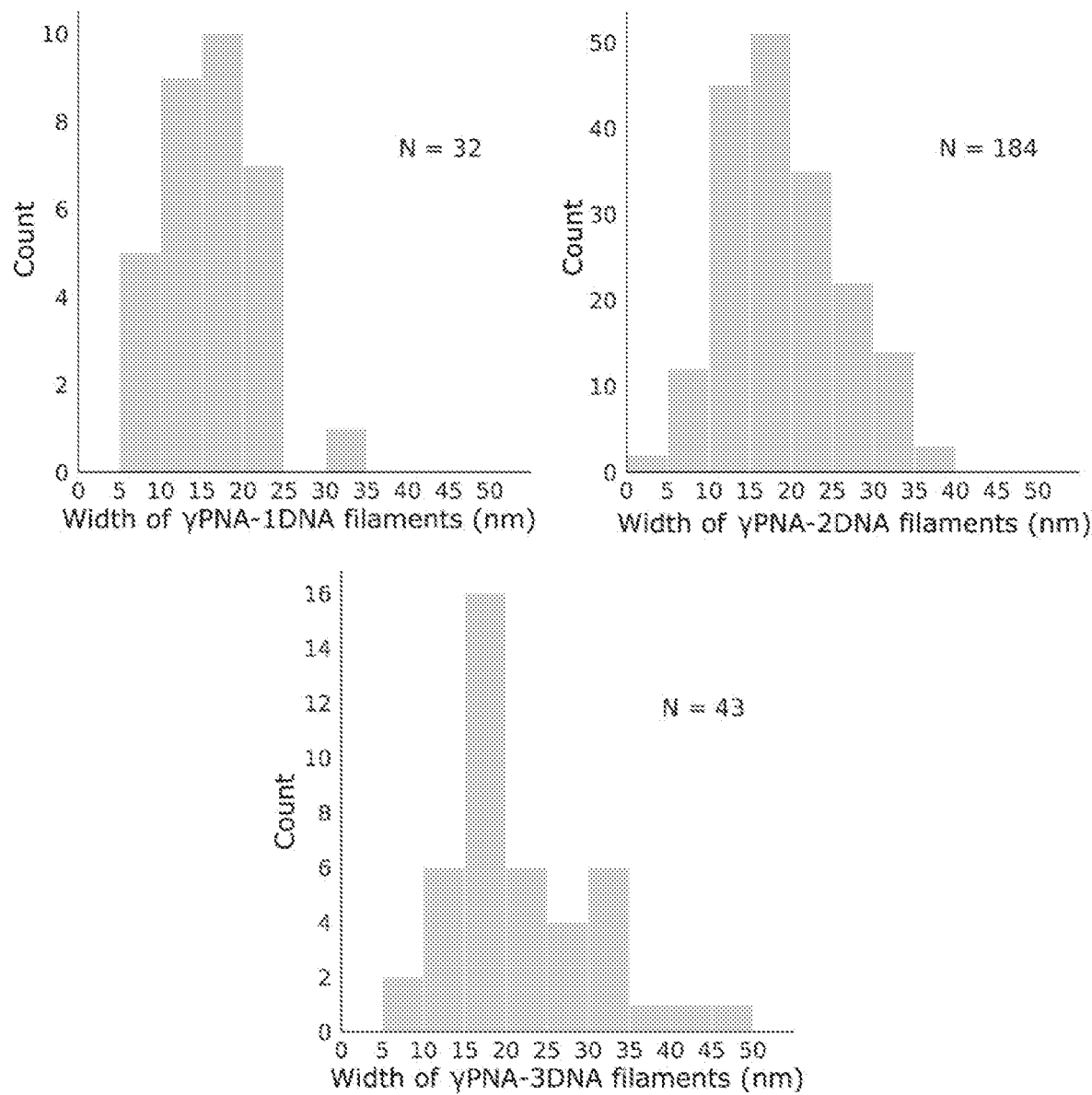
FIG. 18: Width profiles of self-assembled γPNA-DNA hybrid nanotubes from TEM images (Left to Right). Width histograms of 3-helix γPNA-DNA hybrid tubes self-assembled in 75% DMSO:H$_2$O introducing 1 contiguous DNA oligomer (left, D3 oligomer, N=32), 2 contiguous DNA oligomers (center, oligomers—D3 and D5, N=184) and 3 contiguous DNA oligomers (right, oligomers-D3, D5 and D9, N=43) obtained from TEM experiments. Median widths were estimated at 15.5 nm, 17.9 nm and 19 nm for 1, 2 and 3 contiguous DNA oligomer substitutions, respectively. No statistically significant difference between all 4 constructs could be reported.

Furthermore, width distribution for contiguous DNA replacement constructs show median widths similar to all-PNA constructs (FIG. 18). This indicates that localized improvements to surface hydrophilicity through charge modifications provides little stabilization to bundling tendencies for these constructs, further indicating a need for more uniform surface modifications. TEM images of the crossover-substituted PNA-DNA tubes also suggest looser weaving or perhaps edge-fraying that may be related to a partially disrupted crossover architecture. (FIG. 14B (d-f), TEM panels).

Figure 19A:
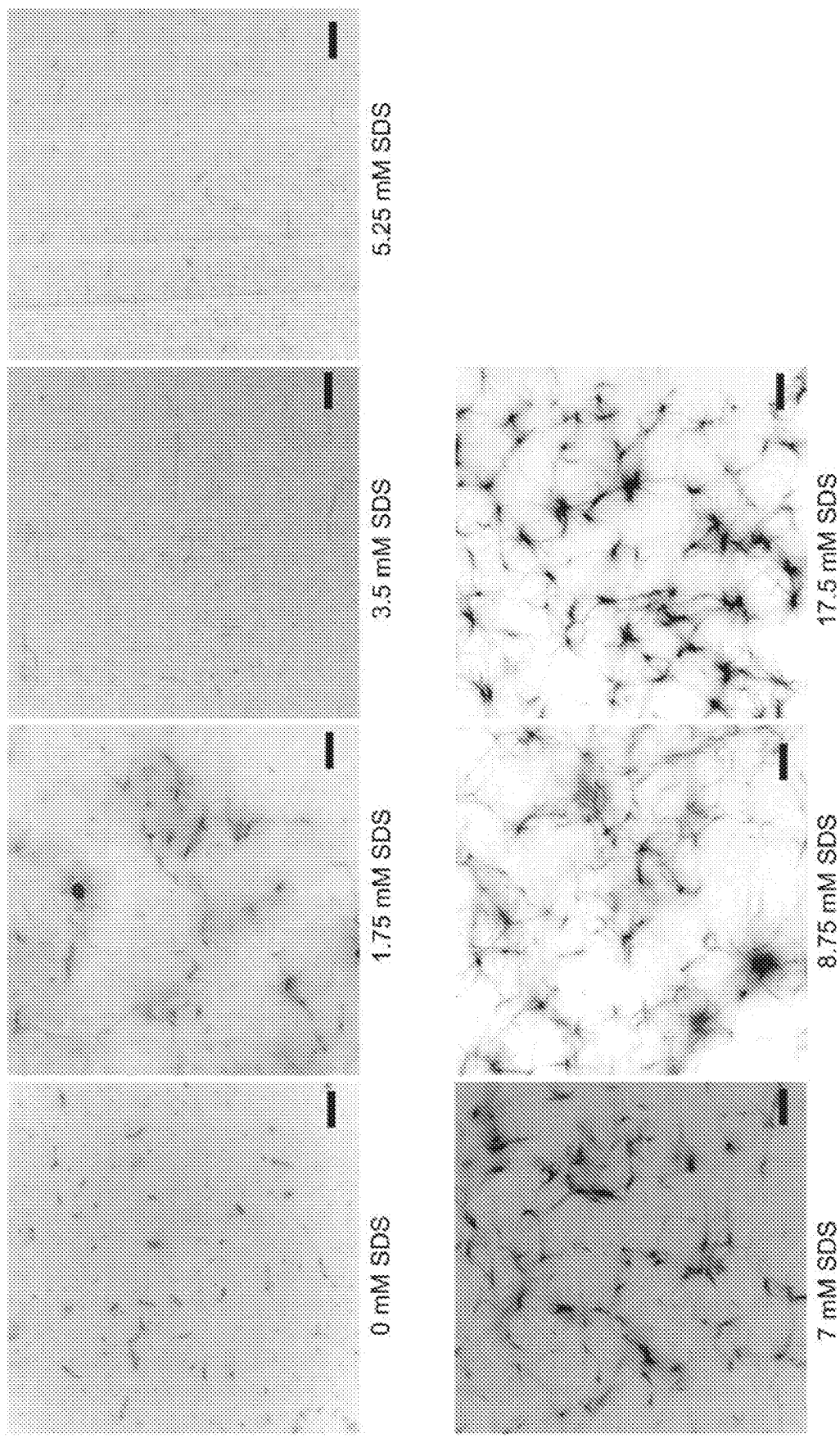
FIGS. 19A-19C: Effect of SDS on the width of PNA nanotubes during self-assembly using TIRF and TEM assays.
Figure 20:
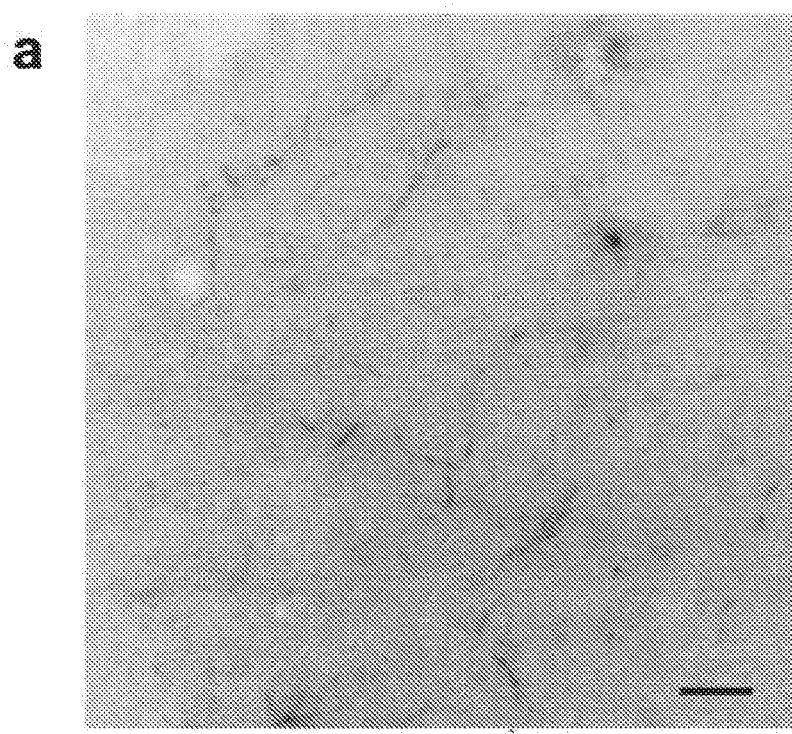
FIG. 20: TIRF assay images on the effect of SDS towards reduced bundling in crossover oligomer replacements. a) TIRF (5 μm scale bar) images of 3 DNA oligomer crossover replacements in the presence of 5.25 mM SDS during self-assembly shows disappearance of stellate-like morphology. b) Similar effects are seen when TIRF (5 μm scale bar) assays are performed with the replacement of 3 aeg-PNA oligomer crossover replacements in the presence of 5.25 mM SDS during self-assembly. This is indicative of the capability of anionic surfactants like SDS to counter increased non-specific interactions between hybrid nanotube structures promoted by hydrophobic effects.
Figure 20:
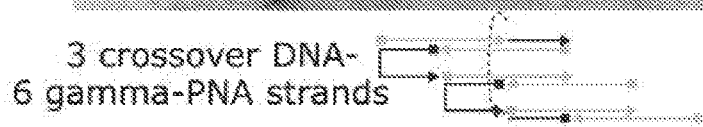
Figure 20:
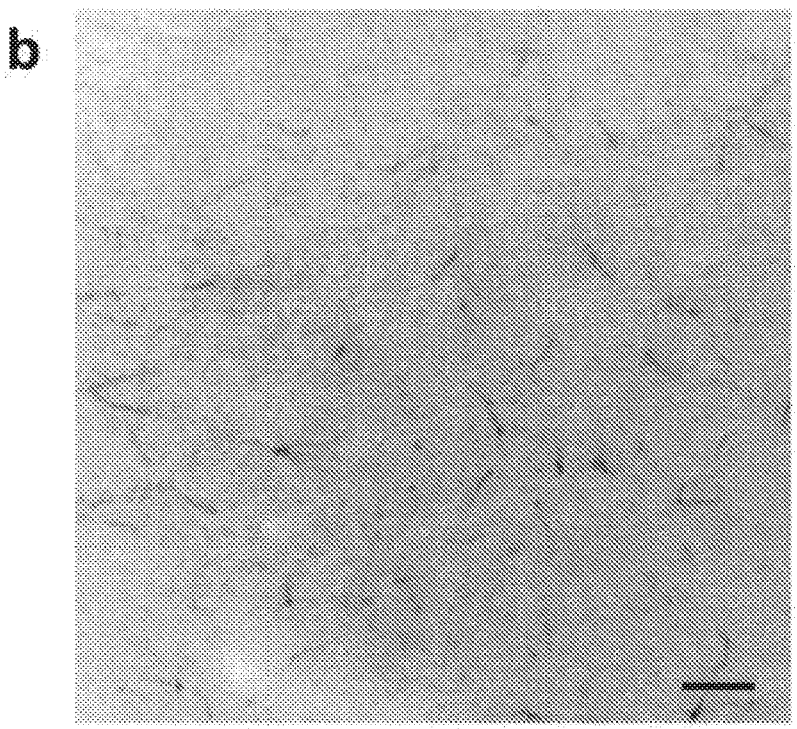
Figure 20:
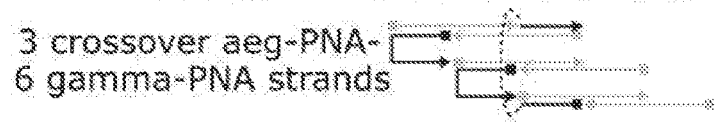

Influence of SDS on bundling of PNA nanotubes during self-assembly. We investigated the regulatory effects of anionic surfactant SDS on the morphology of PNA nanotubes during self-assembly in 75% DMSO:$H_2O$ (v/v), specifically its effects towards reduced bundling. We studied the effects of increasing SDS concentration both, below and above its critical micelle concentration (CMC, 8.2 mM), towards reduced PNA nanotube bundling using TIRF assays. As seen in FIG. 19A, TIRF panels show that upon increasing SDS concentration up to 5.25 mM, thinner morphologies of nanotubes based on fluorescence intensity become more dominant. This may indicate that the SDS-induced development of a net charge across the nanotube structure with increasing SDS concentrations results in reduction of bundling of PNA nanotubes. To verify this capability of SDS to reduce non-specific interactions between nanotubes, we performed TIRF assays on PNA crossover replacements with both their equivalent DNA and aeg-PNA crossover oligomers in the presence of 5.25 mM SDS. As highlighted above, we observed stellate-like morphologies in both cases in the absence of SDS. However, in the presence of SDS, we were able to visually observe the disappearance of stellate-like morphologies, suggesting that electrostatic interactions introduced by SDS in the system are able to counter the increased non-specific interactions caused by overall hydrophobic effects in hybrid nanotubes (See, FIG. 20). Additionally, when concentrations of SDS neared or exceeded the CMC concentration, appearance of largely networked PNA nanotubes occur with increasing propensity (FIG. 19A).

Figure 19B:
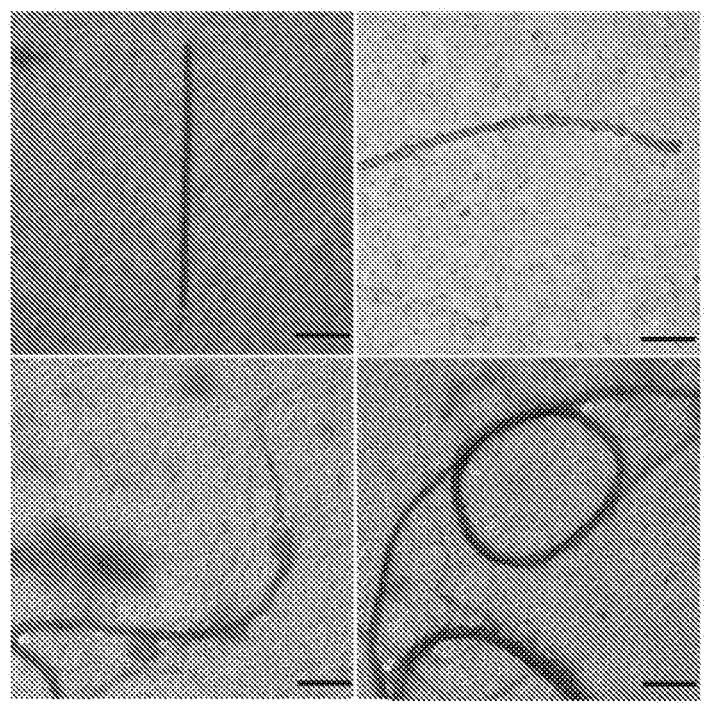
Figure 19C:
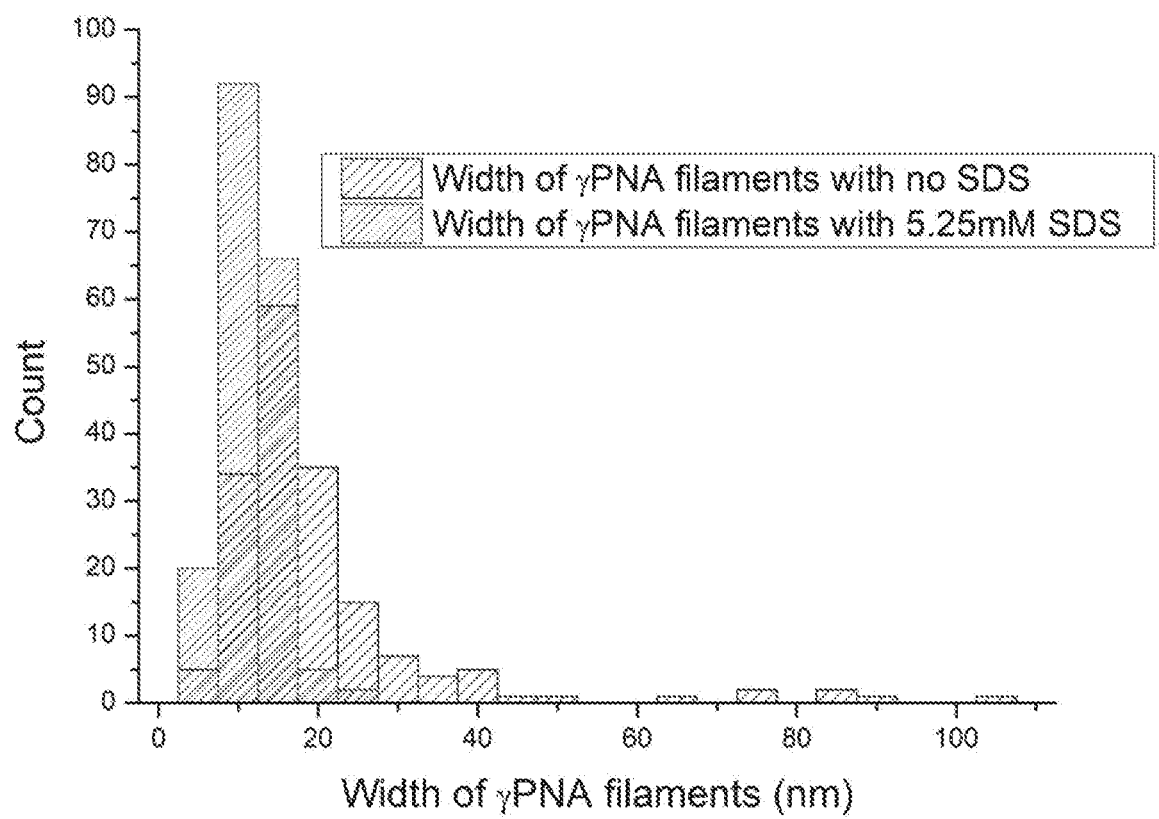

TEM imaging of the all-PNA co-self-assembly in the 75% DMSO:$H_2O$ solvent mixture along with 5.25 mM SDS confirmed the formation of nanotubes with diameters predominantly between 8-12 nm at nanoscopic resolutions (FIG. 19B). Width profile measurements made using TEM imaging confirmed that PNA nanotubes in the presence of 5.25 mM SDS have a tight width distribution with a median width of 11.3 nm (FIG. 19C). Therefore, the addition of anionic surfactants like SDS provides a simple and effective way for regulating the self-assembly morphology of PNA nanotubes by changing the surfactant concentration.

Described above is the modular self-assembly of the nanomaterial PNA to form nanotube structures. This work demonstrates that conformation-enhancing modifications of γPNA provide high cooperativity, thermal stability, and specificity that enable robust nanostructure formation. It is noted that while in several cases the introduction of more than 50% aeg-PNA to the oligomer set led to the formation of aggregates, this result may be specific to the SST structural motif, size and solvent conditions associated in this study. Suitable design of the structural motif accounting for the reduced cooperativity and thermal stability of aeg-PNA in comparison to γPNA, and tuning thermal ramp rates, solvent choice, pH and charge modifications to counter kinetic traps, hydrophobic effects and solubility are expected to stabilize such structures.

The solvophilic capability of γPNA to form nanostructures in organic solvent mixtures demonstrates that γPNA nanostructures can be more than just mimics of DNA nanostructures; these systems extend the range and utility of nucleic acid nanotechnology to harsh environments like organic solvents. Our studies show that in the presence of appropriate concentrations of anionic surfactants like SDS, γPNA oligomers can form nanotube populations with a tight width distribution. Interestingly, bundled growth may be a useful characteristic of γPNA nanotechnology, potentially enabling future applications for surface coating and micropatterning with PNA nanomaterials.

This study has focused on the design and formation of micron-scale filaments using a specific SST structural motif and specific type and density of mini-PEG-modifications on PNA. Therefore, future studies are needed to investigate additional structural motifs and the effects of type and density of gamma functionalization on these systems to expand towards a 3D architectural space. One example of this includes recent work from the Heemstra group on the self-assembly of micellar architecture using PNA with specific amino acid-modifications showing the capability to encode bilingual behavior through protein and nucleobase codes towards more complex nanoarchitectures (Swenson, C. S., Velusamy, A., Argueta-Gonzalez, H. S. & Heemstra, J. M. Bilingual Peptide Nucleic Acids: Encoding the Languages of Nucleic Acids and Proteins in a Single Self-Assembling Biopolymer. *J. Am. Chem. Soc.* 141, 19038 (2019)). Here, it also is demonstrated the formation of hybrid PNA-DNA nanostructures, and this approach indicates that this hybrid material may find uses in responsive coatings, therapeutics and passivation approaches for DNA-based nanosystems. In addition, understanding the mechanics of these hybrid systems may be useful for implementing conformation-switching nanostructures through strategies such as toehold-mediated strand displacement already shown in DNA nanostructures. Future opportunities for responsive PNA nanosystems may take advantage of the uniquely tunable biorthogonality of left-handed PNA and potential for strand-displacement-driven switchability driven by high-affinity PNA.

This work provides a proof of concept demonstration that micron-scale all-PNA and hybrid PNA-DNA nanostructures can be formed in organic solvent mixtures that meet the following criteria: (1) solvent mixtures are sufficiently polar to retain solubility of the PNA-DNA complexes even above 50% organic solvent; (2) solvent mixtures are aprotic or otherwise have reduced hydrogen-bonding donor/acceptor activity of the solvent to promote nucleobase hydrogen-bonding; and (3) solvent mixtures have a high boiling point to allow for slow thermal ramp annealing in the context of multiple unique oligomers to avoid kinetic traps or misfolding. Given the inherent nuclease and protease resistance of PNA, robust water-based formation of PNA nanostructures is needed and could be particularly useful for biological applications in vitro and in vivo. These PNA-based nanomaterials have transformative potential to extend the capability of nucleic acid nanotechnology towards more diverse nano-sensing and biomedical applications.

Example 7—Four-Helix Ss-γPNA SST Structure

Figure 21:
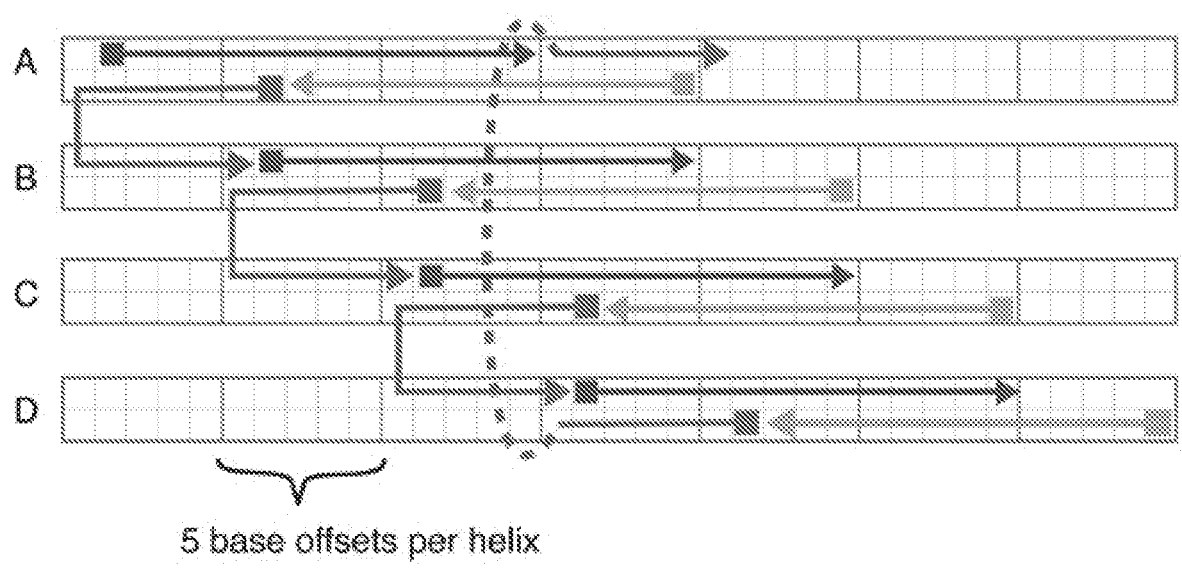
FIG. 21 depicts an exemplary four-helix ss-γPNA SST structure.
Figure 21:
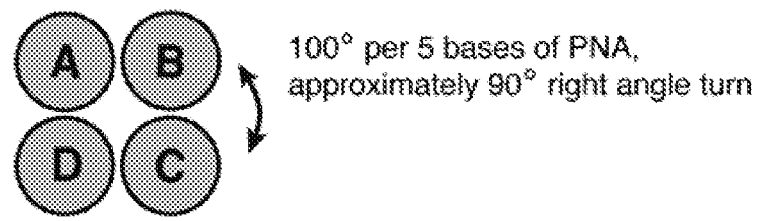

A four-helix nanotube design is provided. An example of such a design is depicted in FIG. 21. The four-helix nanotube design has a repeating unit that is 20 bases long, which assumes 20 bases per turn (close to PNA's measured 18 bases per turn). A helix-to helix offset of five bases allows for approximately a 90 degree rotation. This design consists of 12 distinct PNA strands that are 13 and 14 bases in length. However if made radially symmetric, only four distinct strands are needed, with three used in each repeat.

Example 8—Six-Helix Ss-γPNA SST Structure

Figure 22:
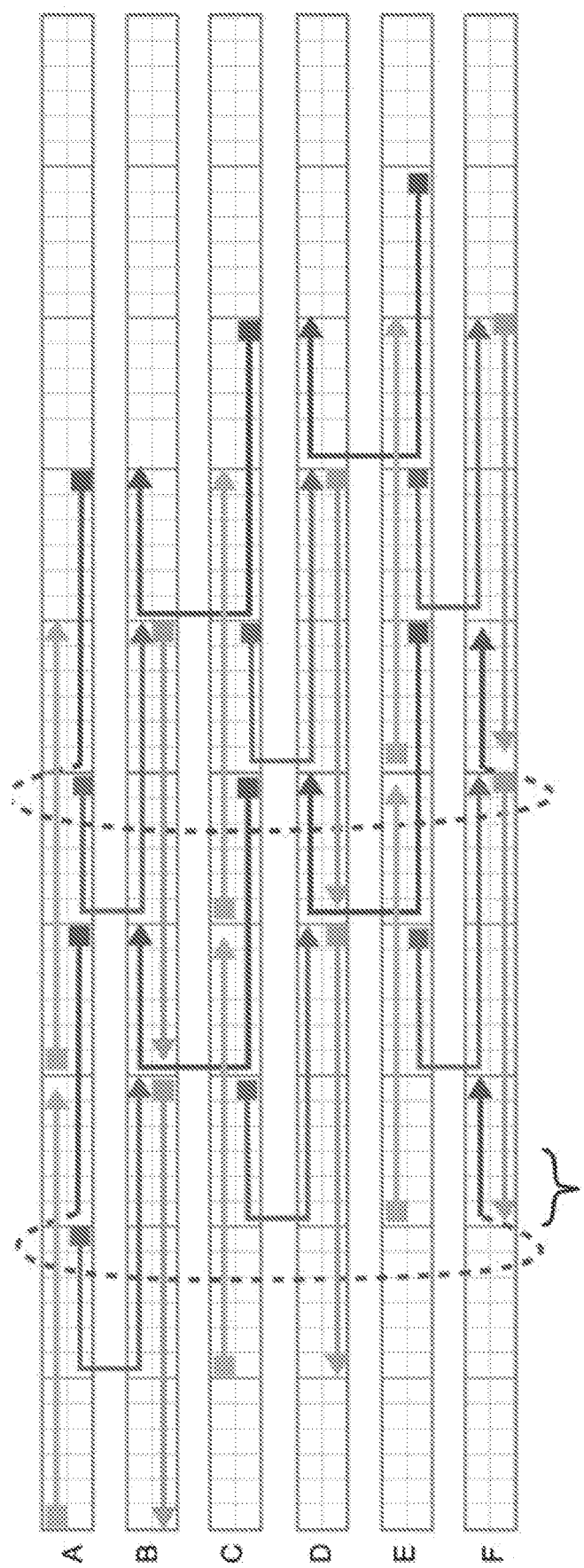
FIG. 22 depicts an exemplary six-helix ss-γPNA SST structure.
Figure 22:
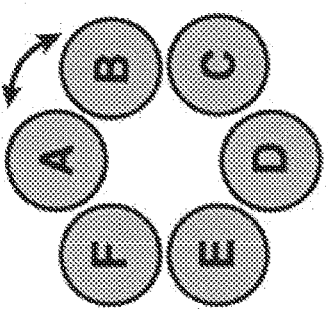

A six-helix nanotube design is provided. An example of such a design is depicted in FIG. 22. The six-helix nanotube design has a repeating unit that is 18 bases long, which assumes 18 bases per turn (equal to PNAs measured 18 bases per turn). Helix-to-helix offset of three bases allows for a 60 degree rotation between helices. This design consists of 12 distinct PNA strands that are 18 bases long. One repeat and two repeats of the same design are shown below. If the design is made to be radially symmetric, only four distinct strands are needed, with three used in each repeat.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments.

What is claimed is:

1. A single-stranded tile (SST) structure, comprising a complex of one or more single-stranded gamma peptide-nucleic acid (ss-γPNA) species, the ss-γPNAs of the SST structure comprising one or more pairs of complementary binding domains arranged on the one or more ss-γPNA species to produce a periodic arrangement of at least 3 molecules of the one or more ss-γPNA species by hybridization of the complementary nucleobase sequences of the one or more pairs of complementary binding domains.

2. The structure of claim 1, comprising a periodic arrangement of three or more ss-γPNA species, each ss-γPNA species having at least one or more binding domain that is a member of one or more binding domain pairs of the ss-γPNA species of the structure, where the binding domains are arranged on the ss-γPNA species to produce the periodic arrangement.

3. The structure of claim 1, comprising at least 10 periodically-arranged ss-γPNA molecules.

4. The structure of claim 1, wherein at least one of the ss-γPNA molecules of a first ss-γPNA species are hybridized to at least two ss-γPNA molecules of one or more different ss-γPNA species than the first ss-γPNA species.

5. The structure of claim 4, wherein at least two ss-γPNA molecules having different sequences from each other are hybridized to at least two of the ss-γPNA molecules having different sequences.

6. The structure of claim 1, wherein the ss-γPNA backbone of the one or more ss-γPNA species comprises a plurality of γPNA backbone residues linked to a nucleobase, in which one or more of the γPNA backbone residues are substituted with a group an ethylene glycol unit having from 1 to 100 ethylene glycol residues, optionally at the gamma carbon.

7. The structure of claim 1, wherein one or more of the ss-γPNA species comprises a RH-γPNA residue.

8. The structure of claim 1, wherein one or more of the ss-γPNA species comprises a LH-γPNA residue.

9. The structure of claim 1, wherein both LH-γPNA residues and RH-γPNA residues are present in the one or more ss-γPNA species.

10. The structure of claim 1, wherein one or more of the one or more ss-γPNA species has the structure:

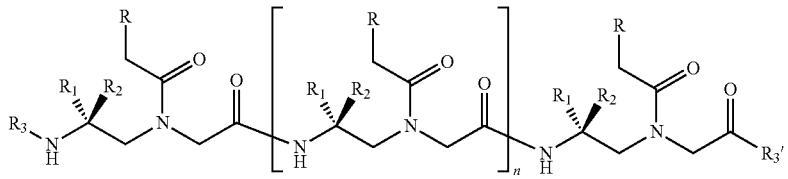

where,
each R is independently, a nucleobase;
n is 3 or more, 4 or more, 5 or more, or 6 or more;
each $R_1$ and $R_2$ are, independently: a guanidine-containing group, an amino acid side chain, methyl, ethyl, linear or branched $(C_3$-$C_8)$alkyl, $(C_2$-$C_8)$alkenyl, $(C_2$-$C_8)$alkynyl, $(C_1$-$C_8)$ hydroxyalkyl, $(C_3$-$C_8)$aryl, $(C_3$-$C_8)$cycloalkyl, $(C_3$-$C_8)$aryl $(C_1$-$C_6)$alkylene, $(C_3$-$C_8)$ cycloalkyl $(C_1$-$C_6)$alkylene, each optionally substituted with a polyethylene glycol chain comprising from 1 to 50 units; H—$CH_2$—$(OCH_2$—$CH_2)_q OP_1$; —$CH_2$—$(OCH_2$—$CH_2)_q$—$NHP_1$; —$CH_2$—$(SCH_2$—$CH_2)_q$—$SP_1$; —$CH_2$—$(OCH_2$—$CH_2)_r$—OH; —$CH_2$—$(OCH_2$—$CH_2)_r$—$NH_2$; —$CH_2$—$(OCH_2$—$CH_2)_r$—$NHC(NH)NH_2$; or —$CH_2$—$(OCH_2$—$CH_2)_r$—S—S [$CH_2CH_2$]$_s NHC(NH)NH_2$, where $P_1$ is H, $(C_1$-$C_8)$alkyl, $(C_2$-$C_8)$alkenyl, $(C_2$-$C_8)$alkynyl, $(C_3$-$C_8)$aryl, $(C_3$-$C_8)$cycloalkyl, $(C_3$-$C_8)$aryl, $(C_1$-$C_6)$alkylene or $(C_3$-$C_8)$ cycloalkyl $(C_1$-$C_6)$alkylene; q is an integer from 0 to 50; r is an integer from 1 to 50, and s is an integer from 1 to 50;
$R_3$ is H or one or more natural or non-proteinogenic amino acids, a guanidine-containing group, a tag or a label; and
$R_3'$ is OH or one or more natural or non-proteinogenic amino acids, a guanidine-containing group, a tag or a label.

11. The structure of claim 1, comprising a plurality of linearly-arranged contiguous strands comprising at least one of the one or more of the ss-γPNA species, and each of the contiguous strands comprising binding domains complementary to a binding domain on a different contiguous strand, forming a linear structure.

12. The structure of claim 11, further comprising:
two or more pluralities of linearly-arranged contiguous strands comprising at least one of the one or more of the ss-γPNA species producing two or more linear structures; and
one or more crosslinking strands comprising at least one of the one or more of the ss-γPNA species that each bind nucleobase sequences in two different linear structures formed from the pluralities of linearly-arranged contiguous strands, forming an ordered bundle of the linear structures.

13. The structure of claim 12, comprising three different linear structures, and three different crosslinking ss-γPNA strands forming an ordered bundle of three linear structures.

14. The structure of claim 1, wherein the complementary binding domains are less than 10 contiguous nucleobases each.

15. The structure of claim 1, wherein at least one of the one or more of the ss-γPNA species has at least 10%, by number, γPNA residues.

16. A method of making a single-stranded tile (SST) structure, comprising:
mixing one or more single-stranded gamma peptide-nucleic acid (ss-γPNA) species in a solvent for the ss-γPNA; and
complexing the one or more ss-γPNA species in the solvent to form an ordered complex of the one or more single-stranded gamma peptide-nucleic acids (ss-γPNAs),
wherein the ss-γPNA species comprising one or more pairs of complementary binding domains comprising complementary nucleobase sequences arranged on the one or more ss-γPNA species to produce a periodic arrangement of at least 3 molecules of the one or more ss-γPNA species by hybridization of the complementary nucleobase sequences to produce the SST structure.

17. The method of claim 16, comprising mixing in the solvent a plurality of linearly-arranged contiguous strands comprising at least one of the one or more of the ss-γPNA species, and each of the contiguous strands comprising binding domains complementary to a biding domain on a different contiguous strand, forming a linear structure on hybridization of the complementary binding domains, and optionally mixing in the solvent two or more pluralities of contiguous strands comprising at least one of the one or more of the ss-γPNA species, and each of the contiguous strands comprising binding domains complementary to a binding domain on a different contiguous strand, producing two or more linear structures on hybridization of the complementary binding domains; and one or more crosslinking strands comprising at least one of the one or more of the ss-γPNA species that each bind complementary nucleobase sequences in two different linear structures formed from the pluralities of linearly-arranged contiguous strands, forming an ordered bundle of the linear structures on hybridization of the complementary binding domains and further optionally comprising mixing in the solvent three pluralities of contiguous strands comprising at least one of the one or more of the ss-γPNA species, producing three linear structures on hybridization of the complementary binding domains; and three different crosslinking ss-γPNA strands, forming an ordered bundle of three linear structures on hybridization of the complementary binding domains.

18. The method of claim 16, wherein the temperature is lowered step-wise to hybridize different binding domain pairs in an order.

19. A nanoscale actuator comprising an SST structure according to claim 1, and a nucleic acid or nucleic acid analog able to hybridize with a binding domain of a strand of the SST structure and altering the structure of the SST structure.

20. A method of modifying an SST structure, comprising contacting an SST structure comprising a PNA strand of claim 1 with a nucleic acid or nucleic acid analog able to hybridize with a binding domain of a strand of the SST structure and altering the structure of the SST structure, and thereby changing the physical structure of the SST structure.

21. The method of claim 20, further comprising detecting a change in the physical structure of the SST structure from contacting the SST structure with the nucleic acid or nucleic acid analog able to hybridize with a binding domain of a strand of the SST structure and altering the structure of the SST structure.

22. A sensor system comprising an SST structure comprising a PNA strand of claim 1 that is actuated by an analyte.

23. A method of sensing an analyte, comprising contacting the analyte with an SST structure comprising a PNA strand of claim 1, that is actuated by the analyte, and detecting actuation of the SST structure by the analyte.

* * * * *

```
                        SEQUENCE LISTING

<160> NUMBER OF SEQ ID NOS: 10

<210> SEQ ID NO 1
<211> LENGTH: 12
<212> TYPE: DNA
<213> ORGANISM: Artificial Sequence
<220> FEATURE:
<223> OTHER INFORMATION: DNA D1

<400> SEQUENCE: 1
aatagcgttc ac                                                         12

<210> SEQ ID NO 2
<211> LENGTH: 12
<212> TYPE: DNA
<213> ORGANISM: Artificial Sequence
<220> FEATURE:
<223> OTHER INFORMATION: DNA D2

<400> SEQUENCE: 2
gctattgagt aa                                                         12

<210> SEQ ID NO 3
<211> LENGTH: 12
<212> TYPE: DNA
<213> ORGANISM: Artificial Sequence
<220> FEATURE:
<223> OTHER INFORMATION: DNA D3

<400> SEQUENCE: 3
gacatcttac tc                                                         12

<210> SEQ ID NO 4
<211> LENGTH: 12
<212> TYPE: DNA
<213> ORGANISM: Artificial Sequence
<220> FEATURE:
<223> OTHER INFORMATION: DNA D4

<400> SEQUENCE: 4
```
ctggcgtgcg ga                                                          12

<210> SEQ ID NO 5
<211> LENGTH: 12
<212> TYPE: DNA
<213> ORGANISM: Artificial Sequence
<220> FEATURE:
<223> OTHER INFORMATION: DNA D5

<400> SEQUENCE: 5
cgccagccct cg                                                          12

<210> SEQ ID NO 6
<211> LENGTH: 12
<212> TYPE: DNA
<213> ORGANISM: Artificial Sequence
<220> FEATURE:
<223> OTHER INFORMATION: DNA D6

<400> SEQUENCE: 6
gtgaaccgag gg                                                          12

<210> SEQ ID NO 7
<211> LENGTH: 12
<212> TYPE: DNA
<213> ORGANISM: Artificial Sequence
<220> FEATURE:
<223> OTHER INFORMATION: DNA D7

<400> SEQUENCE: 7
agttttgatg tc                                                          12

<210> SEQ ID NO 8
<211> LENGTH: 12
<212> TYPE: DNA
<213> ORGANISM: Artificial Sequence
<220> FEATURE:
<223> OTHER INFORMATION: DNA D8

<400> SEQUENCE: 8
aaaactacag aa                                                          12

<210> SEQ ID NO 9
<211> LENGTH: 12
<212> TYPE: DNA
<213> ORGANISM: Artificial Sequence
<220> FEATURE:
<223> OTHER INFORMATION: DNA D9

<400> SEQUENCE: 9
tccgcattct gt                                                          12

<210> SEQ ID NO 10
<211> LENGTH: 13
<212> TYPE: DNA
<213> ORGANISM: Artificial Sequence
<220> FEATURE:
<223> OTHER INFORMATION: gamma PNA P2m

<400> SEQUENCE: 10
gctattgagt aaa                                                         13